(12) United States Patent
Basile

(10) Patent No.: US 8,962,317 B2
(45) Date of Patent: Feb. 24, 2015

(54) USES OF IL-12 AND THE IL-12 RECEPTOR POSITIVE CELL IN TISSUE REPAIR AND REGENERATION

(75) Inventor: Lena A. Basile, Tujunga, CA (US)

(73) Assignee: Neumedicines, Inc., Pasadena, CA (US)

( * ) Notice: Subject to any disclaimer, the term of this patent is extended or adjusted under 35 U.S.C. 154(b) by 0 days.

(21) Appl. No.: 13/824,224

(22) PCT Filed: Sep. 27, 2011

(86) PCT No.: PCT/US2011/053450
§ 371 (c)(1), (2), (4) Date: Jun. 3, 2013

(87) PCT Pub. No.: WO2012/050829
PCT Pub. Date: Apr. 19, 2012

(65) Prior Publication Data
US 2013/0259828 A1  Oct. 3, 2013

Related U.S. Application Data

(60) Provisional application No. 61/387,419, filed on Sep. 28, 2010, provisional application No. 61/405,584, filed on Oct. 21, 2010, provisional application No. 61/409,407, filed on Nov. 2, 2010, provisional application No. 61/477,130, filed on Apr. 19, 2011.

(51) Int. Cl.
| | |
|---|---|
| C12N 5/0789 | (2010.01) |
| C12N 5/074 | (2010.01) |
| A61K 35/12 | (2006.01) |
| A61K 35/38 | (2006.01) |
| A61K 38/20 | (2006.01) |
| A61K 35/14 | (2006.01) |
| A61K 35/26 | (2006.01) |
| A61K 35/28 | (2006.01) |

(52) U.S. Cl.
CPC ............ *A61K 35/12* (2013.01); *A61K 35/38* (2013.01); *A61K 38/208* (2013.01); *A61K 35/14* (2013.01); *A61K 35/26* (2013.01); *A61K 35/28* (2013.01); *A61K 35/51* (2013.01); *C12N 5/0647* (2013.01); *C12N 2501/2312* (2013.01)
USPC ............................ 435/372; 435/386; 424/93.1

(58) Field of Classification Search
CPC combination set(s) only.
See application file for complete search history.

(56) References Cited

U.S. PATENT DOCUMENTS

| | | | | |
|---|---|---|---|---|
| 6,004,812 | A * | 12/1999 | Scadden et al. ............ | 435/372.3 |
| 6,338,848 | B1 | 1/2002 | Leonard et al. | |
| 7,939,058 | B2 | 5/2011 | Chen et al. | |
| 2005/0136034 | A1 | 6/2005 | Chen et al. | |
| 2009/0047241 | A1 | 2/2009 | Zhao et al. | |

OTHER PUBLICATIONS

Neta et al., J Immunol. Nov. 1, 1994;153(9):4230-4237.*
Hirao et al.,Stem Cells 13:45-53 (1995).*
Fisher et al., "Gene Expression During Differentiation of Human Dendtritic Cells from Cord Blood CD34 Stem Cells," *Cytokine*, vol. 11, No. 2, pp. 111-117 (1999).
International Search Report issued in related International Patent Application No. PCT/US2011/053450, completed Apr. 10, 2012.
Zhao Y, Lin Y, Zhan Y, Yang G, Louie J, Harrison DE, Anderson, WF. Murine hematopoietic stem cell characterization and its regulation in BM transplantation. Blood. 2000;96:3016-3022.
Zhong IF, Zhao Y, Sutton S. Su A, Zhan Y, Zhu L, Yan C, Gallaher T, Johnston PB, Anderson WF, Cooke MP. Gene expression profile of murine long-term reconstituting vs. short-term reconstituting hematopoietic stem cells. Proc Natl Acad Sci USA. 2005; 102:2448-2453.
Lertmemongkolchai G, Cai G, Hunter CA, Bancroft GJ. Bystander activation of CD8+ T cells contributes to the rapid production of IFN-gamma in response to bacterial pathogens. Journal of Immunology. 2001;166:1097-1105.
Cui J, Shin T, Kawano T, Sato H, Kondo E, Toura I, Kaneko Y, Koseki H, Kanno M, Taniguchi M. Requirement for Valphal4 NKT cells in IL-12-mediated rejection of tumors. Science. 1997;278:1623-1626.
Ohteki T, Fukao T, Suzue K, Maki C, Ito M, Nakamura M, Koyasu S. Interleukin 12-dependent interferon gamma production by CD8alpha+ lymphoid dendritic cells. J Exp. Med. 1999;189:1981-1986.
Airoldi I, Gri G, Marshall JD, Corcione A, Facchetti P, Guglielmino R, Trinchieri G, Pistoia V. Expression and function of IL-12 and IL-18 receptors on human tonsillar B cells. Journal of Immunol. 2000;165:6880-6888.
Hsieh CS, Macatonia SE, Tripp CS, Wolf SF, O'Garra A, Murphy KM. Development of TH1 CD4+ T cells through IL-12 produced by Listeria-induced macrophages. Science. 1993;260:547-549.
Manetti R, Parronchi P, Giudizi MG, Piccinni MG, Maggi E, Trinchieri G, Romagnani S. Natural killer cell stimulatory factor (interleukin 12 [IL-12]) induces T helper type 1 (Thl )-specific immune responses and inhibits the development of IL-4-producing Th cells. J. Exp. Med. 1993;177:1199-1204.
Brunda MJ, Luistro L, Warrier RR, Wright RB, Hubbard BR, Murphy M, Wolf SF, Gately MK. Antitumor and antimetastatic activity of interleukin 12 against murine tumors. J. Exp. Med. 1993;178:1223-1230.
Noguchi Y, Jungbluth A, Richards EC, Old LJ. Effect of interleukin 12 on tumor induction by 3-methylcholanthrene. Proc Natl Acad Sci USA. 1996;93:11798-11801.
Colombo MP, Trinchieri G. Interleukin-12 in anti-tumor immunity and immunotherapy. Cytokine Growth Factor Rev. 2002;13:155-168.
Yao L, Pike SE, Setsuda J, Parekh J, Gupta G, Raffeld M, Jaffe ES, Tosato G. Effective targeting of tumor vasculature by the angiogenesis inhibitors vasostatin and interleukin-12. Blood. 2000;96:1900-1905.
Eng VM, Car BD, Schnyder B, Lorenz M, Lugli S, Aguet M, Anderson TD, Ryffel B, Quesniaux VF. The stimulatory effects of interleukin (IL)-12 on hematopoiesis are antagonized by IL-12-induced interferon gamma *in vivo*. J Exp. Med. 1995;181:1893-1898.

(Continued)

*Primary Examiner* — Daniel C Gamett
(74) *Attorney, Agent, or Firm* — Foley & Lardner LLP

(57) ABSTRACT

The present application relates to stem cells isolated from various sources within the body of a patient or of a healthy donor and identified by the presence of the interleukin 12 (IL-12) receptor. The present application also provides methods for making and for using the stem cells.

13 Claims, 21 Drawing Sheets

(56) References Cited

OTHER PUBLICATIONS

Car BD, Eng VM, Schnyder B, LeHir M, Shakhov AN, Woerly G, Huang S, Aguet M, Anderson TD, Ryffel B. Role of interferon-gamma in interleukin 12-induced pathology in mice. Amer. J Path. 1995;147:1693-1707.

Neta R, Stiefel SM, Finkelman F, Herrmann S, Ali N. IL-12 protects bone marrow from and sensitizes intestinal tract to ionizing radiation. J Immunol. 1994;153:4230-4237.

Herodin F, Bourin P. Mayol JF, Lataillade JJ, Drouet M. Short-term injection of antiapoptotic cytokine combinations soon after lethal y-irradiation promotes survival. Blood. 2003;101:2609-2616.

Jackson JD, Yan Y, Brunda MJ, Kelsey LS, Talmadge JE. Interleukin-12 enhances peripheral hematopoiesis *in vivo*. Blood. 1995;85:2371-2376.

\* cited by examiner

Figure 6A
Figure 6B
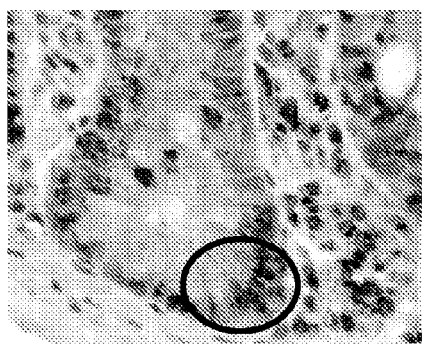
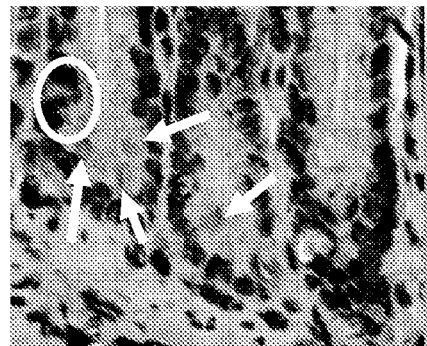
Figure 7A
Figure 7B
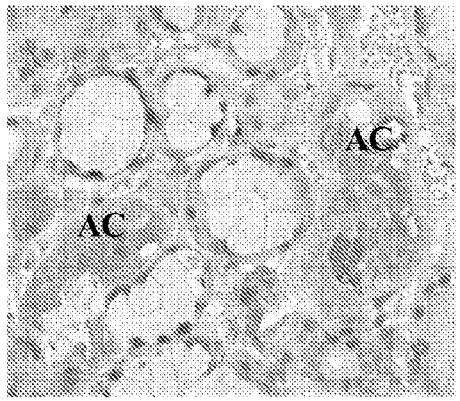
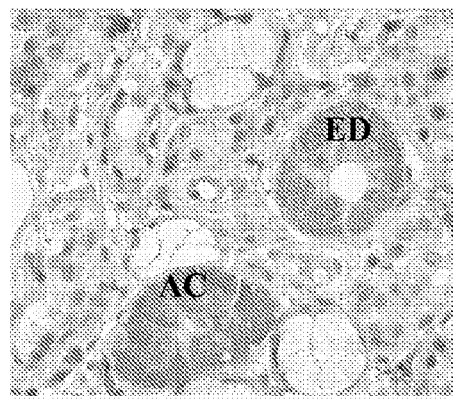

(f) Irradiation + rMuIL-12 at 24 hours and 4 days (g) Irradiation + rMuIL-12 at 24 hours △ Vehicle (n = 8)
○ rHuIL-12, 100 ng/kg at 24 hours (n = 8)
● rHuIL-12, 250 ng/kg at 24 hours (n = 8)

[a] Cell count (rHuIL-12 vs. vehicle):
P = .013 for 100 ng/kg at day 14.
P = .006 for 250 ng/kg at day 12.
P = .046 for 250 ng/kg at day 14.

△ Vehicle (n = 8)
● rHuIL-12, 250 ng/kg at 24 hours (n = 8)

[a] Cell count (rHuIL-12 vs. vehicle):
P = .003 at days 12 and 14.

Figure 18A
Figure 18B
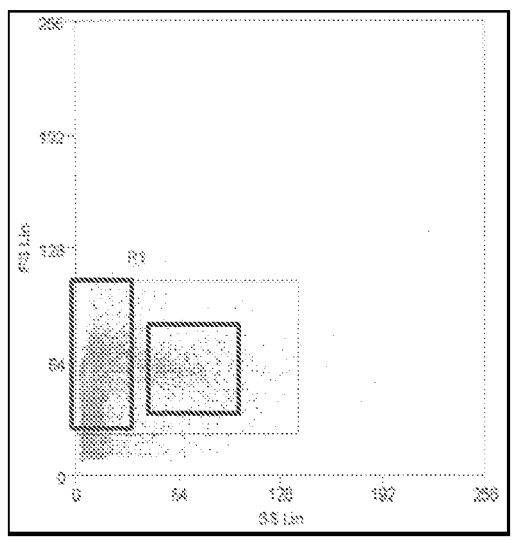
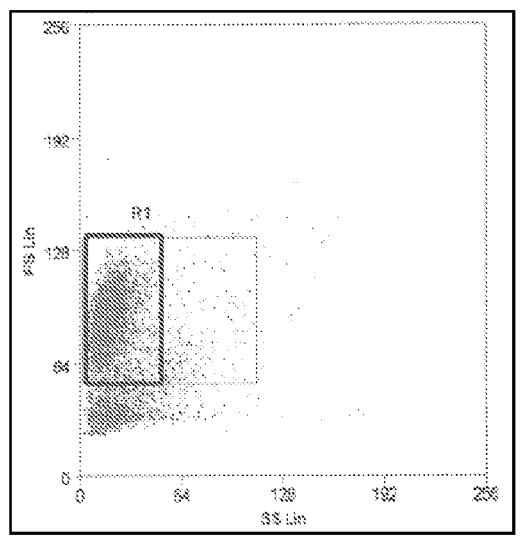

SEQUENCE LISTING

<160> NUMBER OF SEQ ID NOS: 4

<210> SEQ ID NO 1
<211> LENGTH: 197
<212> TYPE: PRT
<213> ORGANISM: Homo sapiens

<400> SEQUENCE: 1

```
Arg Asn Leu Pro Val Ala Thr Pro Asp Pro Gly Met Phe Pro Cys Leu
1               5                  10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195
```

<210> SEQ ID NO 2
<211> LENGTH: 306
<212> TYPE: PRT
<213> ORGANISM: Homo sapiens

<400> SEQUENCE: 2

```
Ile Trp Glu Leu Lys Lys Asp Val Tyr Val Val Glu Leu Asp Trp Tyr
1               5                  10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
```

```
            100             105             110
Asn Tyr Ser Gly Arg Phe Thr Cys Trp Trp Leu Thr Thr Ile Ser Thr
            115             120             125
Asp Leu Thr Phe Ser Val Lys Ser Ser Arg Gly Ser Ser Asp Pro Gln
            130             135             140
Gly Val Thr Cys Gly Ala Ala Thr Leu Ser Ala Glu Arg Val Arg Gly
145             150             155             160
Asp Asn Lys Glu Tyr Glu Tyr Ser Val Glu Cys Gln Glu Asp Ser Ala
            165             170             175
Cys Pro Ala Ala Glu Glu Ser Leu Pro Ile Glu Val Met Val Asp Ala
            180             185             190
Val His Lys Leu Lys Tyr Glu Asn Tyr Thr Ser Ser Phe Phe Ile Arg
            195             200             205
Asp Ile Ile Lys Pro Asp Pro Pro Lys Asn Leu Gln Leu Lys Pro Leu
            210             215             220
Lys Asn Ser Arg Gln Val Glu Val Ser Trp Glu Tyr Pro Asp Thr Trp
225             230             235             240
Ser Thr Pro His Ser Tyr Phe Ser Leu Thr Phe Cys Val Gln Val Gln
            245             250             255
Gly Lys Ser Lys Arg Glu Lys Lys Asp Arg Val Phe Thr Asp Lys Thr
            260             265             270
Ser Ala Thr Val Ile Cys Arg Lys Asn Ala Ser Ile Ser Val Arg Ala
            275             280             285
Gln Asp Arg Tyr Tyr Ser Ser Ser Trp Ser Glu Trp Ala Ser Val Pro
            290             295             300
Cys Ser
305

<210> SEQ ID NO 3
<211> LENGTH: 662
<212> TYPE: PRT
<213> ORGANISM: Homo sapiens

<400> SEQUENCE: 3

Met Glu Pro Leu Val Thr Trp Val Val Pro Leu Leu Phe Leu Phe Leu
1               5               10              15
Leu Ser Arg Gln Gly Ala Ala Cys Arg Thr Ser Glu Cys Cys Phe Gln
            20              25              30
Asp Pro Pro Tyr Pro Asp Ala Asp Ser Gly Ser Ala Ser Gly Pro Arg
            35              40              45
Asp Leu Arg Cys Tyr Arg Ile Ser Ser Asp Arg Tyr Glu Cys Ser Trp
        50              55              60
Gln Tyr Glu Gly Pro Thr Ala Gly Val Ser His Phe Leu Arg Cys Cys
65              70              75              80
Leu Ser Ser Gly Arg Cys Cys Tyr Phe Ala Ala Gly Ser Ala Thr Arg
            85              90              95
Leu Gln Phe Ser Asp Gln Ala Gly Val Ser Val Leu Tyr Thr Val Thr
            100             105             110
Leu Trp Val Glu Ser Trp Ala Arg Asn Gln Thr Glu Lys Ser Pro Glu
            115             120             125
Val Thr Leu Gln Leu Tyr Asn Ser Val Lys Tyr Glu Pro Pro Leu Gly
            130             135             140
Asp Ile Lys Val Ser Lys Leu Ala Gly Gln Leu Arg Met Glu Trp Glu
145             150             155             160
```

```
Thr Pro Asp Asn Gln Val Gly Ala Glu Val Gln Phe Arg His Arg Thr
                165                 170                 175
Pro Ser Ser Pro Trp Lys Leu Gly Asp Cys Gly Pro Gln Asp Asp Asp
            180                 185                 190
Thr Glu Ser Cys Leu Cys Pro Leu Glu Met Asn Val Ala Gln Glu Phe
        195                 200                 205
Gln Leu Arg Arg Gln Leu Gly Ser Gln Gly Ser Ser Trp Ser Lys
    210                 215                 220
Trp Ser Ser Pro Val Cys Val Pro Pro Glu Asn Pro Pro Gln Pro Gln
225                 230                 235                 240
Val Arg Phe Ser Val Glu Gln Leu Gly Gln Asp Gly Arg Arg Arg Leu
                245                 250                 255
Thr Leu Lys Glu Gln Pro Thr Gln Leu Glu Leu Pro Glu Gly Cys Gln
            260                 265                 270
Gly Leu Ala Pro Gly Thr Glu Val Thr Tyr Arg Leu Gln Leu His Met
        275                 280                 285
Leu Ser Cys Pro Cys Lys Ala Lys Ala Thr Arg Thr Leu His Leu Gly
    290                 295                 300
Lys Met Pro Tyr Leu Ser Gly Ala Ala Tyr Asn Val Ala Val Ile Ser
305                 310                 315                 320
Ser Asn Gln Phe Gly Pro Gly Leu Asn Gln Thr Trp His Ile Pro Ala
                325                 330                 335
Asp Thr His Thr Glu Pro Val Ala Leu Asn Ile Ser Val Gly Thr Asn
            340                 345                 350
Gly Thr Thr Met Tyr Trp Pro Ala Arg Ala Gln Ser Met Thr Tyr Cys
        355                 360                 365
Ile Glu Trp Gln Pro Val Gly Gln Asp Gly Gly Leu Ala Thr Cys Ser
    370                 375                 380
Leu Thr Ala Pro Gln Asp Pro Asp Pro Ala Gly Met Ala Thr Tyr Ser
385                 390                 395                 400
Trp Ser Arg Glu Ser Gly Ala Met Gly Gln Glu Lys Cys Tyr Tyr Ile
                405                 410                 415
Thr Ile Phe Ala Ser Ala His Pro Glu Lys Leu Thr Leu Trp Ser Thr
            420                 425                 430
Val Leu Ser Thr Tyr His Phe Gly Gly Asn Ala Ser Ala Ala Gly Thr
        435                 440                 445
Pro His His Val Ser Val Lys Asn His Ser Leu Asp Ser Val Ser Val
    450                 455                 460
Asp Trp Ala Pro Ser Leu Leu Ser Thr Cys Pro Gly Val Leu Lys Glu
465                 470                 475                 480
Tyr Val Val Arg Cys Arg Asp Glu Asp Ser Lys Gln Val Ser Glu His
                485                 490                 495
Pro Val Gln Pro Thr Glu Thr Gln Val Thr Leu Ser Gly Leu Arg Ala
            500                 505                 510
Gly Val Ala Tyr Thr Val Gln Val Arg Ala Asp Thr Ala Trp Leu Arg
        515                 520                 525
Gly Val Trp Ser Gln Pro Gln Arg Phe Ser Ile Glu Val Gln Val Ser
    530                 535                 540
Asp Trp Leu Ile Phe Phe Ala Ser Leu Gly Ser Phe Leu Ser Ile Leu
545                 550                 555                 560
Leu Val Gly Val Leu Gly Tyr Leu Gly Leu Asn Arg Ala Ala Arg His
                565                 570                 575
Leu Cys Pro Pro Leu Pro Thr Pro Cys Ala Ser Ser Ala Ile Glu Phe
```

```
                    580                 585                 590
        Pro Gly Gly Lys Glu Thr Trp Gln Trp Ile Asn Pro Val Asp Phe Gln
                        595                 600                 605

Glu Glu Ala Ser Leu Gln Glu Ala Leu Val Val Glu Met Ser Trp Asp
        610                 615                 620

Lys Gly Glu Arg Thr Glu Pro Leu Glu Lys Thr Glu Leu Pro Glu Gly
        625                 630                 635                 640

Ala Pro Glu Leu Ala Leu Asp Thr Glu Leu Ser Leu Glu Asp Gly Asp
                        645                 650                 655

Arg Cys Lys Ala Lys Met
                        660

<210> SEQ ID NO 4
<211> LENGTH: 862
<212> TYPE: PRT
<213> ORGANISM: Homo sapiens

<400> SEQUENCE: 4

Met Ala His Thr Phe Arg Gly Cys Ser Leu Ala Phe Met Phe Ile Ile
1               5                   10                  15

Thr Trp Leu Leu Ile Lys Ala Lys Ile Asp Ala Cys Lys Arg Gly Asp
                20                  25                  30

Val Thr Val Lys Pro Ser His Val Ile Leu Leu Gly Ser Thr Val Asn
            35                  40                  45

Ile Thr Cys Ser Leu Lys Pro Arg Gln Gly Cys Phe His Tyr Ser Arg
    50                  55                  60

Arg Asn Lys Leu Ile Leu Tyr Lys Phe Asp Arg Arg Ile Asn Phe His
65                  70                  75                  80

His Gly His Ser Leu Asn Ser Gln Val Thr Gly Leu Pro Leu Gly Thr
                85                  90                  95

Thr Leu Phe Val Cys Lys Leu Ala Cys Ile Asn Ser Asp Glu Ile Gln
            100                 105                 110

Ile Cys Gly Ala Glu Ile Phe Val Gly Val Ala Pro Glu Gln Pro Gln
    115                 120                 125

Asn Leu Ser Cys Ile Gln Lys Gly Glu Gln Gly Thr Val Ala Cys Thr
130                 135                 140

Trp Glu Arg Gly Arg Asp Thr His Leu Tyr Thr Glu Tyr Thr Leu Gln
145                 150                 155                 160

Leu Ser Gly Pro Lys Asn Leu Thr Trp Gln Lys Gln Cys Lys Asp Ile
                165                 170                 175

Tyr Cys Asp Tyr Leu Asp Phe Gly Ile Asn Leu Thr Pro Glu Ser Pro
            180                 185                 190

Glu Ser Asn Phe Thr Ala Lys Val Thr Ala Val Asn Ser Leu Gly Ser
    195                 200                 205

Ser Ser Ser Leu Pro Ser Thr Phe Thr Phe Leu Asp Ile Val Arg Pro
210                 215                 220

Leu Pro Pro Trp Asp Ile Arg Ile Lys Phe Gln Lys Ala Ser Val Ser
225                 230                 235                 240

Arg Cys Thr Leu Tyr Trp Arg Asp Glu Gly Leu Val Leu Leu Asn Arg
                245                 250                 255

Leu Arg Tyr Arg Pro Ser Asn Ser Arg Leu Trp Asn Met Val Asn Val
            260                 265                 270

Thr Lys Ala Lys Gly Arg His Asp Leu Leu Asp Leu Lys Pro Phe Thr
    275                 280                 285
```

-continued

```
Glu Tyr Glu Phe Gln Ile Ser Ser Lys Leu His Leu Tyr Lys Gly Ser
290                 295                 300

Trp Ser Asp Trp Ser Glu Ser Leu Arg Ala Gln Thr Pro Glu Glu
305                 310                 315                 320

Pro Thr Gly Met Leu Asp Val Trp Tyr Met Lys Arg His Ile Asp Tyr
                325                 330                 335

Ser Arg Gln Gln Ile Ser Leu Phe Trp Lys Asn Leu Ser Val Ser Glu
                340                 345                 350

Ala Arg Gly Lys Ile Leu His Tyr Gln Val Thr Leu Gln Glu Leu Thr
            355                 360                 365

Gly Gly Lys Ala Met Thr Gln Asn Ile Thr Gly His Thr Ser Trp Thr
370                 375                 380

Thr Val Ile Pro Arg Thr Gly Asn Trp Ala Val Ala Val Ser Ala Ala
385                 390                 395                 400

Asn Ser Lys Gly Ser Ser Leu Pro Thr Arg Ile Asn Ile Met Asn Leu
                405                 410                 415

Cys Glu Ala Gly Leu Leu Ala Pro Arg Gln Val Ser Ala Asn Ser Glu
                420                 425                 430

Gly Met Asp Asn Ile Leu Val Thr Trp Gln Pro Pro Arg Lys Asp Pro
            435                 440                 445

Ser Ala Val Gln Glu Tyr Val Val Glu Trp Arg Glu Leu His Pro Gly
450                 455                 460

Gly Asp Thr Gln Val Pro Leu Asn Trp Leu Arg Ser Arg Pro Tyr Asn
465                 470                 475                 480

Val Ser Ala Leu Ile Ser Glu Asn Ile Lys Ser Tyr Ile Cys Tyr Glu
                485                 490                 495

Ile Arg Val Tyr Ala Leu Ser Gly Asp Gln Gly Gly Cys Ser Ser Ile
            500                 505                 510

Leu Gly Asn Ser Lys His Lys Ala Pro Leu Ser Gly Pro His Ile Asn
            515                 520                 525

Ala Ile Thr Glu Glu Lys Gly Ser Ile Leu Ile Ser Trp Asn Ser Ile
530                 535                 540

Pro Val Gln Glu Gln Met Gly Cys Leu Leu His Tyr Arg Ile Tyr Trp
545                 550                 555                 560

Lys Glu Arg Asp Ser Asn Ser Gln Pro Gln Leu Cys Glu Ile Pro Tyr
                565                 570                 575

Arg Val Ser Gln Asn Ser His Pro Ile Asn Ser Leu Gln Pro Arg Val
            580                 585                 590

Thr Tyr Val Leu Trp Met Thr Ala Leu Thr Ala Ala Gly Glu Ser Ser
            595                 600                 605

His Gly Asn Glu Arg Glu Phe Cys Leu Gln Gly Lys Ala Asn Trp Met
610                 615                 620

Ala Phe Val Ala Pro Ser Ile Cys Ile Ala Ile Ile Met Val Gly Ile
625                 630                 635                 640

Phe Ser Thr His Tyr Phe Gln Gln Lys Val Phe Val Leu Leu Ala Ala
                645                 650                 655

Leu Arg Pro Gln Trp Cys Ser Arg Glu Ile Pro Asp Pro Ala Asn Ser
                660                 665                 670

Thr Cys Ala Lys Lys Tyr Pro Ile Ala Glu Glu Lys Thr Gln Leu Pro
            675                 680                 685

Leu Asp Arg Leu Leu Ile Asp Trp Pro Thr Pro Glu Asp Pro Glu Pro
690                 695                 700

Leu Val Ile Ser Glu Val Leu His Gln Val Thr Pro Val Phe Arg His
```

-continued

```
        705                 710                 715                 720
    Pro Pro Cys Ser Asn Trp Pro Gln Arg Glu Lys Gly Ile Gln Gly His
                    725                 730                 735

Gln Ala Ser Glu Lys Asp Met Met His Ser Ala Ser Ser Pro Pro Pro
                    740             745                 750

Pro Arg Ala Leu Gln Ala Glu Ser Arg Gln Leu Val Asp Leu Tyr Lys
            755                 760                 765

Val Leu Glu Ser Arg Gly Ser Asp Pro Lys Pro Glu Asn Pro Ala Cys
            770                 775                 780

Pro Trp Thr Val Leu Pro Ala Gly Asp Leu Pro Thr His Asp Gly Tyr
    785                 790                 795                 800

Leu Pro Ser Asn Ile Asp Asp Leu Pro Ser His Glu Ala Pro Leu Ala
                    805                 810                 815

Asp Ser Leu Glu Glu Leu Glu Pro Gln His Ile Ser Leu Ser Val Phe
                820                 825                 830

Pro Ser Ser Ser Leu His Pro Leu Thr Phe Ser Cys Gly Asp Lys Leu
                835                 840                 845

Thr Leu Asp Gln Leu Lys Met Arg Cys Asp Ser Leu Met Leu
        850                 855                 860
```

USES OF IL-12 AND THE IL-12 RECEPTOR POSITIVE CELL IN TISSUE REPAIR AND REGENERATION

CROSS-REFERENCE TO RELATED APPLICATIONS

This application claims priority to U.S. Provisional Application Ser. No. 61/387,419, filed Sep. 28, 2010, U.S. Provisional Application Ser. No. 61/405,584, filed Oct. 21, 2010, U.S. Provisional Application Ser. No. 61/409,407, filed Nov. 2, 2010, and U.S. Provisional Application Ser. No. 61/477,130, filed Apr. 19, 2011, each of which are incorporated herein by reference in their entirety, including all figures and tables.

STATEMENT REGARDING FEDERALLY SPONSORED RESEARCH OR DEVELOPMENT

This invention was made with U.S. Government support under contract number BAA-BARDA-08-08 awarded by the Biomedical Advanced Research and Development Authority, with the Department of Health and Human Services. The Government has certain rights in the invention.

BACKGROUND

Hematopoiesis is sustained by a rare population of hematopoietic stem cells (HSCs) capable of self-renewal and differentiation into multiple hematopoietic lineages. These HSCs include a long-term repopulating (LTR) subset that is capable of complete hematopoietic regeneration. The ability to maintain or expand the LTR population of hematopoietic stem cells in vitro and in vivo without inducing their differentiation is crucial for clinical applications, such as gene therapy and the expansion of stem cells and progenitor cells for transplantation.

During the last decade, considerable progress has been made towards the isolation and characterization of primitive hematopoietic cell populations in mice and humans. From this body of work, several hematopoietic stem cell identifiers, i.e., cell-surface markers found on hematopoietic stem cells, have been delineated which have proven to be highly useful for the identification and isolation of hematopoietic stem cells. Novel identifiers of hematopoietic, long-term repopulating cells remain of interest, as the identification of novel stem cell markers may provide access to previously unknown subsets of rare hematopoietic stem cells.

Despite the number of cell surface markers that have been delineated to date, the identification and uses of rare populations of hematopoietic stem cells capable of tissue repair and regeneration remains uncharted territory. Rare stem cell populations that are related to lethal radiation survival in animal models might prove to be useful in the therapeutic areas of repair and regeneration of hematopoiesis and also other tissues types within the body, such as brain tissue, lung tissue, kidney tissue, pancreatic tissue, liver tissue, or cardiac tissue and the like. Thus, the identification of novel stem cell markers that can delineate a rare population of stem cells useful in hematopoietic tissue repair and regeneration, as well as general tissue repair and regeneration, are still needed in the areas of regenerative medicine.

SUMMARY OF INVENTION

In one embodiment, the present invention relates to a cell population comprising a substantially homogenous population of cells that expresses the IL-12 receptor and the cell marker CD34 and that has been exposed to exogenous IL-12 ligand. In another embodiment, the cell population is of human origin. For example, the cells can have been isolated before being exposed to exogenous IL-12 ligand. Alternatively, the cells can have been exposed to exogenous IL-12 ligand while in a subject, and then isolated. Also encompassed by the invention is a population of blood cells differentiated from a cell population of the invention.

In one embodiment, the cell population of the invention can further express the marker CDCP1, the marker c-kit, the marker KDR, the marker Flt3, the marker SLAM, the marker CD133, the marker IFNGR (Interferon-γ receptor), the absence of CD34 as a marker, or any combination thereof.

In yet another embodiment, the stem cell present in the cell population of the invention does not express at least one or more major histocompatibility (MHC) class I and class II molecules.

In one embodiment, the cell population of the invention undergoes expansion in the presence of IL-12 heterodimer ligand. In another embodiment, the cell population of the invention comprises long-term repopulating (LTR) hematopoietic stem cells. In yet another embodiment, the cell population of the invention is radioresistant.

In one embodiment, the source of the cell population of the invention is bone marrow. In another embodiment, the source of the cell population of the invention is peripheral blood. In yet another embodiment, the source of the cell population of the invention is the spleen. In another embodiment, the source of the cell population of the invention is blood from an umbilical cord.

In one embodiment, for the cell population of the invention the IL-12 receptor comprises the beta 2 subunit of the IL-12 receptor.

The invention also encompasses methods for generating a cellular transplant for repair of cells and tissue. Such a method can comprise, for example, (a) isolating a cell population that expresses the IL-12 receptor and CD34; and (b) exposing the cell population to exogenous IL-12. The method can further comprise a step where the population of cells expressing the IL-12 receptor is isolated using an antibody that binds the beta 2 subunit of the IL-12 receptor.

The invention further encompasses methods for repairing cells and tissue in a subject. Such a method can comprise (a) isolating a cell population that expresses the IL-12 receptor; (b) exposing the cell population to exogenous IL-12.; and (c) administering the cell population to a subject. In such a method, the cell population can be isolated using an antibody that binds the beta 2 subunit of the IL-12 receptor. In addition, the method can further comprise administering IL-12 ligand to the subject following administration of the cell population. In yet another embodiment, the method encompasses treating a subject with diabetes. Alternatively or in addition, the subject can have one or more blood cell counts that are below normal range due to the effects of radiation therapy or chemotherapy. In yet another embodiment, the method encompasses administering the cell population to an organ selected from the group consisting of kidney, liver, lung, spleen, pancreas, and cardiac tissue.

The cell population to be administered to a subject in the methods of the invention can include one or more pharmaceutically acceptable excipients.

The invention further encompasses cell populations derived from differentiated tissues that express the IL-12 receptor. For example, cell populations derived from neuronal tissue comprising a substantially homogenous population of cells that expresses the IL-12 receptor and that has been exposed to exogenous IL-12 ligand. The cell populations may also be derived from kidney tissue, uterine tissue, stomach tissue, intestinal tissue, appendix tissue, or testis tissue.

The invention further encompasses methods of regenerating various types of tissue of a subject in vivo following administration of IL-12 ligand to the subject, wherein the IL-12 ligand binds to the IL-12 receptor on a population of cells in the tissue to yield an increase in the number IL-12 receptor positive stem cells in that tissue. In some embodiments, the type of tissue may be neuronal tissue, kidney tissue, uterine tissue, stomach tissue, or intestinal tissue. In some eIn some embodiments, the tissue is neuronal tissue and a route IL-12 administration is selected from the group consisting of epidural, peridural, intracerebral, intrathecal, and intracerebroventricular. In some embodiments, the tissue is kidney tissue. In some embodiments, the tissue is uterine tissue. In some embodiments, the administration of IL-12 is intrauterine. In some embodiments, the tissue is stomach tissue. In some embodiments, the tissue is intestinal tissue. In some embodiments, the IL-12 administration is enteral. In some of the foregoing embodiments, the route of IL-12 administration can be subcutaneous, intravenous, intraarterial, intramuscular or intraperitoneal.

The foregoing general description and following brief description of the drawings and the detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE DRAWINGS

FIGS. 2A-2C are for mice receiving lethal irradiation (10 Gy), FIGS. 2D-2F are for mice receiving sublethal irradiation (5 Gy). The Y axis indicates the percentage change of the cell count for each blood cell subtype after radiation in relative to its baseline blood cell count before radiation. (*: $p<0.05$; **: $p<0.01$, Error bars represents S.E.M.). Arrow indicates the time of radiation. 0 day means the day of radiation. Bg: background.

FIG. 4A shows a bar graph of Ly5.1 mouse survival following transplantation of Ly5.2 bone marrow cells in a repopulation assay, while FIG. 4B shows a bar graph for results of a CFU-$S_{12}$ assay of spleens from mice that received transplanted cells. FIG. 4C shows a graph of data from a colony-forming cells assay on bone marrow cells from Ly5.1 mice treated with IL-12 twenty four hours before irradiation. FIG. 4D shows a graph representing cell counts of Ly5.2 cells that have repopulated a Ly5.1 animal receiving an Ly5.2 bone marrow transplant. FIG. 4E shows a representative plot of flow cytometry data for a subpopulation of myeloid cells in a population of transplanted bone marrow cells. FIG. 4F shows a representative plot of flow cytometry data for a subpopulation of myeloid cells in a population of transplanted bone marrow cells.

FIGS. 6A and 6B are photomicrographs of IL-12Rβ2 expression in human and rhesus intestinal crypts. FIG. 6A shows representative IL-12Rβ2 expression on intestinal stem cells (circled). FIG. 6B shows IL-12Rβ2 expression on intestinal stem cells (circled) and paneth cells (arrows).

FIGS. 7A and 7B are photomicrographs of expression of IL-12Rβ2 in normal salivary gland of a human. IL-12Rβ2 is predominately expressed in salivary secretory acini (AC) of the salivary gland. IL-12Rβ2 expression is also represented in striated excretory ducts (ED) of the salivary gland.

FIG. 9 is a series of photomicrographs of femoral bone marrow stained for IL-12Rβ2 and Sca-1, or IL-12Rβ2 and osteocalcin, as described in Example 8.

FIG. 18 shows plots of flow cytometry data (forward scatter and side scatter) for human lineage marker-depleted stem cells, as described in Example 13. FIGS. 18A and 18B are from two different donor subjects.

FIG. 19A is a Kaplan-Meier survival plot of control, IL-12-treated, and bone marrow transplant treated mice. FIG. 19B-D are graphs showing blood cell counts from the treated and control groups at various time points following irradiation. The dashed line represents the cutoff point for a cell count in a healthy mouse. FIG. 19B shows the counts for neutrophils, FIG. 19C shows the counts for red blood cells, and FIG. 19D shows the counts for platelets.

FIG. 20B, treated).

DETAILED DESCRIPTION OF THE INVENTION

The present invention is directed to the identification, isolation and characterization of rare, survival-related stem cells delineated by a previously unknown stem cell marker and its associated ligand. The novel stem cell marker of the invention is the Interleukin-12 receptor (IL-12R) and the ligand is Interleukin-12 (IL-12). The novel stem cell of the invention, which is marked by the IL-12 receptor, with or without the use of its associated ligand can be used, for example, for repair and regeneration of various tissue types, including blood, bone marrow, as well as cardiac, brain, pancreatic, renal or liver tissue or the like.

Figure 1:
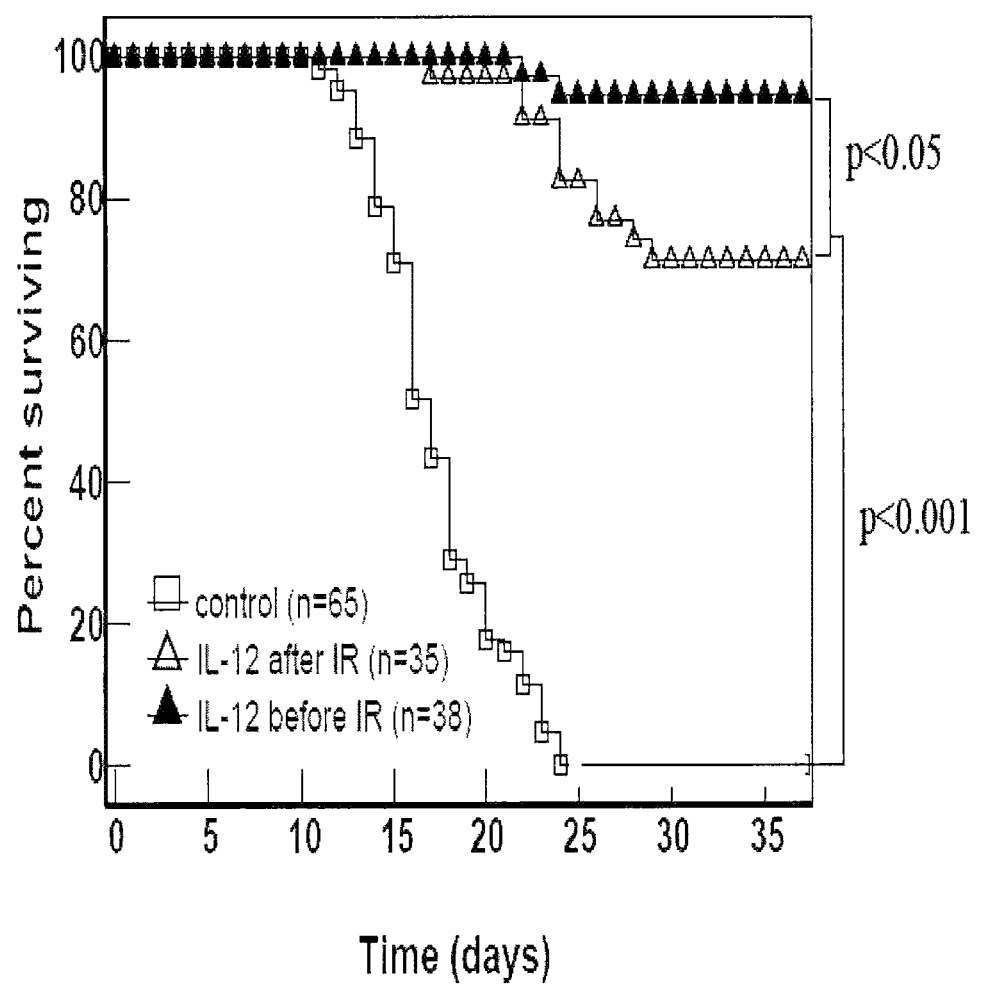
FIG. 1 shows a Kaplan-Meier plot of survival data for irradiated mice receiving a low dose of IL-12, as described in Example 1. Mice were treated intravenously with rMuIL-12 (100 ng/mouse, about 5 µg/kg) at 24 hours before (▲) or 1 hour after (Δ) lethal irradiation (10 Gy). Control group mice (□) were injected with the same volume of phosphate buffered saline. The p value was calculated using Log Rank Test (IL-12 treatment versus control, $p<0.001$; IL-12-treated before IR versus after IR, $p<0.05$).

The ligand Interleukin-12 (IL-12) is well-known for its immunoregulatory properties working at the level of differentiated, mature hematopoietic cells, such as natural killer cells and other T-cells. A significant body of work has demonstrated that IL-12 is a potent immuno-modulator with significant anti-tumorigenic and anti-angiogenic properties. IL-12, however, is generally not known to play a role in hematopoiesis at the level of hematopoietic stem cells (HSC). Based on the fact that Interleukin-12 (IL-12) can uniquely confer survival to lethally irradiated mice, as shown in FIG. 1, a hypothesis was generated which yielded the present invention. In accordance with the invention, a responsive IL-12 receptor positive stem cell (IL-12R$^+$) exists in the body that can be activated by the IL-12 ligand. Further, the IL-12R$^+$ stem cell of the present invention possesses significant survival related properties that are involved in the repair and regeneration of tissue.

Herein is provided evidence that the IL-12R$^+$ stem cell is involved in hematopoietic stem cell survival and expansion. Evidence is provided herein that merely one, low dose of IL-12 to mice, either shortly before or after the administration of a lethal dose of radiation, produces the following properties:

- IL-12 confers significant survival to lethally irradiated mice by generating multilineage, hematopoietic recovery following lethal radiation. No single cytokine can confer survival to lethally irradiated animals when administered as one parenteral dose that can be administered either before or after a lethal dose of radiation.
- IL-12 administration leads to an increase in bone marrow cellularity and expansion of certain hematopoietic/progenitor stem cells
- Donor hematopoietic cells derived from mice rescued from the deleterious effects of lethal radiation via IL-12 administration are capable of repopulating secondarily lethally irradiated murine recipients.

These novel and unexpected findings suggest that the IL-12 ligand acting on an IL-12R$^+$ stem cell have a significant and previously unrecognized role in hematopoietic stem cell survival and in vivo stem cell expansion. Thus, the present invention includes isolating and utilizing the IL-12-responsive hematopoietic "survival" stem cell for use in hematopoietic stem cell applications, such as ex vivo hematopoietic stem cell expansion and differentiation, as well as repair and regeneration of various tissues, such as bone marrow, cardiac, lung, brain, pancreatic, kidney or liver tissue or the like. Thus, the invention yields a rare subset of hematopoietic stem cells with high proliferative, repopulating, repair and regeneration potential. This primitive and survival-conferring stem cell population may also be useful in ex-vivo hematopoietic stem cell expansion and differentiation into mature blood cells, including white blood cells, red blood cells and platelets.

The isolation of the human, IL-12 responsive, survival-conferring stem cells, either with or without the use of the IL-12 ligand, can be used commercially, for example, (1) to generate highly reparative and regenerative, cellular transplants, and (2) to generate in vivo and ex vivo expanded hematopoietic stem cell populations, including differentiated blood cells produced from the expanded HSC, and various other applications as described herein. In this regard, a corresponding antibody IL-12R can be generated to the human IL-12R⁺ stem cell.

A. Definitions

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used in this disclosure, except where the context requires otherwise, the term "comprise" and variations of the term, such as "comprising," "comprises" and "comprised" are not intended to exclude other additives, components, integers or steps.

The term "expansion" is defined herein as an increase in the number of cells in a cell population.

The term "hematopoietic stem cell" or "HSC" as used herein refers to a population of stem cells derived from a population of blood cells that can differentiate into multiple types of cells.

The term "IL-12 heterodimer ligand" is defined herein as a heterodimeric, soluble protein (also known as IL-12R P70) that specifically binds to and activates the IL-12 receptor where the IL-12 receptor is a membrane-bound cellular protein. The IL-12 heterodimer ligand has a p35 subunit (SEQ ID NO: 1; GenBank Accession Number NP_000873) and a p40 subunit (SEQ ID NO: 2; GenBank Accession Number NP_002178) which, after removal of signal sequence peptides, combine to form a heterodimer. In accordance with the present invention, the IL-12 heterodimer ligand may or may not be glycosylated. Also in the present invention the IL-12 heterodimer ligand binds to the IL-12 receptor expressed on a stem cell. The preferred amino acid sequence for the IL-12 heterodimer ligand is as follows, but variant forms containing polymorphisms are in accordance with the present invention.

```
IL-12 Ligand p35 Subunit [SEQ ID NO: 1]:
  1 rnlpvatpdp gmfpclhhsq nllraysnml qkarqtlefy pctseeidhe 61 ditkdktstv eaclpleltk nesclnsret sfitngscla srktsfmmal 111 clssiyedlk myqvefktmn akllmdpkrq ifldqnmlav idelmqalnf 161 nsetvpqkss leepdfyktk iklcillhaf riravtidry msylnas IL-12 Ligand p40 Subunit [SEQ ID NO: 2]:
  1 iwelkkdvyv veldwypdap gemvvltcdt peedgitwtl dqssevlgsg
```

-continued
```
 61 ktltiqvkef gdagqytchk ggevlshsll llhkkedgiw stdilkdqke 111 pknktflrce aknysgrftc wwlttistdl tfsvkssrgs sdpqgvtcga 161 atlsaervrg dnkeyeysve cqedsacpaa eeslpievmv davhklkyen 211 ytssffirdi ikpdppknlq lkplknsrqv evsweypdtw stphsyfslt 261 fcvqvqgksk rekkdrvftd ktsatvicrk nasisvraqd ryyssswsew 311 asvpcs
```

The term "IL-12 homodimer ligand" is defined herein as a soluble, dimeric protein comprising two p40 subunits (see SEQ ID NO: 2) to form the homodimer. The IL-12 homodimer may or may not be glycosylated. The IL-12 homodimer also binds to the IL-12 receptor. In the present invention, the IL-12 homodimer can bind to and further activate or modify the activity of the IL-12 ligand/IL-12 receptor complex bound to the surface of the IL-12 stem cell. In the invention, the IL-12 homodimer may be administered to a patient or donor exogenously. Although sequence variation may be tolerable to the limits of the present invention, the preferred sequence for each monomer of the IL-12 homodimer is that of SEQ ID NO: 2.

The term "IL-12 monomer ligand" is defined as protein comprising the p40 subunit of the IL-12 ligand (SEQ ID NO: 2). The IL-12 monomer may or may not be glycosylated. The IL-12 monomer also binds to the IL-12 receptor. In the invention, the IL-12 monomer may be administered to a patient or donor exogenously. In the present invention, the IL-12 monomer can bind to and further activate or modify the activity of the IL-12 ligand/IL-12 receptor complex bound to the surface of the IL-12 stem cell.

The term "IL-12 receptor" is defined herein as a heterodimeric, membrane-bound receptor for the IL-12 ligand. The IL-12 receptor heterodimer subunits are beta 1 (β1) and beta 2 (β2). In accordance with the present invention, the IL-12 receptor may also bind the IL-12 homodimer and the IL-12 monomer, as defined herein, to form a multimer complex comprising the IL-12 ligand/IL-12 receptor pair and the homodimer and/or the monomer. In the present invention, the multimer complex would further activate the IL-12 ligand/IL-12 receptor pair or may modify the activity of the ligand/receptor pair. In accordance with the present invention, the IL-12 receptor protein is defined to be in its endogenous state as isolated from the IL-12 selected stem cell taken from a donor or a patient. As such, the IL-12 receptor may contain polymorphisms distinct from the canonical amino acid sequence of the β1 (SEQ ID NO: 3; from GenBank Accession Number NP_005526) and β2 subunits (SEQ ID NO: 4; from GenBank Accession Number NP_001550), as described below:

IL-12 receptor (beta 1) [SEQ ID NO: 3]:
```
  1 meplvtwvvp llflfllsrq gaacrtsecc fqdppypdad sgsasgprdl rcyrissdry 61 ecswqyegpt agvshflrcc lssgrccyfa agsatrlqfs dqagvsvlyt vtlwveswar 121 nqtekspevt lqlynsvkye pplgdikvsk lagqlrmewe tpdnqvgaev qfrhrtpssp 181 wklgdcgpqd ddtescicpl emnvagefql rrrqlgsqgs swskwsspvc vppenppqpq 241 vrfsveqlgq dgrrrltlke qptqlelpeg cqglapgtev tyrlqlhmls cpckakatrt 301 lhlgkmpyls gaaynvavis snqfgpglnq twhipadtht epvalnisvg tngttmywpa 361 raqsmtycie wqpvgqdggl atcsltapqd pdpagmatys wsresgamgq ekcyyitifa 421 sahpekltlw stvlstyhfg gnasaagtph hvsvknhsld sysvdwapsl lstcpgvlke 481 yvvrcrdeds kqvsehpvqp tetqvtlsgl ragvaytvqv radtawlrgv wsqpqrfsie 541 vqvsdwliff aslgsflsil lvgvlgylgl nraarhlcpp lptpcassai efpggketwq 601 winpvdfqee aslgealvve mswdkgerte plektelpeg apelaldtel sledgdrcka 661 km
```

IL-12 receptor (beta 2) [SEQ ID NO: 4]:
```
  1 mahtfrgcsl afmfiitwll ikakidackr gdvtvkpshv illgstvnit cslkprqgcf 61 hysrrnklil ykfdrrinfh hghslnsqvt glplgttlfv cklacinsde iqicgaeifv 121 gvapeqpqnl sciqkgeqgt vactwergrd thlyteytlq lsgpknitwq kqckdiycdy 181 ldfginitpe spesnftakv tavnslgsss slpstftfld ivrplppwdi rikfqkasys 241 rctlywrdeg lvllnrlryr psnsrlwnmv nvtkakgrhd lldlkpftey efqissklhl 301 ykgswsdwse slraqtpeee ptgmldvwym krhidysrqq islfwknlsv seargkilhy 361 qvtlqeltgg kamtqnitgh tswttviprt gnwavaysaa nskgsslptr inimnlceag 421 llaprqvsan segmdnilvt wqpprkdpsa vqeyvvewre lhpggdtqvp lnwlrsrpyn 481 vsalisenik syicyeirvy alsgdqggcs silgnskhka plsgphinai teekgsilis 541 wnsipvqeqm gcllhyriyw kerdsnsqpq lceipyrvsq nshpinslqp rvtyvlwmta 601 ltaagesshg nerefclqgk anwmafvaps iciaiimvgi fsthyfqqkv fvllaalrpq 661 wcsreipdpa nstcakkypi aeektqlpld rllidwptpe dpeplvisev lhqvtpvfrh 721 ppcsnwpqre kgiqghqase kdmmhsassp pppralqaes rqlvdlykvl esrgsdpkpe 781 npacpwtvlp agdlpthdgy lpsniddlps heapladsle elepqhisls vfpssslhpl 841 tfscgdkltl dqlkmrcdsl ml
```

The term "IL-12 antibody" is defined herein as antibody that binds to one or more epitopes to the Il-12 beta 2 receptor subunit or the complex of the IL-12 beta 1/IL-12 beta 2 subunits.

The term "IL-12 stem cell" is defined herein as an isolated cell derived from a population of blood cells that does not express lineage markers, i.e., an immature cell, and expresses the IL-12 receptor. The IL-12 stem cell will comprise other membrane-bound surface markers. The preferred source of the isolated IL-12 stem cell is human bone marrow, but other blood sources are suitable to the present invention. These are human cells derived from peripheral blood, blood cells derived from spleen, and cord blood. In accordance with the present invention, the IL-12 stem cell is activated by the IL-12 ligand. Also in accordance with the invention, activation by the IL-12 ligand can be further modified by the presence of the IL-12 homodimer or monomer interacting with the IL-12 ligand/IL-12 receptor pair.

The term "IL-12 stem cell transplant" is defined herein as a population of cells comprising the IL-12 stem cell as defined herein. In accordance with the invention, this population of cells may comprise other cells as carrier cells. The choice of carrier cells will depend on the target tissue that will receive the transplant. For example, if the target tissue is the bone marrow compartment, then the carrier cells will generally be a population of blood cells. If the target tissue is other than bone marrow, the carrier cells may be derived from the targeted recipient organ or may be blood cells. In the invention the IL-12 stem cell is derived from a population of immature blood cells.

The term "lineage deficient" or "Lin⁻" describes cells that lack certain markers, indicating that the cells are not committed to producing a particular cell type lineage. For example, hematopoietic stem cells are lineage deficient when they lack the markers CD3e, CD4, CD5, CD8b, CD8a, B220, CD11b, Grl and Ter.

As used herein, "pluripotent stem cell" means a stem cell that can differentiated into two or more differentiated cell types. For example, differentiated cell types can include blood cells, neural cells, endothelial cells, cardiac cells, pancreatic cells, kidney cells, liver cells, spleen cells and lung cells.

The term "population of cells" is defined herein as a collection of cells comprising the IL-12 stem cell as defined herein.

The phrase "repair and regeneration of diseased organs" is defined herein as some measurable or quantifiable increase in the health of the targeted recipient organ. Repair and regeneration of diseased organs can involve, but is not limited to, transdifferentiation of the IL-12 stem cell or carrier cells into cells related to the targeted recipient organ where the targeted recipient organ is other than bone marrow tissue or blood tissue.

The term "short-term repopulating hematopoietic stem cells" (STR HSC) is defined herein as hematopoietic stem cells that are capable supporting hematopoiesis for no more than 15 weeks. STR HSC can have a cell marker profile of: $CD34^+$, $SCA-1^+$, $Thy1.1^{+/lo}$, $C-kit^+$, $Lin^-$, $CD135^-$, $Slamf1/CD150^+$, $Mac-1 (CD11b)^{lo}$.

The term "long term repopulating hematopoietic stem cells" (LTR HSC) is defined herein as hematopoietic stem cells that are capable of supporting hematopoiesis in an animal for 6 months or longer. LTR HSC can have different cell marker profiles depending on the animal species from which they are derived. For example, mouse LTR HSC have a cell marker profile of: $CD34^-$, $SCA-1^+$, $Thy1.1^{+/lo}$, $C-kit^+$, $Lin^-$, $Slamf1/CD150^+$, $CD135^-$.

As used herein "a substantially homogenous cell population" refers to a population or sample of cells which contain a majority (i.e., at least 50%) of cells having the trait(s) of interest. In preferred embodiments, substantially homogenous populations contain at least 60%, at least 70%, at least 80%, at least 90% or more of the cells having the trait(s) of interest.

The term "therapeutically effective amount or dose" is defined herein as a dose of a substance that produces effects for which it is administered. For example, a dose of IL-12 sufficient for increasing survival and/or preserving bone marrow function, and/or promoting hematopoietic recovery or restoration in a subject following myeloablation, radiation therapy, and/or chemotherapy. The exact dose of IL-12 will depend on the purpose of the treatment, the timing of administration of IL-12, certain characteristics of the subject to be treated, the total amount or timing of myeloablation, radiation therapy, and/or chemotherapy, and is ascertainable by one skilled in the art using known techniques (see, e.g., Lieberman, Pharmaceutical Dosage Forms (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20$^{th}$ Edition, 2003, Gennaro, Ed., Lippincott, Williams & Wilkins).

Generally, a dose of a therapeutic agent, according to the methods and compositions of the present invention, can be expressed in terms of the total amount of drug to be administered, (i.e. ng, g, or mg). Preferably, the dose can be expressed as a ratio of drug to be administered to weight or surface area of subject receiving the administration (i.e., ng/kg, g/kg, $ng/m^2$, or $g/m^2$). When referring to a dose in terms of the mass to be administered per mass of subject (i.e., ng/kg), it will be understood that doses are not equivalent between different animals, and thus conversion factors will need to be used to ensure that one animal receives the same dose equivalent as another animal. Suitable factors for the conversion of a mouse "dose equivalent" to a "dose equivalent" of a different animal are given in Table 1 below.

TABLE 1

Conversion Factors and Equivalent Doses for Several Animals

| Species | Weight (kg) | Total Dose (ng/kg) | Dose (ng/kg) | Dose (ng/m²) | Conversion Factor |
|---|---|---|---|---|---|
| Human | 65 | 25655.82 | 394.7 | 15,000 | 0.0794 |
| Mouse | 0.02 | 99.47 | 4973.44 | 15,000 | 1.0000 |
| Hamster | 0.03 | 130.2 | 4339.87 | 15,000 | 0.8726 |
| Rat | 0.15 | 381.12 | 2540.8 | 15,000 | 0.5109 |
| Guinea Pig | 1.00 | 1335 | 1335 | 15,000 | 0.2684 |
| Rabbit | 2.0 | 2381.1 | 1190.65 | 15,000 | 0.2394 |
| Cat | 2.5 | 2956.44 | 1182.57 | 15,000 | 0.2376 |
| Monkey | 3.0 | 3681.75 | 1227.25 | 15,000 | 0.2468 |
| Dog | 8.0 | 6720 | 840 | 15,000 | 0.1689 |

Thus, in one embodiment, doses are given in terms of mass to surface area (i.e., $ng/m^2$ or $g/m^2$), which are equivalent for all animals. The following basic conversion factors can be used to convert ng/kg to $ng/m^2$: mouse=3.0, hamster=4.1, rat=6.0, guinea pig=7.7, human=38.0 (*Cancer Chemother Repts.*, 50(40):219 (1966)).

The term "tissue committed stem cell" or "TCSC" is defined herein as a stem cell that is not fully differentiated, but can only differentiate into cells that make up a certain type of tissue, for example, liver cells or blood cells.

B. Stem Cells and Stem Cell Factors

Stem cells have been shown to possess vast therapeutic potential. (9) Thus, it is anticipated that advances in stem cells as therapeutics will have a tremendous impact on the clinical practice of medicine. The hematopoietic stem cell, the common ancestor of all types of blood cells, is the best-characterized stem cell in the body and the only stem cell that is clinically applied in the treatment of diseases that include malignancies such as leukemia, lymphomas, myeloma, pediatric neuroblastoma and sarcomas, as well as congenital immunodeficiencies and bone marrow failure (e.g., aplastic anemia).

New techniques involving multicolor cell sorting can enable the purification of hematopoietic stem cells and their downstream progenitors, such as common lymphoid progenitors and common myeloid progenitors (10,11). Recent genetic approaches, including gene chip technology, are useful in elucidating the gene expression profile of hematopoietic stem cells (12-14).

Another important aspect related to recent advances in hematopoietic stem cells as therapeutics is the discovery of hematopoietic stem cell factors, and their cognate receptors, that can be used to identify and regulate (activate) stem cells in vivo and in vitro. Such advances are propelling the therapeutic use of hematopoietic stem cells closer to fruition as treatment modalities for a host of diseases and disorders. Further, the availability of novel stem cell factors for the manipulation of hematopoietic stem cells may be the necessary link that renders populations of rare stem cells accessible to physicians and scientists for use in medicine and research.

The present invention is based on the discovery that Interleukin-12 (IL-12) can uniquely confer survival to lethally irradiated mice at low doses. These studies provided inferential evidence that IL-12 may be involved in hematopoietic stem cell survival and expansion. Just one low dose of IL-12 to mice, either shortly before or after the administration of a lethal dose or radiation, confers survival and multilineage, hematopoietic recovery to the lethally irradiated subject. Further, these effects originate in the protection and/or expansion of LTR HSC as evidenced by the ability of donor bone marrow cells from previously rescued mice to rescue a secondarily lethally irradiated recipient, as well as other data (See FIG. 2).

These novel and unexpected findings suggest that IL-12 has a significant and previously unrecognized role in hematopoietic stem cell survival and in vivo stem cell expansion. Thus, the invention involved the isolation and utilization of the corresponding IL-12R$^+$ stem cell, which has numerous applications in vivo and ex vivo.

C. Clinical Need for Ex vivo Expanded Hematopoietic Stem Cells

Cord blood (CB), peripheral blood (PB) or bone marrow (BM)-derived hematopoietic stem cells provide therapeutically efficacious sources of cells to treat a variety of hematological disorders (15,16), as well as for use in tissue repair and regeneration. Unfortunately, the low numbers of HSC isolated from a typical CB, PB or BM donation places limitations on these therapies (15,17). Effective HSC expansion represents an attractive solution to numerous clinical needs (18). However, this goal has remained elusive despite more than 20 years of experimentation in animal models and human clinical trials (19). Even the seemingly attainable goal of using culture-generated progenitors to shorten neutrophil and platelet recovery times in patients following myeloablative chemotherapy (20-22) has been generally ineffective (19).

The ability to successfully expand hematopoietic stem cells (HSC) in vivo and/or ex vivo would not only have a profound impact in the way that HSC transplantation is perceived, but could also expand the limits of tumor cell purging and somatic cell gene therapy (23-25), as well as be used as transplants for tissue repair and regeneration. The difficulties associated with inadequate numbers of HSC collected for transplantation from autologous or allogeneic sources, such as peripheral blood and bone marrow, or allogeneic umbilical cord blood would be largely eliminated. Moreover, if these difficulties are eliminated, human umbilical cord blood, which has limited use in adults because of an insufficient number of stem cells, might also become a reliable and attractive alternative to peripheral blood or bone marrow as a source of hematopoietic progenitors (23,26) for patients with malignant and nonmalignant conditions who lack traditional donors (27-29).

What might have been the deterrent to previous attempts at in vivo and/or ex vivo expansion of HSC? One obstacle that is solved by the present invention was the lack of a suitable stem cell population and activating ligand pair. In accordance with the present invention, the IL-12$^+$ stem cell and IL-12 ligand are capable of yielding expanding stem cell populations either in vivo or ex vivo.

Also in terms of ex vivo expansion, a recent study has revealed that the generation of mature blood cell populations (i.e., lin$^+$ cells) and their overall effects on culture microenvironment is the major limitation on the expansion of HSC in vitro (30). Madlambayan et al. (30) showed that the direct secretion of negative regulators by culture-generated lin$^+$ cells, and the indirect stimulation of cells to secrete negative regulators by culture-conditioned media, limits in vitro HSC generation. In the present invention, this same principle can be applied to in vivo expansion of stem cells. Thus, Madlambayan et al. developed a global culture manipulation (GCM) strategy to abrogate these effects and produce elevated numbers of LTC-ICs (14.6-fold relative to input), migrating rapid NOD/SCID repopulating cells (12.1-fold), and long-term NOD/SCID repopulating cells (5.2-fold) (30). This GCM approach appears to be a novel and generally useful approach with the capacity to generate expansion of hematopoietic stem cells leading to the production of mature blood cell populations. Thus in the present invention, this method, or similar methods, is used to generate ex vivo hematopoietic stem cell expansion via the utilization of isolated, IL-12 responsive, survival-conferring stem cells. The method of Madlambayan et al. is incorporated into the present application by reference in its entirety.

D. IL-12 is a Potent Immunomodulator

In all of the following description, any reference to the IL-12 ligand implies that there is a corresponding IL-12 receptor that is involved in the described effects.

Interleukin-12 (IL-12) is a heterodimeric pro-inflammatory cytokine that regulates the activity of cells involved in the immune response (31). It stimulates the production of interferon-$\gamma$ (IFN-$\gamma$) from natural killer (NK) cells and T cells (32-35), favors the differentiation of T helper 1 (TH 1) cells (36,37), and forms a link between innate resistance and adaptive immunity. IL-12 has also been shown to inhibit cancer growth via its immuno-modulatory and anti-angiogenesis effects (38-42). IL-12 is produced mainly by dendritic cells (DC) and phagocytes (macrophages and neutrophils), once they are activated by encountering pathogenic bacteria, fungi or intracellular parasites (43,44).

E. The IL-12/Interferon-$\gamma$ Feedback Loop and Inhibition of Hematopoiesis:

IL-12 and INF-$\gamma$ are involved in a feedback loop in vivo, where the production of IL-12 stimulates the production of INF-$\gamma$, which, in turn, enhances the production of IL-12. In in vitro systems, it has been reported that IL-12 can synergize with other cytokines (IL-3 and SCF) to stimulate the proliferation and differentiation of early hematopoietic progenitors (45-47). However, in contrast to the in vitro stimulation of early hematopoietic progenitors, in vivo administration of exogenous IL-12 has been shown to decrease peripheral blood cell counts and bone marrow hematopoiesis (48). Via the use of IFN-$\gamma$ receptor knockout mice, Eng et al. and Car et al. demonstrated that high dosages of IL-12 did not induce commonly seen toxicity effects, such as lymphopenia and inhibition of hematopoiesis (49,50). This observation suggests that the enhancement of bone marrow progenitors from IL-12 is balanced in vivo by the production of INF-$\gamma$, which acts in a dominant myelo-suppressive fashion.

F. The Role Of IL-12 in Hematopoietic Regeneration Following Lethal Radiation

Protection of the hematopoietic stem cell (HSC) compartment from the effects of lethal doses of radiation provides a model system to study the biology of stem cell regeneration. Neta et al. reported that IL-12 can protect bone marrow, but sensitizes the gastrointestinal (GI) system, when administrated 18 hours before radiation at a dose of 50 µg/kg (51). In these studies, the IL-12 treated mice died earlier than the control animals due to GI sensitization. Neta et al. also reported that the bone marrow protective effect of IL-12 could only be obtained if IL-12 is administered before radiation.

As described in Examples 1 and 2, a marked hematopoietic survival effect has been observed at a dose of 5 µg/kg (100 ng/mouse), which is 10 times lower than the dose in the Neta study, with no toxicity to the GI system. These results were obtained only when IL-12 was administered during a somewhat restricted time "window" in relation to the time of radiation (see Example 2). At sublethal doses of radiation (e.g., 500 rad), the data also indicate that administration of IL-12 attenuates the decrease in blood cell counts, i.e., increases blood cell counts (see Example 3). The GI toxicity observed by Neta et al. is correlated with the higher IL-12 dose used in Neta's studies. Also the decrease in blood cell counts observed in human Phase I and Phase II clinical trials of IL-12 as a cancer therapy may be due to the higher IL-12 doses, as well as repeated administration of the biologic.

IL-12 appears to be unique in its ability to effect survival of lethally irradiated mice. The magnitude of the lethal irradiation survival effect, the fact that survival is achieved even when IL-12 is administered after lethal radiation, the ability of IL-12 to effect lethal irradiation survival without the use of other cytokines, as well as the very low dose required for the lethal irradiation survival effect, appear to render IL-12 superior to the lethal radiation survival effect of other cytokines For example, Stem Cell Factor (SCF) can rescue 80% of lethally irradiated mice only when it is given to mice before lethal irradiation and only at a dose that is about 3 orders of magnitude greater than the survival dose of IL-12 used in our studies (52). Other studies report that lethal radiation rescue can be accomplished by administering growth factors up to 2 hours post radiation, but only with a complex combination of growth factors, namely SCF, TPO, IL-3, FLT-3 ligand and SDF-1 (53-54). Even the bi-functional Flt-3 ligand and G-GSF fusion agonist, referred to as progenipoietin-1, can achieve lethal radiation rescue only when administered 24 hours prior to radiation and at a dose that is three orders of magnitude higher than the dose of IL-12 used in our preliminary studies (55).

G. IL-12-Responsive Hematopoietic "Survival" Stem Cell Properties

The IL-12-responsive HSC is related to survival, and hence, this putative subset is referred herein as the "IL-12-responsive, hematopoietic survival stem cell." As such, this survival stem cell is a very primitive and a normally quiescent hematopoietic stem cell. (Under certain bodily stresses, however, such as radiation injury, or other stresses, such as chemotherapy or surgery, where the need for hematopoiesis, or other cellular functions, increase, these normally quiescent cells are activated by signals produced from dying cells, particularly blood cells.

Recently, the heterogeneity of bone marrow stem cells has come to the fore (56). Kucia et al. propose that bone marrow (BM) may harbor, in addition to hematopoietic stem cells (HSC), other rare versatile subpopulations of rare tissue-committed stem cells (TCSC), and perhaps, even more primitive pluripotent stem cells (PSC). Kucia et al. further propose that these primitive stem cells accumulate in bone marrow during ontogenesis where they find a permissive environment to survive. Looking from this perspective, marrow potentially could contain heterogeneous populations of stem cells at different levels of differentiation-beginning from early PSC to TCSC. These cells are referred to by Kucia et al. as a "reserve pool of mobile cells for tissue repair" that may be released from BM into peripheral blood after tissue injury to regenerate damaged organs. Thus, the IL-12-responsive, survival stem cell may be a TCSC or a PSC repair-related stem cell.

Moreover, the IL-12-responsive HSC subset is radioresistant. Experimental models have delineated the toxic effects of ionizing radiation on the hematopoietic stem cell compartment (57-60). A sublethal dose of only 500 cGy has been shown to eliminate 99% of the competent hematopoietic stem cells based upon their ability to repopulate a lethally irradiated secondary recipient (57). However, it has been proposed that a very small fraction of hematopoietic stem cells may be radioresistant (60-62). Heterogeneity of stem cell populations in the form of radioresistance has been demonstrated for intrathymic stem cells (63,61) and short term repopulating stem cells, namely CFU-S (57,60).

The IL-12-responsive HSC subset exhibits the properties of both a long-term repopulating (LTR) and a short-term repopulating (STR) HSC by possessing a faster self renewal kinetics profile. Some reports indicate that although the LTR HSC is the "true" stem cell, this stem cell is not capable of lethal radiation rescue when transplanted to secondary lethally irradiated hosts without the presence of (10,65). The phenomenon is generally attributed to the slow kinetics of self renewal of the "true" LTR HSC subset. However, it is possible that the IL-12-responsive subset possesses a faster kinetic self-renewal profile, leading to lethal radiation rescue in the absence of faster-acting, short-term repopulating (STR) HSC.

H. Function of "Survival" Stem Cells

The data indicate that the IL-12-responsive, survival-related, stem cells functions as long-term repopulating hematopoietic stem cells. The data further suggest that IL-12-responsive LTR HSC are expanded by the direct action of IL-12. An alternative explanation is that the IL-12-responsive HSC are actually short-term repopulating cells that confer survival, or support, to long-term repopulating cells. Another possible explanation would be that the IL-12 responsive cells are not hematopoietic stem cells, but are another stem cell type that confers survival to long-term repopulating HSC. Indeed, given any of these scenarios, the IL-12-responsive subpopulation is an important subset of survival-related stem cells that are invaluable in numerous clinical scenarios, including ex vivo expansion of HSC LTR.

The isolation of a primitive, quiescent, IL-12-responsive HSC is important in hematopoietic stem cell biology, having implications for hematopoietic diseases and cancer therapy. As mentioned above, as a survival-conferring stem cell subpopulation, the IL-12-responsive subpopulation may be responsible for repopulation of HSC under stresses, such as radiation injury, chemotherapy or surgery.

It has been reported that stem cells can be lured to the site of tumor formation via cytokines secreted by breast cancer, wherein the stem cells are utilized by the tumor to promote tumor growth (67). An intriguing scenario is that the IL-12-responsive, survival-conferring stem cells can also home to sites of tumor progression following activation by IL-12, but instead of promoting tumor growth, the IL-12 responsive stem cells promote tumor destruction. This hypothesis is expected to be borne out given the known anti-tumorigenic and anti-angiogenic properties of IL-12. In support of this notion, IL-12 is observed to be down regulated by cancer cells, which fosters an immunosuppressive environment for tumor proliferation (68,69). Further support for this notion is found in a report indicating that IL-12 can mobilize hematopoietic cells (70).

Finally, because the IL-12 responsive HSC subpopulation confers survival, and can be expanded in vivo with or without the stress of radiation injury, it is a very attractive HSC subpopulation for ex vivo HSC expansion. Thus, the use of the novel, IL-12-responsive HSC subpopulation can fill the clinical void for expanded HSC and their respective differentiated blood products.

Figure 2:
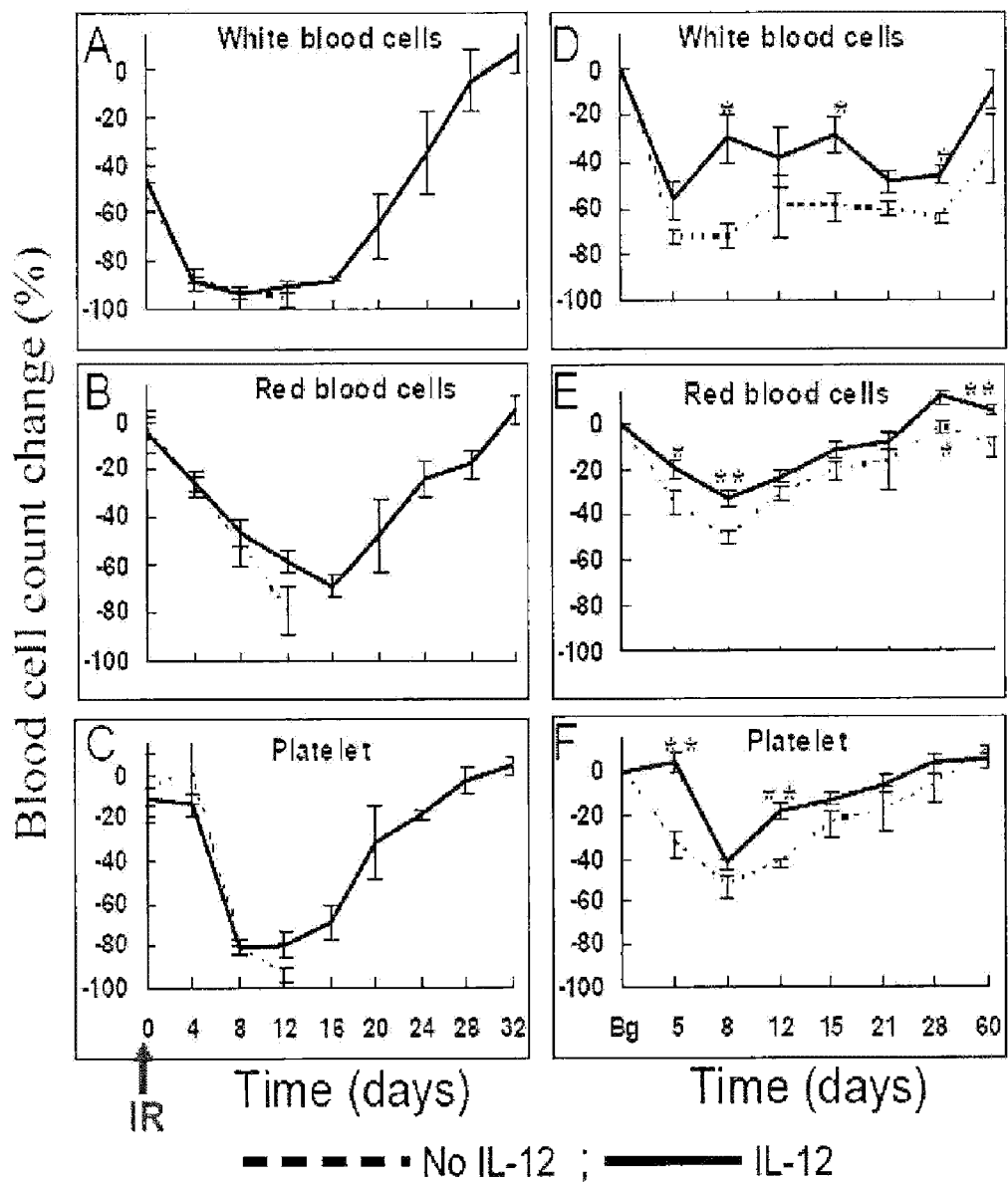
FIG. 2 shows graphs of peripheral blood cell counts from irradiated mice receiving IL-12, as described in Example 4.
Figure 4:
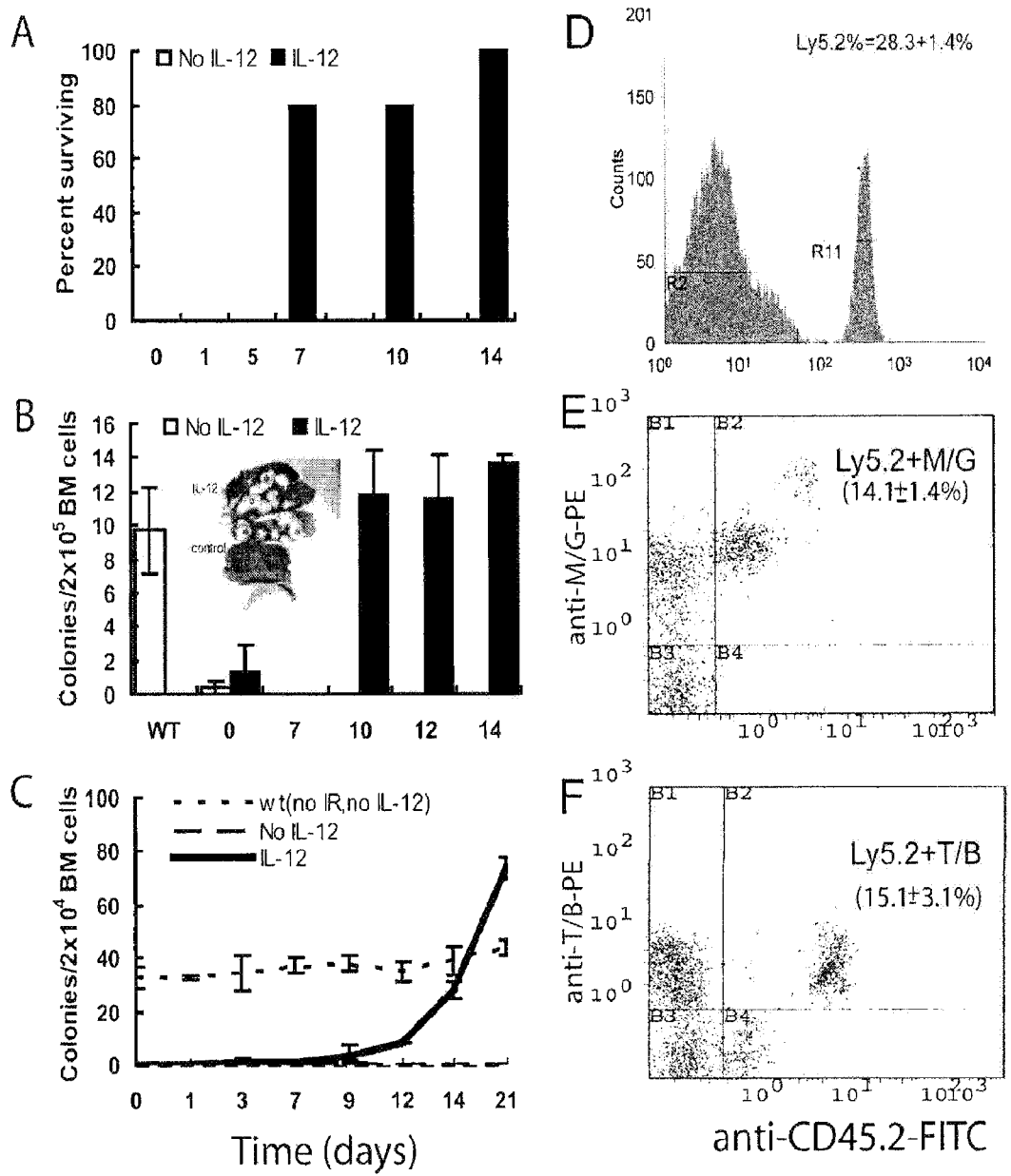
FIGS. 4A-4F show graphs of various assays on bone marrow cells from Ly5.2 mice treated with IL-12 twenty four hours before irradiation, as described in Example 5.

I. The IL-12/IL-12R System as a Master Regulator of Hematopoiesis:

The data presented herein show that the IL-12/IL-12R ligand and receptor system represents a master regulator of hematopoiesis involved in the regulation of survival-related mechanisms. First, on the functional level of the organism, the administration of exogenous IL-12 is shown to rescue mice from a lethal onslaught of radiation (FIG. 1). The fact that IL-12 can rescue mice from lethal irradiation with near equal effectiveness when administered either before or after radiation shows a direct effect of IL-12 on cells within the bone marrow (FIG. 1). In addition, the IL-12 facilitated lethal radiation rescue and results in complete reconstitution of all blood groups, i.e., white blood cells, red blood cells and platelets (FIG. 2). These data show that the IL-12 ligand acts at an IL-12 receptor on HSC. Second, the data also show that exogenous IL-12, administered at the time of lethal radiation, rescues long-term repopulating (LTR) HSC (FIG. 4). The data also show that administration of exogenous IL-12 increases the number of cells that do not express lineage markers (lineage negative cells; Lin⁻) but do express the IL-12 receptor (Lin⁻ IL-12R⁺ cells) as a cell surface marker. Lineage negative cells isolated from bone marrow largely comprise immature (undifferentiated) cells, containing a mixture of short-term repopulating (STR), long-term repopulating (LTR) and progenitor cells. Lineage negative cells are about 20-fold enriched in HSC as compared to whole bone marrow. Thus, the data show that among lineage negative cells, cells bearing the IL-12 receptor are "expanded" following treatment with exogenous IL-12. The competitive repopulation study using isolated and selected IL-12R⁺ and IL-12R⁻ lineage negative cells further suggest that the "expansion" of Lin⁻ IL-12R⁺ cells represent expansion of LTR HSC (Table 4). Thus, taken together, the data suggest that the IL-12/IL-12R system is directly integral to processes of hematopoiesis and is a decisive factor in HSC preservation.

The IL-12 ligand is mainly produced in dendritic cells (43,44) that circulate in blood and are also resident in various tissues throughout the body (88). Generally circulating dendritic cells are referred to as monocytes and tissue-specific dendritic cells are referred to as macrophages. These dendritic cells are known as the "sentinel" cells of the body capable of sensing "stresses or threats" that relate to the survival needs of the organism (88). These "stresses or threats" come in the form of infections by virus and bacteria and injury and wounds, including loss of blood cells, e.g. blood cell loss following radiation damage or surgery. For example, when a lipopolysaccharide (LPS) molecule from an invading organism binds to a particular toll-like receptors located on the surface of dendritic cells, the IL-12 ligand is a direct product of this activation. It is in this manner that dendritic cells can "sense" "stresses or threats" to the organism (89). One of the critical responses of these "sentinel" cells is to increase the production of the IL-12 ligand to combat the "stress or threat" (88,89). Thus the IL-12 ligand can be viewed as a "danger signal" indicating the sensing by and subsequent activation of the "sentry" dendritic cells. Moreover, the IL-12 receptor on stem cells, which is activated by the IL-12 danger signal, provides a mechanism for alleviating the danger or threat to survival of the organism.

Figure 5:
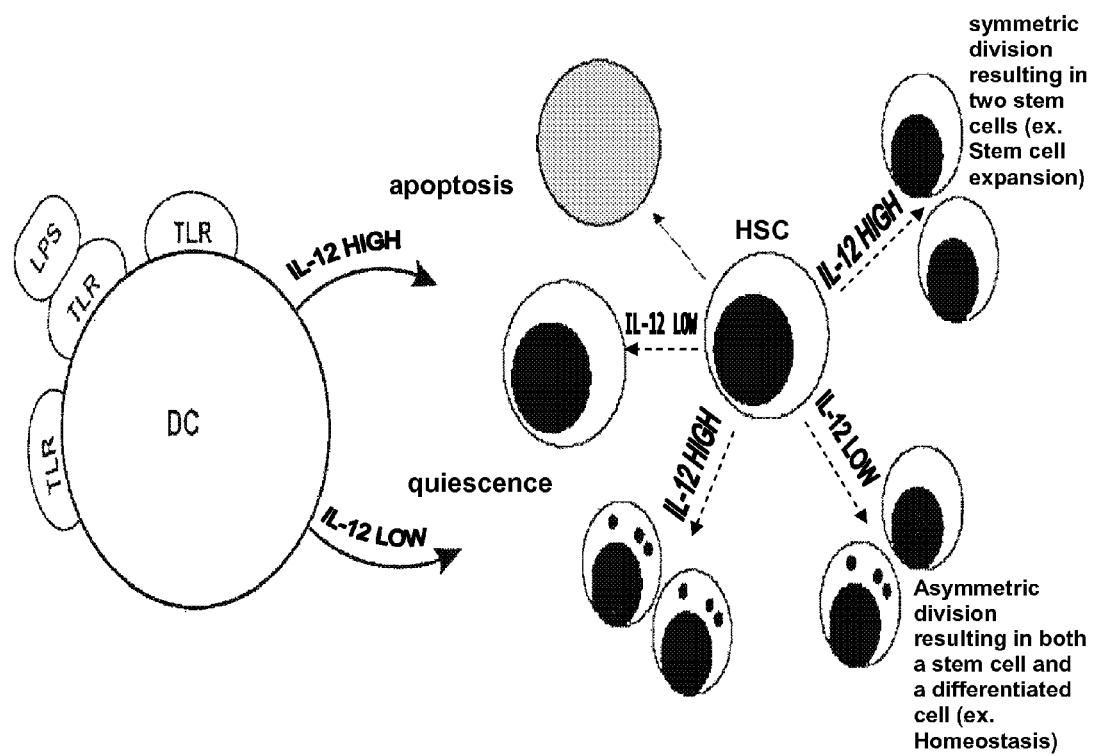
FIG. 5 shows a schematic of MSC regulation via the IL-12 ligand/IL-12 receptor system as controlled by dendritic cells (DC), as described in Example 7. IL-12 produced by activation of DC, or exogenous IL-12, can control the fate of HSC. HSC are characterized by an increased cell cycle quiescence compared to other cells. They can remain in quiescence, enter cell cycle to undergo symmetric or asymmetric division, or undergo apoptotic death. Recent reports indicate that bone marrow cells are regulated by DC (91). The "status" of IL-12, i.e., the concentration of IL-12, in circulation affects equilibria involved in the production of LTR HSC (symmetrical cell division producing two LTR) or STR HSC (symmetrical cell division producing two STR). Also the "status" of IL-12 can affect equilibria leading to the quiescent state or apoptosis. When the level of IL-12 is "high", largely symmetrical cell division will take place, but whether LTR or STR are mainly produced depends on other signals. When the status of IL-12 is "low", the equilibria are pushed toward asymmetrical cell division, leading to homeostasis, or quiescence, again depending on other signals.

In the context presented herein, an illustrative example is the signaling of "danger" in an organism following a non-lethal dose of radiation or wounding (96). Cellular debris, such as native DNA resulting from cell lysis of blood cells, can serve to activate dendritic cells resulting in production of the IL-12. This IL-12-mediated danger signal is then communicated to cells within the bone marrow compartment as a warning sign to produce more blood cells. Further, the data show that this danger signal in the form of the IL-12 ligand is directly communicated to HSC bearing the IL-12 receptor "instructing" these cells to expand in the face of impending danger (see Example 13 below). HSC identified by the presence of the IL-12 receptor are a subset of survival-responsive HSC that can rapidly be induced to expand under stress. An illustration of the master regulator function of IL-12 is depicted schematically in FIG. 5.

Following lethal radiation, these sentinel cells are affected by the radiation and can no longer produce sufficient quantities of IL-12 to rescue MSC residing in the bone marrow compartment. Thus, the exogenous addition of the IL-12 is necessary as a replacement for the impaired endogenous production of the IL-12 danger signal. With exogenous replacement of IL-12, HSC bearing the IL-12 receptor are induced to expand, thereby conferring survival to the organism in the face of lethal radiation.

The IL-12/IL-12R system represents a novel approach to the elucidation of HSC biology and preservation. This system not only allows elucidation of mechanisms related to HSC expansion, but also provides a functional system at the level of the organism to gauge HSC properties. Finally, as it relates to HSC, the IL-12/IL-12R system can provide a rapid inroad to a more focused understanding of stem cell biology, thereby advancing the manipulation of stem cells for clinical advantages.

J. Tissue Expression of IL-12Rβ2

The IL-12Rβ2 protein is expressed in a variety of tissues in the human body outside of the hematopoietic system, These cell populations represent sources of tissue-specific progenitor cells that could also proliferate and reconstitute the cell population in the presence of IL-12. Exogenous IL-12 could also provide repair of damaged or diseased tissue. One example is damage caused by chemotherapy or radiation.

Immunohistochemistry for IL-12Rβ2 shows that the receptor subunit is strongly expressed in the brain, specifically neuronal cells of the cerebral cortex, hippocampus, lateral ventricle, and the cerebellum. See the Human Protein Atlas entry on the world wide web for "IL12RB2". The Human Protein Atlas is described in *Nat Biotechnol.*, 28(12): 1248-50 (2010). Hepatocytes of the liver show weak staining for IL-12Rβ2, while glandular cells of the gall bladder exhibit moderate staining intensity. In the gastrointestinal tract, the stomach, duodenum, small intestine, appendix, and rectum show moderate staining for IL-12Rβ2. Other gastrointestinal regions show weak staining, such as the oral mucosa, salivary gland, esophagus, lymphoid tissue of the appendix, and the colon. Weak staining for IL-12Rβ2 has been shown in the nasopharynx, bronchus, and macrophages of the lung. Myocytes of the heart muscle also show weak staining. In the female reproductive system, the uterus shows moderate expression of IL-12Rβ2, while weak expression is exhibited in the breast, uterus, and fallopian tube. Decidual cells of the placenta show moderate expression of IL-12Rβ2, while trophoblastic cells of the placenta show weak expression. In the male reproductive system, moderate expression of IL-12Rβ2 is seen in leydig cells of the testis, while weak expression is seen in the epididymis, prostate, and seminal vesicle. Tubules in the kidney show moderate staining, while weak staining for IL-12Rβ2 is seen in the bladder. Skin also shows weak staining for IL-12Rβ2. Moderate IL-12Rβ2 staining is seen in the parathyroid and adrenal glands, while the thyroid exhibits weak staining for IL-12Rβ2.

Gastrointestinal Tract: IL-12Rβ2 expression is detected on both paneth cells and gastrointestinal stem cells on the crypt base of the small intestine. This observation is significant because the intestinal crypt paneth cells are responsible for maintenance of host defense in the intestine. Intestinal stem cells are responsible for the long-term maintenance of the intestine by constant replenishment of epithelial and goblet cells that makeup the intestinal villi. The close association of paneth cells with intestinal stem cells is thought to confer protection of a critical stem cell population from hostile pathogens. FIGS. 6a and 6b illustrate IL-12Rβ2 expression in the intestinal crypts of normal jejunum in humans and rhesus monkeys respectively. IL-12Rβ2⁺ intestinal crypts are indicated by arrows. Intestinal crypts are circled. Intestinal stem cells are interspersed between crypt cells and demonstrate characteristic "wedge shaped" morphology described intestinal crypt cells.

Salivary Glands: IL-12Rβ2 is expressed in normal human salivary glands. FIGS. 7A and 7B illustrate IL-12Rβ2 staining on normal serous secretory units (acini; labeled "AC") and excretory ducts (labeled "ED") of the parotid salivary gland in humans. The salivary acini secrete saliva and digestive enzyme into the oral cavity via excretory ducts. The implication is that hyposalivation (xerostomia) is a frequent and debilitating side effect or exposure to radiation and chemotherapy of head and neck cancer. There is a role for IL-12 in protection of serous secretory units from radiation-induced xerostomia.

The invention is further described by reference to the following examples, which are provided for illustration only. The invention is not limited to the examples, but rather includes all variations that are evident from the teachings provided herein. All publicly available documents referenced herein, including but not limited to U.S. patents, are specifically incorporated by reference.

K. Therapeutic Administration of IL-12

IL-12 can be used therapeutically as a stand-alone drug (i.e. without prior, concurrent, or post-administration use of therapeutic cell populations) to confer regeneration and healing in multiple tissues or organs.

The specific dose and administration of IL-12 is important for therapeutic regenerative actions of IL-12. For example, hepatic regeneration can be adversely effected by continuous IL-12 administration (IL-12 induces specific cytotoxicity against regenerating hepatocytes in vivo; Matsushita et al., International Immunology 11:657-665 (1999).

Regeneration of the bone marrow after radiation-induced myeloablation can be achieved to the degree that the animal is rescued from the tissue damage and survives, as shown in examples 1 and 17 in mice, and Example 18 in rhesus monkeys. Example 15 illustrates how IL-12 administration alone after myeloablative radiation can regenerate bone marrow and reconstitute the hematopoietic system as well as bone marrow transplant, i.e. the therapeutic use of cells for regeneration.

IL-12 receptors are expressed in many cell types in addition to hematopoietic and immune system cells of the bone marrow and circulating blood such as brain tissue, lung tissue, kidney tissue, pancreatic tissue, liver tissue, or cardiac tissue and the like. The cell types include stem cells, progenitors and other cells of more mature and mature lineages.

IL-12 receptors are also expressed on non-stem cells that are co-localized with stem cells in given tissues. These cells act as support for regeneration and contribute to the regenerative process. IL-12 modulation of these cells acts to further support the totality of the regenerative process.

IL-12 acts as a central actor in the regenerative system of mammals in response to injury and concomitant infections that occur with injury. Hence it is a general regenerative factor in the body.

The actions of IL-12 are not limited to cells wherein receptor expression can be clearly observed at basal levels, as is the case in many tissues. Expression of the IL-12 receptor is induced by injury, and thus after injury, cells expressing the IL-12 receptor become amenable to modulation by IL-12 and can participate in the act of the healing and regeneration.

Stem cell markers are co-expressed with the IL-12 receptor on a subpopulation of cell types. These markers (e.g. CDCP1, c-kit, KDR, Flt3, SLAM, CD133, IFNGR) are stem cell markers in numerous cell types (e.g. CD133 as a neural stem cell marker) and cells in body tissues expressing these markers are involved in regeneration of damaged tissue.

IL-12 administration is not limited to acting on only currently defined stem cell marker marked cells but on cells with still unknown stem cell markers.

IL-12 receptors are also expressed on non-stem cells that are co-localized with stem cells in given tissues. These cells act as support for regeneration and contribute to the regenerative process. IL-12 modulation of these cells acts to further support the totality of the regenerative process.

The specific dose and administration of IL-12 is important for therapeutic regenerative actions of IL-12. For example, hepatic regeneration can be adversely effected by continuous IL-12 administration (IL-12 induces specific cytotoxicity against regenerating hepatocytes in vivo; Matsushita et al International Immunology 11:657-665 (1999).

IL-12 can aid in healing after stroke due to ischemia, thrombosis, hemorrhage or other cause. IL-12 can be administered alone to regenerate damaged neural tissue after stroke, as well as after traumatic brain injury or following spinal cord injury. IL-12 can be administered to the nervous system using a variety of methods, including, for example: parenteral systemic administration; subcutaneous, intravenous, intraarterial, intramuscular or intraperitoneal administration; direct cerebrospinal administration (epidural or peridural); intracerebral or intracerebroventricular administration. Spinal cord injuries can be treated with IL-12 by systemic administration as described above and also by intrathecal administration (spinal canal administration).

Hematopoietic disorders of the bone marrow such as idiopathic thrombocytopenic purpura (ITP) or myelodysplastic syndrome (MDS) can be treated with administration of IL-12.

Therapeutic use of IL-12 can address hepatic damage due to injury or disease state; pancreatic damage due to injury or disease state; heart damage due to injury or disease state; kidney damage due to injury or disease state; GI damage due to injury or disease, immune, hematopoietic and circulatory damage due to injury or disease state and other organ or tissue damages due to injury or disease state.

Use of IL-12 to treat damage due to injury or disease state can be applied to organs or tissues of the body including, for example, the circulatory system, digestive system, endocrine system, excretory system, integumentary system, lymphatic system, muscular system, nervous system, reproductive system, respiratory system, skeletal system.

Depending on appropriate treatment modality, administration can be local, systemic, parenteral or topical. Depending on need, route of administration may be enteric, epidural, intracerebral, intracerebroventricular, epicutaneous, intradermal, subcutaneous, nasal, intravenous, intraarterial, intramuscular, intracardiac, intraosseous infusion, intrathecal, intraperitoneal, (infusion or injection into the peritoneum) e.g. peritoneal dialysis, intravesical, intravitreal, intracavernous, intravaginal, intrauterine, extra-amniotic, transdermal, transmucosal, rectal or other known route of administration known in the art.

EXAMPLES

Overview

The applicant conducted research that led to the discovery of the radiation survival effect of IL-12. These studies demonstrated that endogenously secreted factors are sufficient for hematopoietic rescue of a subject following lethal radiation. (71) The experimental scenario is as follows. Animals were first implanted with a TheraCyte immunoisolation device (TID). Following implantation of the device, the animals received a lethal-dose of radiation, and then normal bone marrow Lin⁻ cells were loaded into the device (thereby preventing direct interaction between donor and recipient cells). For control animals, the implanted device was loaded with PBS with or without other types of cells. Animal survival was evaluated and stem cell activity was tested with secondary bone marrow transplantation and flow cytometry analyses.

These experiments provided clues as to the nature of the endogenous, lethal radiation, survival factors. First, there was a temporal effect related to the time allowed for vascularization of the device following surgical implantation in relation to the radiation event. This observation led to the hypothesis that secreted hematopoietic factors involved in recovery from the local injury, produced at the site of implantation, might be responsible for the rescue effect. Since pro-inflammatory and inflammatory factors are generally known to be elicited following injury (72-74), it was postulated that IL-12 might be one of the factors responsible for the protection and survival effect. This postulate was later borne out by the data presented herein.

The examples described below demonstrate that IL-12 administration provides a "survival effect" to lethally irradiated mice via the IL-12R⁺ HSC. The IL-12-induced, hematopoietic "survival effect" via the IL-12R⁺ HSC is specific in that it does not occur with other similar cytokines The survival effect stems from the interaction of IL-12 with IL-12R⁺ long-term repopulating hematopoietic stem cells, thereby providing significant clinical importance. IL-12 administration acting on the IL-12R⁺ yields USC hematopoietic recovery following lethal and sublethal radiation by attenuating the decrease in blood cell counts observed after lethal and sublethal radiation. These examples also show that in vivo pretreatment with the IL-12 ligand leads to an increase in the relative number of IL-12R⁺ cells isolated from bone marrow and competitive repopulation studies indicate that IL-12R⁺ cells comprise LTR HSC. Taken together, these examples show that IL-12 acting via the IL-12R⁺ HSC is an in vivo hematopoietic stem cell protection and expansion factor that allows for both rapid and broad range recovery of hematopoiesis following hematological insult and that the IL-12 receptor is a novel hematopoietic stem cell marker.

Example 1

Low Dose of IL-12 Acting Via the IL-12R⁺ Stem Cell can Protect Mice from Lethal Ionizing Radiation IL-12 (100 ng/mouse) was administered to C57BL/6J mice intravenously either 24 hours before or 1 hr after lethal dose irradiation. Control mice were irradiated and given PBS buffer. For mice given IL-12 before radiation, the survival rate is about 92%. For mice given IL-12 following radiation the survival rate is about 78%. No control animals survived. In this example, IL-12 is effecting survival via interaction with the IL-12 R⁺ stem cell (HSC). Survival data are shown in FIG. 1.

Example 2

IL-12/IL-12R Stem Cell Radioprotection Requires a Time Window of Administration

The radiation rescue effect was tested at different times of administration of the IL-12, as described in Example 1. As shown in Table 2 below, approximately 100% or 80% rescue was achieved when 100 ng of IL-12 was administrated 24 hours before or 1 hour after total body irradiation, respectively. IL-12 was generally ineffective at the other times of administration tested. The time window for administration of IL-12 along with radiation, particularly for administration after radiation, suggests that the lethal radiation survival can only be effected at about 24 hour intervals. When mice are given IL-12 12 hours before radiation, the survival rate goes down. This indicates that the IL-12R⁺ stem cells are undergoing expansion and are no longer quiescent, and therefore more expanding stem cells are exposed to radiation. The lower survival rate also indicates HSC expansion because it takes about 24 hours to complete.

TABLE 2

RADIATION RESCUE OF MICE BY IL-12 INJECTION

| IL-12 administration time (hours) | Control | −48 | −36 | −24 | −12 | +1 | +12 | +24 | +36 |
|---|---|---|---|---|---|---|---|---|---|
| Total mice # | 10 | 10 | 10 | 10 | 10 | 10 | 5 | 10 | 5 |
| Survived | 0 | 0 | 0 | 10 | 2 | 8 | 0 | 2 | 0 |
| Survival rate (%) | 0 | 0 | 0 | 100 | 20 | 80 | 0 | 20 | 0 |

Example 3

IL-12/IL-12R⁺ Stem Cell Rescue Effect is Specific

Several cytokines related to IL-12 were also tested before and after Total Body Irradiation, as listed in Table 2. INF-γ has previously been show to be ineffective (51). Like IL-12, both IL-18 and IL-23 are known to induce INF-γ production. IL-23 is in the same cytokine family as IL-12, sharing one subunit, namely the p40 subunit, and also sharing the beta 2 subunit of the IL-12 receptor. IL-2 is also similar to IL-12 in that it is an immuno-modulator of T cell differentiation. GM-CSF is known to stimulate the proliferation of neutrophils and macrophage progenitors.

All the cytokines were given at a dose of 100 ng/mouse, 30 to 60 minutes post-radiation. As shown in Table 3 below, the rescue effect is observed only for IL-12 and IL-12/GM-CSF treated mice. Since GM-CSF alone was not observed to provide protection, the protective effects observed for the IL-12/GM-CSF group are reflective of the protective effects of IL-12 alone. These results demonstrate that the IL-12 protective effect appears to be specific, as these effects are not produced by any of the IL-12-related cytokines tested herein

TABLE 3

RADIOPROTECTION EFFECTS OF DIFFERENT CYTOKINES INJECTED AFTER TBI

| | Control | GM-CSF | IL-2 | IL-18 | IL-23 | p40 | GM-CSF + IL-12 | IL-12 |
|---|---|---|---|---|---|---|---|---|
| Total mice Number | 5 | 4 | 5 | 4 | 5 | 5 | 5 | 5 |
| Survived | 0 | 0 | 0 | 0 | 0 | 0 | 4 | 4 |
| Survival (%) | 0 | 0 | 0 | 0 | 0 | 0 | 80 | 80 |

Example 4

Figure 3:
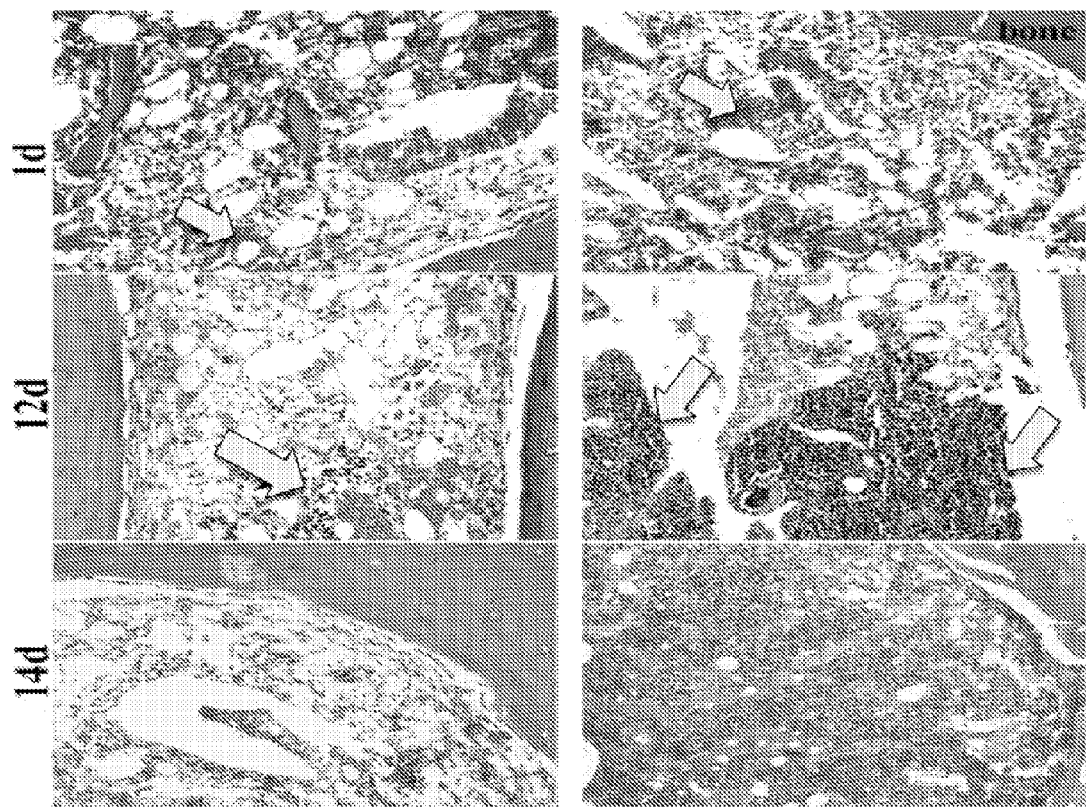
FIG. 3 shows photomicrographs of femurs sectioned from animals treated with and without IL-12, as described in Example 4. The femurs were fixed and stained for hematoxylin and eosin. Arrows at 1 day point to hemorrhage. Arrows at 12 days point to mononuclear colonies. 14 days shows the overall increase in regeneration after IL-12 treatment 200× magnification. d: days post radiation.

Administration of IL-12 Acting Via the IL-12R$^+$ Stem Cell Induces Hematopoietic Recovery Following Lethal or Sublethal Radiation of all Major Blood Groups In both animal toxicity studies and in clinical studies, high dose and/or repeated administration of IL-12 results in inhibition of hematopoiesis, i.e., a decrease in the blood cell counts in peripheral blood, a decrease in bone marrow cellularity, and a decrease in colony forming (CFC) cells are observed. Blood cell counts were examined in both lethally irradiated (1000 rad or about 10 Gray) and sublethally irradiated (500 rad or about 5 Gray) animals, as shown in FIG. 2. After a lethal dose of irradiation, there was no difference between the IL-12-treated and the non-treated animals in terms of peripheral blood counts during the first 12 days post-radiation. However, after 12 days, a rapid recovery of blood cell counts was observed in IL-12-treated animals, while all the control animals died (FIG. 2). Examination of bone marrow cellularity revealed that at 9 days post-radiation, there were 3 times more cells in the bone marrow of IL-12-treated animals than in control animals ($9.5 \times 10^5$ vs. $3.1 \times 10^5$). Histological examination of the bone marrow of the IL-12 treated animals showed that these animals displayed a higher cellularity and better preservation of the bone marrow structure as compared to control animals, as shown in FIG. 3. After sublethal irradiation, the blood cell counts in animals treated with IL-12 (either before or after radiation) showed less of a cell count drop and an earlier recovery.

Example 5

IL-12 Acting Via the IL-12R$^+$ Stem Cell Rescues IL-12R$^+$ Long-Term Repopulating (LTR) Hematopoietic Stem Cells Most radioprotection studies observe animals for 30 days to determine the survival effect. However, radiation-induced genomic instability and bystander effects result in damage that may affect the hematopoietic system long after the acute stage of radiation-induced injury. Only one study has carried out a long-term observation (300 days post-radiation) to assess the radioprotective effect of a combination of several growth factors on hematopoiesis over the long-term (54). The viability and long-term survival of the long-term repopulating hematopoietic stem cells was examined. Six months after a lethal dose of TBI, mice that had survived, due to the protective effects of IL-12 treatment, were sacrificed, their bone marrow cells harvested, and $1 \times 10^6$ donor bone marrow cells (identified by the congenic marker Ly5.2) were transplanted into lethally irradiated (950 rad) recipients (identified by the congenic marker Ly5.1). Mice receiving the transplanted bone marrow cells outlived controls by at least 6 months.

Hematopoietic stem cells are a group of heterogeneous cells which contain long-term repopulating (LTR) HSC with complete self-renewal ability, short-term repopulating (STR) HSC with limited self-renewal ability, and uncommitted progenitor cells without self-renewal ability (10). Each of these subsets was examined to determine which compartments of HSC are protected by, or responsive to, IL-12 after lethal radiation using assays of transplanted bone marrow cells. Bone marrow was transplanted to secondary irradiated mice to test LTR HSC (FIG. 4A, D-F). Day 12 colony-forming units-spleen (CFU-S$_{12}$) from the mice receiving the transplant were assayed to examine STR HSC (FIG. 4B), and colony-forming cells (CFC) assays were used to test for progenitor cells (FIG. 4C). Immediately after radiation (0 day), IL-12-treated bone marrow had already lost CFU-S$_{12}$ and CFC activities. The recovery of LTR HSC activity in IL-12-treated bone marrow appeared by day 7 post radiation (FIG. 4A). STR HSC activity (CFU-S$_{12}$) appeared almost fully recovered by day 10 after radiation (FIG. 4B), and progenitor cell activity (CFC colonies) appeared recovered by day 14 (FIG. 4C). This time sequence of dynamic recovery of activities from 7 days (LTR HSC) to 10 days (STR HSC) to 14 days (progenitor cells) matches the time course of the normal HSC differentiation sequence from LTR HSC to STR HSC to progenitors and is also correlated with expansion of mononuclear colonies of IL-12-treated bone marrow at day 12 (FIG. 4B). Thus the STR HSC(CFU-S$_{12}$) and progenitor cell (CFC colonies) activities observed were all derived from the protected and/or expanded LTR HSC. These LTR HSC recovered from IL-12-treated bone marrow 6 months after radiation rescued lethally irradiated mice in the long term and repopulated the complete hematopoietic system (FIG. 4D), including myeloid cells ($14.1 \pm 1.4\%$; FIG. 4E), and lymphoid cells ($15.1 \pm 3.1\%$; FIG. 4F). The results indicate that LTR HSC, but not STR HSC or progenitor cells, are protected by IL-12 from radiation. Taken together with the results in Tables 3 and 4, these data show that IL-12 is acting via the IL-12R$^+$ LTR HSC.

Example 6

IL-12 Increases the Number of Sca-1$^+$ HSC in vivo

By screening two known stem cell markers, namely Sca-1 and the Kit receptor, we found that Sca-1$^+$ cells were increased in IL-12-treated bone marrow as compared with untreated bone marrow, 19.2% vs. 9.7% ($p<0.05$), respectively, at 24 hours post radiation. At day 7 post radiation, at which time LTR HSC showed repopulation activity, there was as statistically significant greater number of Sca-1$^+$ cells, $1.2 \times 10^5$ vs. $7.8 \times 10^4$ ($p<0.01$), in IL-12-treated bone marrow as compared with untreated mice. After lethal radiation, almost all c-kit marker cells were depleted from bone marrow cells. There was no difference in the number of c-kit+ cells with or without IL-12 treatment. Further support comes from an early report that demonstrates the direct effect of IL-12 on the expansion of HSC, which are lineage negative, Sca+ cells (92).

Example 7

Isolation of IL-12R+ Stem Cells from Bone Marrow

The IL-12 ligand has a direct effect on HSC expansion via the IL-12 receptor present of LTR HSC. In addition, HSC expansion can lead either to the production of two daughter LTR HSC (symmetrical cell division) or one LTR HSC and one STR HSC (asymmetrical cell division), depending on the status of the IL-12 ligand in circulation, i.e., concentration of IL-12 and/or other factors (see schematic in FIG. 5).

Lineage negative IL-12R+ and IL-12R− cells were isolated from bone marrow and selected via FACS, and transplanted these cells into congenic recipients. The goal of this experiment is to observe the donor cell contribution for at least a period of at least four months, which would be indicative of long-term repopulation. Herein, we report the repopulation data collected at various time points.

In vivo Pretreatment of Mice with Exogenous IL-12 Directly Increases the Number of IL-12R+ Cells Isolated from Bone Marrow in the Absence of Radiation C57BL/6 mice (6-8 weeks old) were either treated with exogenous IL-12 (100 ng/mouse) via tail vein injection (Treated group) or not treated (Untreated group). Both groups were then sacrificed and their bone marrow cells were harvested. In one group of mice (Group A), bone marrow was harvested 25 hours after treatment with IL-12, and for another group of mice (Group B), bone marrow was harvested at 21 hours after treatment with IL-12. Following isolation of whole bone marrow cells, both groups of cells were depleted of lineage positive cells. For lineage positive cell depletion, bone marrow cells were fractioned to yield lineage negative cells (Lin−) using lineage positive cell markers, namely, CD3e, CD4, CD5, CD8b, CD11b, Gr1 and Ter (80). Lin− cells were then collected using a magnetic cell sorting system. Next, lineage negative cells were further fractionated via fluorescence-activate cell sorting (FACS) using the HAM10B9 antibody, which reacts with the β2 subunit (IL-12Rβ2) of the mouse IL-12 receptor complex. FACS selection to yield Lin− IL-12R+ and Lin− IL-12R− cell populations. FACS analysis, shown in Table 4 below, revealed a 3.5 to 5.4 fold increase in Lin− IL-12R+ cells isolated from mice following treatment with IL-12 ligand.

TABLE 4

INCREASE IN LIN− IL-12R+ CELLS ISOLATED FROM MICE TREATED WITH IL-12 LIGAND

| | Treated Group | Untreated Group | Fold-Increase in Lin− IL-12R+ cells |
|---|---|---|---|
| Group A (25 hour harvest) | 2.7% | 0.5% | 5.4 fold (after 25 hours) |
| Group B (21 hr. harvest) | 2.1% | 0.6% | 3.5 fold (after 21 hours) |

These data indicate that pre-treatment with exogenous IL-12 yields an increase in the relative number of Lin−, IL-12+ cells among lineage negative cells of the bone marrow compartment, and results in an average 4.5 fold enhancement of IL-12R+ cells for the two different pretreatment time points. These data are also consistent with our BrdU incorporation assay in the absence of radiation, which showed an increase in BrdU positive cells in whole bone marrow (16.5%) in IL-12-treated mice as compared with untreated mice (7.5%) 21 hours after treatment. These data show that the observed increase in isolated and selected lint IL-12R+ cells from bone marrow following in vivo pretreatment with the IL-12 ligand results from direct HSC expansion via the IL-12 ligand/IL-12 receptor system, leading to an increase in the number of daughter HSC bearing the IL-12 receptor. This is consistent with the literature (90-93) and the data below.

Competitive Repopulation Using Lin− IL-12R+ or Lin− IL-12R− Isolated Bone Marrow Cells For the competitive repopulation experiment, congenic donor and recipient mice were used: donor mice (C57BL/6) bearing the Ly5.2 (CD45.2 or ptprc$^b$ allele) genetic marker and recipient mice (C57BL/6) bearing the Ly5.1 (CD45.1 or ptprc$^a$ allele) genetic marker. Cells from treated and untreated donor mice generated from Example 7 above (Lin− IL-12R− and Lin− IL-12R+) were each transplanted into lethally irradiated recipients (950 rad) within 3 hours of radiation. Each group of transplanted cells were supplemented with competitor cells in a 1:375 ratio of selected cells to competitor cells.

Recipient Ly5.1 mice were separated into five groups: Group 1 received a transplant containing Lin− IL-12R+ cells isolated from treated donor Ly5.2 mice, as described above, Group 2 received a transplant containing Lin− IL-12R+ cells isolated from untreated Ly5.2 donor mice, also as described above; Groups 3 and 4 received a transplant containing Lin− IL-12R− cells from treated or untreated donor Ly5.2 mice respectively. Group 5 received Lin− IL-12R+ cells from treated donor mice (the same as Group 1), but also was subsequently treated with exogenous IL-12 (100 ng/mouse via tail vein) 3 days after radiation and transplantation. Peripheral blood cells from mice in each group were sampled at five time points and subjected to FACS analysis for the marker Ly5.2 to determine the percentage of donor cells. The data are shown in Table 5 below, which gives the % donor cell contribution, as measured by FACS analysis of peripheral blood cells for the Ly5.2 (CD45.2) marker at five time points.

TABLE 5

% DONOR CELLS IN PERIPHERAL BLOOD AT TIME PERIODS POST TRANSPLANT

| | % Donor Contribution | | | | |
|---|---|---|---|---|---|
| | 32 Days | 40 days | 75 days | 97 days* | 6 months |
| Group 1 T IL-12R+ | 2.5 | 2.5 | 2.2 | 1.4 | 5.0 |
| Group 2 U IL-12R+ | 8.8 | 3.0 | 1.5 | 0.8 | 9.2 |
| Group 3 T IL-12R− | 16.8 | 1.7 | 2.0 | 0.9 | 3.6 |

TABLE 5-continued

% DONOR CELLS IN PERIPHERAL BLOOD AT
TIME PERIODS POST TRANSPLANT

| | % Donor Contribution | | | | |
|---|---|---|---|---|---|
| | 32 Days | 40 days | 75 days | 97 days* | 6 months |
| Group 4 U IL-12R$^-$ | 48.3 | 2.2 | 2.6 | 1.0 | 10.0 |
| Group 5 T IL12R$^+$, +IL12 | 58.8 | 2.4 | 2.1 | 1.7 | 13.8 |

*Animals were taken off antibiotics around day 92.

Treated groups receiving transplants of IL-12$^+$ and IL-12$^-$ cells (Groups 1 and 3) show less peripheral blood repopulation by short term repopulating cells (STR) than Untreated groups (Groups 2 and 4). In this Example, STR includes differentiated cells. Comparison of Untreated Group 1 to Untreated Group 5 indicates that exogenous IL-12 following the transplant of Lin$^-$ IL-12R$^+$ cells leads to a rapid and significant increase in STR; these comparative data further indicate the direct expansion of Lin$^-$ IL-12R$^+$ by the IL-12 ligand resulting in a large number of STR donor cells. A sharp drop in the STR cells counts was observed in donor peripheral blood cells around the 40 day mark for all groups except Group 1; this sharp drop in peripheral blood cells has been observed previously for LTR HSC and indicates the demise of STR cells (10). Group 2 had a large amount of change in the percentage of donor cells between 40 days and 6 months post-transplantation, while Group 1 has relatively little change over the same time period, showing that Group 2 (untreated Lin$^-$ IL-12R$^+$ cells) had more STR cells than Group 1 (treated Lin$^-$ IL-12R$^+$ cells). Only treated Group 1 showed no change in repopulation between sampling days 40 and 75, indicating that pretreatment with IL-12, followed by selection of Lin$^-$ IL-12$^+$ cells yields predominately LTR HSC. Untreated Lin$^-$ IL-12R$^+$ cells (Group 2) show the smallest negative fold-change in donor cells from peripheral blood, indicating that Group 2 is less enriched in LTR HSC than Group 1, but significantly more enriched in LTR HSC than its counterpart Group 4, or even treated group 3. Overall, the significant differences between treated and untreated groups show that pretreatment with IL-12 leads to expansion of LTR HSC in the bone marrow compartment, mobilization of STR into the peripheral blood, and subsequent differentiation. Thus, Lin$^-$ cells isolated following pretreatment with IL-12 ligand are comparatively enriched in LTR HSC.

Taken together, the data indicate that Lin$^-$ IL-12R$^+$ cells are present in the bone marrow as both LTR HSC and STR HSC cells under "low" IL-12 conditions (untreated groups). Upon pretreatment or post treatment with exogenous IL-12, a "high" status of the IL-12 danger signal is generated, whereby HSC are expanded and the STR HSC are mobilized away from the bone marrow and into peripheral blood as previously reported in Jackson et al. (70). This scenario is consistent with the presence of high levels of the IL-12 danger signal as the organism is preparing to combat the "stress or threat" associated with the danger signal. It is also likely that under a "high" IL-12 status, mobilization of IL-12R$^+$ STR HSC also leads to differentiation. Referring to the schematic in FIG. 5, the data further indicate that following the "highly active" HSC state of expansion, mobilization and differentiation resulting from a "high" IL-12 danger signal, if the status of the IL-12 danger signal becomes "low," the LTR HSC enter the quiescent state. The data in Table 4 suggest that a IL-12 "low" status results following the subsequent isolation, purification and transplantation of IL-12R$^+$ into lethally irradiated recipients. Moreover, as discussed, even following transplantation, lethal radiation leaves the recipient in a state of IL-12 "low" because the main source of IL-12, the sentinel dendritic cells, are initially lost until reconstitution via the transplant can occur.

Although the dose of IL-12 used as the in vivo pretreatment or post treatment is considered a "low" exogenous dose, this dose is probably at, or higher than, what would be high levels of endogenously generated IL-12 under various "stresses or threats" to the organism. It is also noteworthy that under the "stress or threat" of cancer, IL-12 is generally down-regulated. This down regulation of IL-12 may be directly related to the proliferation of cancer cells under what would be perceived by the organism as a lack of a danger signal and its subsequent responses (94).

About 92 days post transplantation the mice were taken off antibiotics. Antibiotics are generally known to suppress hematopoiesis. FACS analysis performed on day 97 showed a drop in the peripheral blood counts resulting from the transplanted labeled cells (CD45.2).

The results at 6 months show that the Lin$^-$, IL-12R$^+$ cells are true long-term repopulating stem cell. After 6 months, the IL-12R$^+$ stem cells still persist and produce peripheral blood cells at a higher rate than when the donor stem cell was first transplanted. The persistence over time is the hallmark of a true long-term repopulating stem cell. Moreover, the expected percentage of donor cells in peripheral blood would be expected to be about 0.2-0.3%. However, the actual percentage for the IL-12R$^+$ treated mice from Group 1 is about 25 times higher than the expected percentage donor contribution based on the ratio transplanted donor cells, and for IL-12 treated mice in Group 5, the donor contribution is about 35 times expectations. For the IL-12R$^+$ untreated mice from Group 2, the actual donor contribution is greater than 50 times the expected donor contribution. Importantly, these results also show that by first treating mice with the IL-12 ligand and then isolating Lin$^-$, IL-12R$^+$ cells, the resultant population of stem cells is mainly only LTR HSC. This result could have significant clinical benefit in enabling the selection of IL-12R$^+$ stem cells with long-term repopulating ability.

Example 8

Effect of IL-12 Administration on Mouse IL-12R$^+$ Stem Cells in Bone Marrow and GI Tract Femoral bone marrow from irradiated mice treated with vehicle or recombinant murine IL-12 (rMuIL-12) 24 hours or more after TBI (LD30/30) were stained for IL-12Rβ2 and evaluated for histological signs of recovery from radiation-induced injury at 12 days post TBI. As a control, bone marrow from non-irradiated, untreated mice was characterized with the presence of IL-12Rβ2-expressing hematopoietic stem cells, identified by co-staining for Sca-1 (a murine stem cell marker), immature megakaryocytes with lobulated nuclei surrounded by a narrow rim of cytoplasm, matured megakaryocytes with lobulated nuclei and voluminous cytoplasm, and myeloid progenitor cells in the metamyelocyte stage (FIG. 8a).

Figure 8:
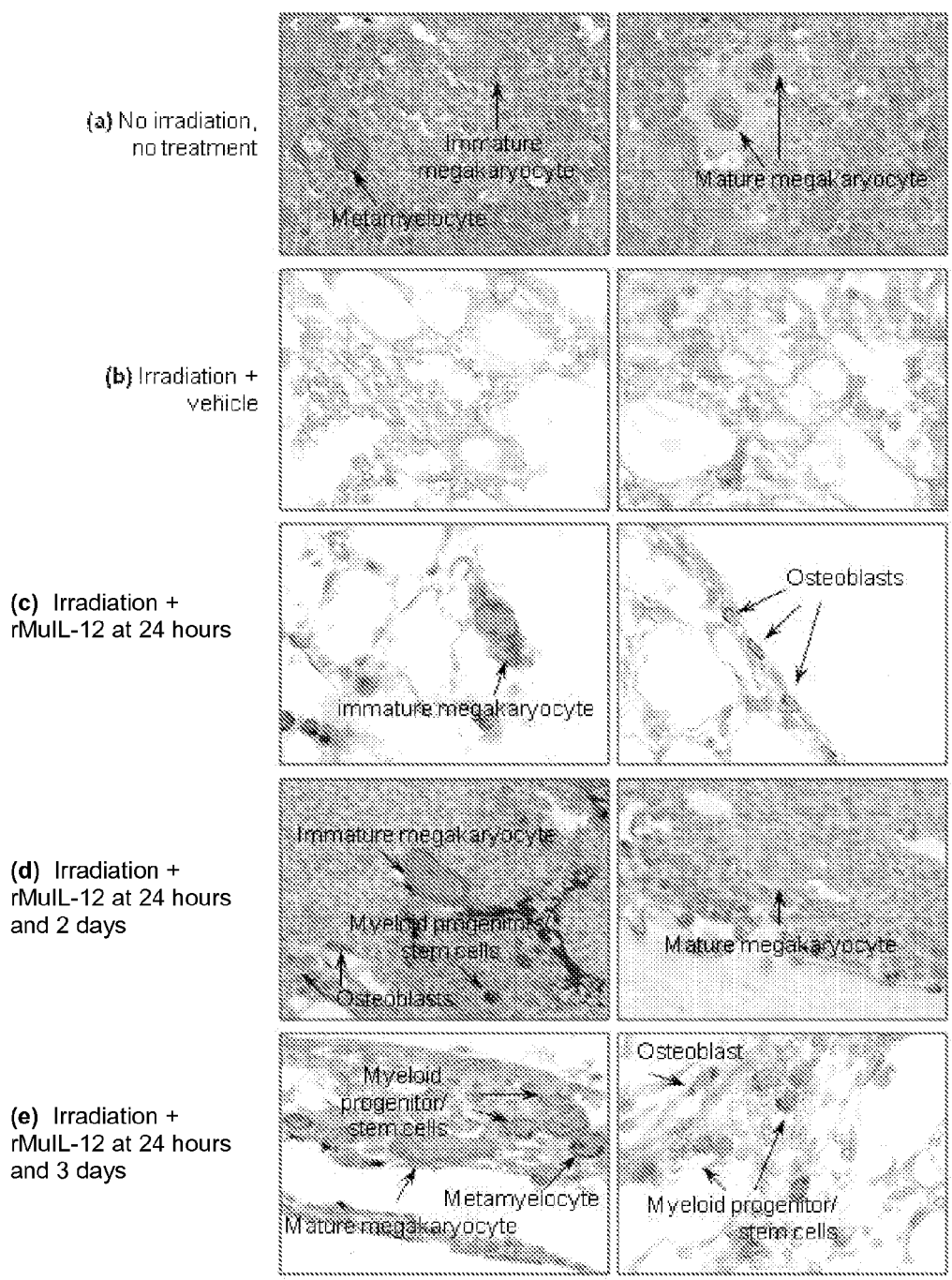
FIG. 8 is a series of photomicrographs of mouse femoral bone marrow stained for IL-12Rβ2, as described in Example 8. The mice were subjected to total body irradiation (8 Gy) and received either vehicle or rMuIL-12 at various times post-irradiation.
Figure 8:
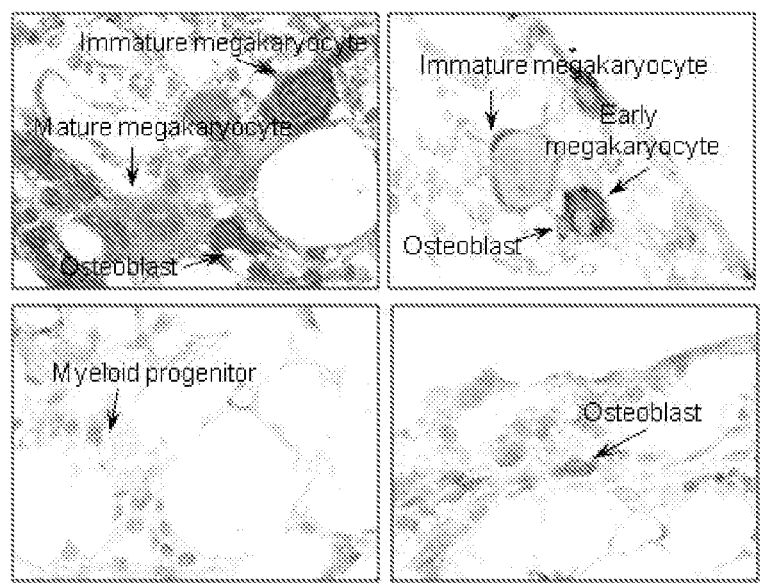

Bone marrow from mice treated only with vehicle and subjected to an LD30/30 of TBI (8.0 Gy) was characterized with minimal signs of hematopoietic regeneration and the complete lack of IL-12Rβ2-expressing cells after 12 days following irradiation (FIG. 8b). In contrast, mice treated with various dosing regimens of rMuIL-12 showed varying levels of hematopoietic reconstitution, which was characterized with the presence of IL-12Rβ2-expressing myeloid progenitors, megakaryocytes, and osteoblasts (FIG. 8c-f). Mice treated with rMuIL-12, which has been demonstrated to not cross react with IL-12 receptor, showed some signs of regeneration, however, lacked megakaryocytes (FIG. 8g). For mice treated with rMuIL-12, however, no increase in the survival was observed, as compared with the vehicle control group.

Figure 9A:
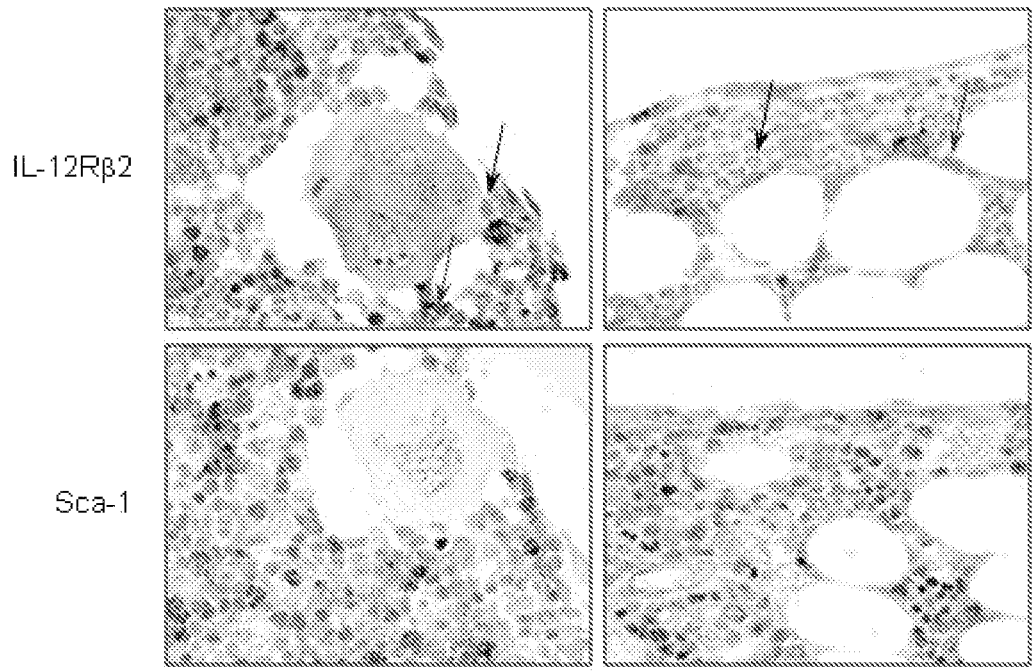
FIG. 9A shows tissue sections obtained 30 days after total body irradiation.
Figure 9B:
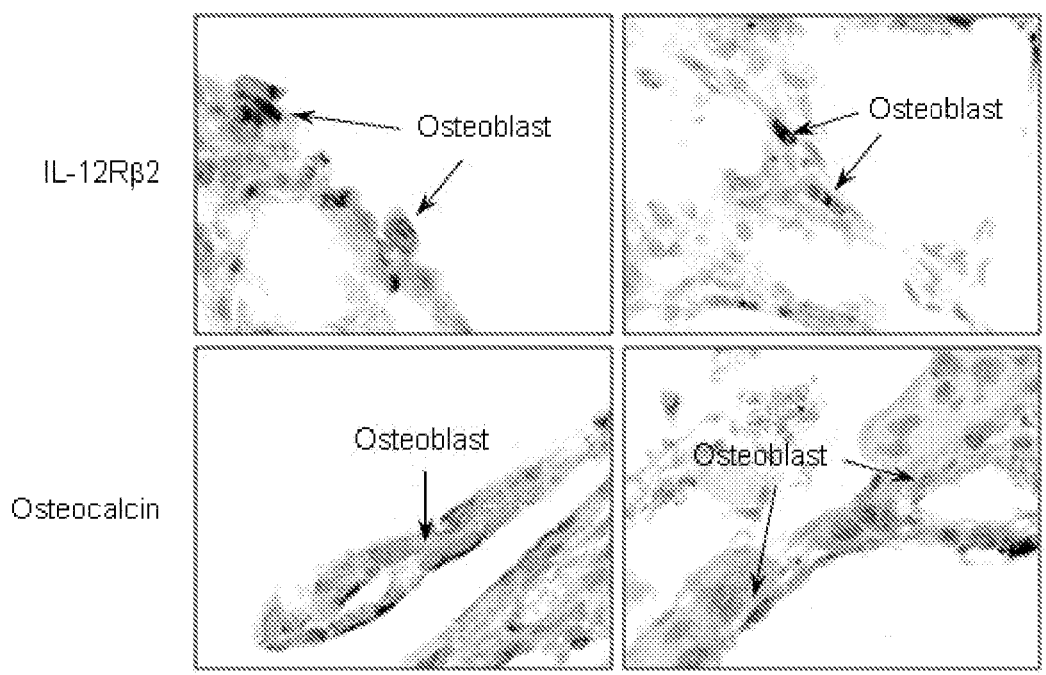
FIG. 9B shows tissue sections obtained 12 days after total body irradiation. Magnification is 100×.

In order to further evaluate as to whether morphologically identified cells were indeed hematopoietic stem cells and osteoblasts, bone marrow tissue sections were stained for the corresponding markers Sca-1 (for hematopoietic stem cells) and osteocalcin (for osteoblasts). As depicted in FIG. 9, IL-12Rβ2 expression was observed on cells that were morphologically identified as hematopoietic stem cells and osteoblasts, which expressed Sca-1 (FIG. 9A) and osteocalcin (FIG. 9B), respectively.

Figure 10A:
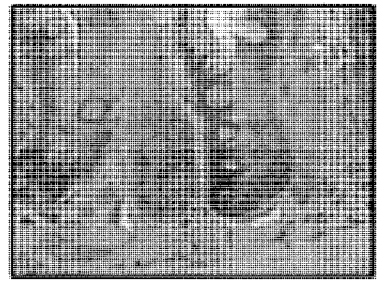
FIG. 10A is a photomicrograph of mouse jejunal crypts stained for IL-12Rβ2, as described in Example 8.
Figure 10B:
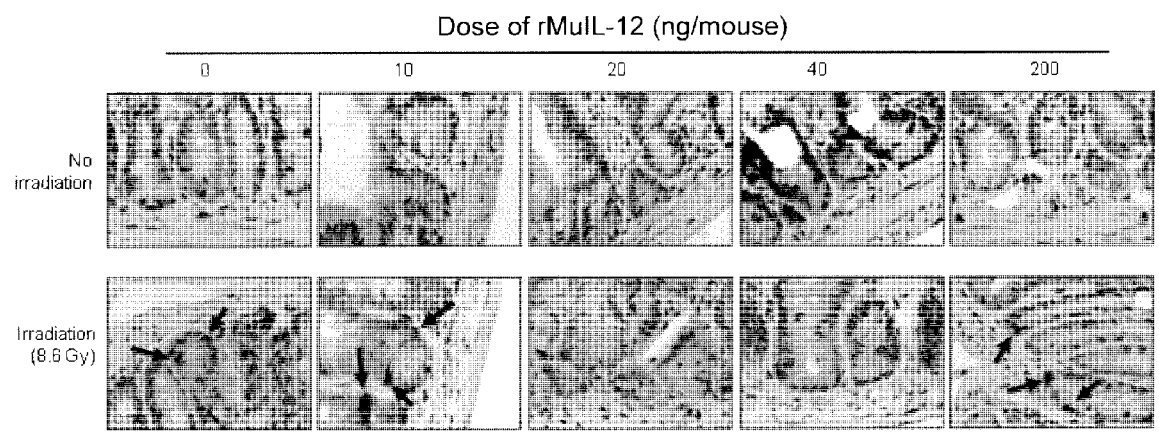
FIG. 10B is a series of photomicrographs of jejunal crypts from mice treated with rMuIL-12, either without irradiation (top panels) or with irradiation (8.6 Gy; bottom panels).

Similar to hematopoietic stem cells and osteoblasts in femoral bone marrow, mice jejunal crypts of the gastrointestinal tract expressed IL-12Rβ2 (FIG. 10a). In the absence of irradiation, rMuIL-12 administration at doses up to 200 ng/mouse did not cause injury in jejunal crypts (FIG. 10b, upper panels). Exposure to TBI (8.6 Gy), however, resulted in substantial jejunal damage 3 days after irradiation, as evidenced by the widespread expression of LGR5, a GI stem cell marker that is expressed upon GI injury. Remarkably, administration of rMuIL-12 at the low dose range of 10 ng/mouse to 40 ng/mouse dose-dependently mitigated radiation-induced jejunal damage, with no LGR5 expression evident at the optimal, efficacious dose of 20 ng/mouse (FIG. 10b, lower panels). In contrast, rMuIL-12 at the high dose of 200 ng/mouse exacerbated jejunal injury (FIG. 10b, lower panel; tissue is counterstained to show structure; arrows point to LGR5 positive cells). As observed with the rMuIL-12 dose ranges for optimal increases in survival, these data show a window of opportunity for mitigation of radiation injury by rMuIL-12 in a very low dose range of the drug that is also effective in alleviating bone marrow damage.

Example 9

Expression of IL-12R$^+$ Stem Cells in Primate Bone Marrow and GI Tract

Figure 11A:
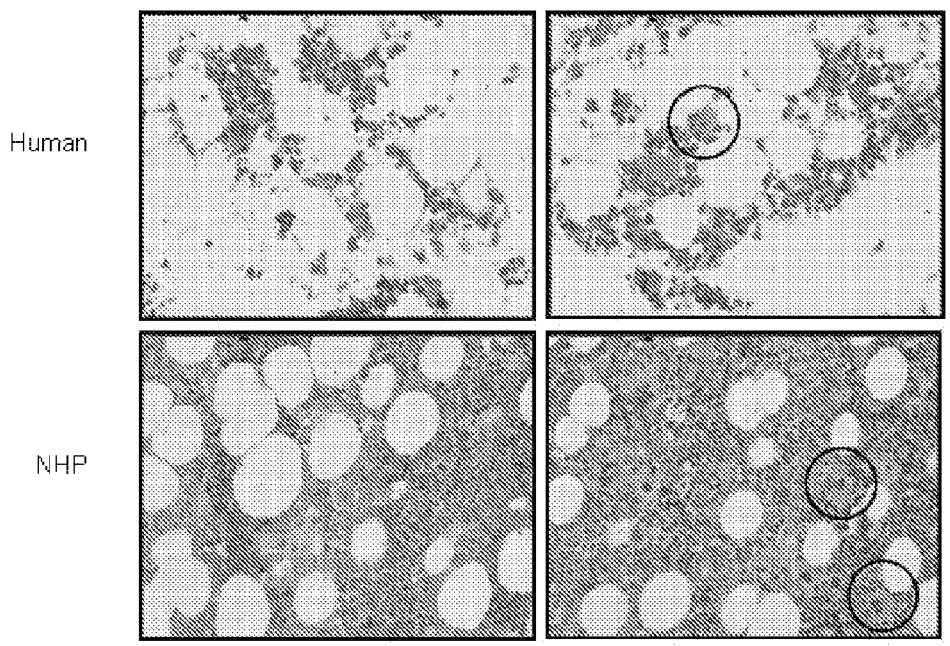
FIG. 11A is a series of photomicrographs of femoral bone marrow from non-human primate (NHP) or human, stained for IL-12Rβ2, as described in Example 9.

The expression of IL-12Rβ2 in non-irradiated rhesus monkeys and human femoral bone marrow and jejunum/ileum was evaluated by immunohistochemistry. As depicted in FIG. 11A, non-human primate, as well as human, progenitor cells and megakaryocytes expressed IL-12Rβ2. The expression of IL-12Rβ2 was also found on osteoblasts/osteoclasts from the bone marrow.

Figure 11B:
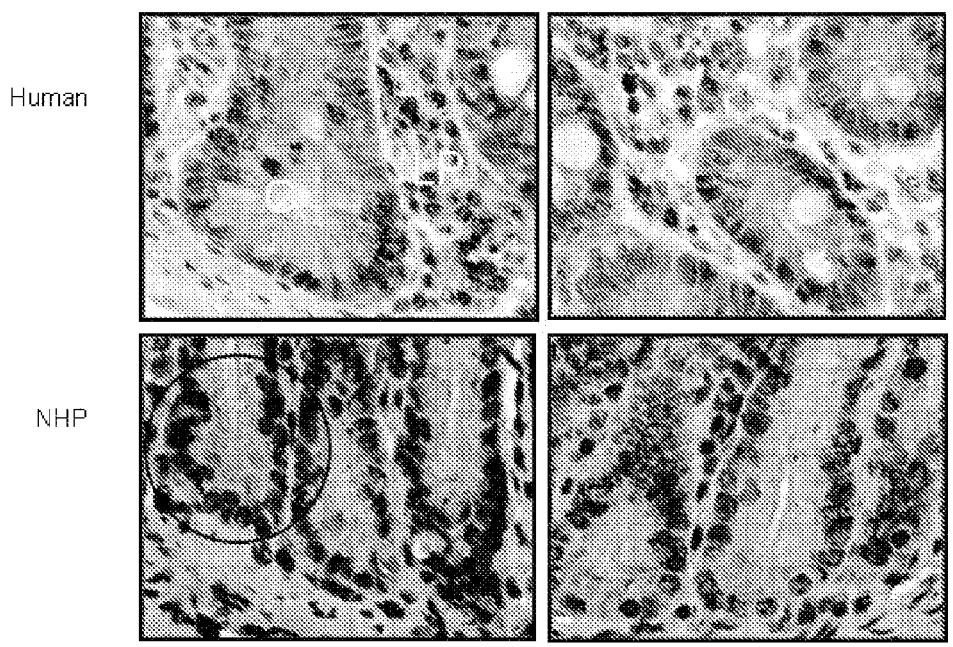
FIG. 11B is a series of photomicrographs of jejunum/ilium from non-human primate (NHP) or human, stained for IL-12Rβ2.

In the small intestine, IL-12Rβ2 was most commonly expressed in crypts (FIG. 11B). It is not known if IL-12Rβ2-expression in the intestinal crypt is localized to Paneth cells, multipotent stem cells, or both. IL-12Rβ2 expression was also noted in lymphoid cells populating the lamina propria and submucosal regions (FIG. 11B). Mucin secreting goblet cells did not express IL-12Rβ2. Both crypt and lamina propria IL-12Rβ2-expressing cells represent multifunctional mesenchymal-origin myofibroblasts that can serve as crypt shape-forming cells that also occupy both a stem cell niche and act as non-professional antigen presenting cells to immunomodulatory cells in the lamina propria.

Example 10

Effect of IL-12 Administration on Non-Human Primate Survival Following Irradiation The percentage of survival of rhesus monkeys exposed to an LD50/30 of total body irradiation (TBI) (6.7 Gy; 40 monkeys studied) was determined following subcutaneous administration of 100 ng/Kg or 250 ng/Kg of recombinant human IL-12 (rHuIL-12). The dosages of rHuIL-12 were administered at 24 hours post-TBI as well as both 24 hours and 7 days post-TBI. The study was conducted in the absence of any supportive care, including antibiotics. The doses of rHuIL-12 were chosen based on PK/PD studies in rhesus monkeys and were equivalent to rMuIL-12 doses of 8 ng/mouse and 20 ng/mouse, respectively. Animals were monitored for survival up to 30 days. One animal was excluded from the study due to a broken tooth.

Figure 12A:
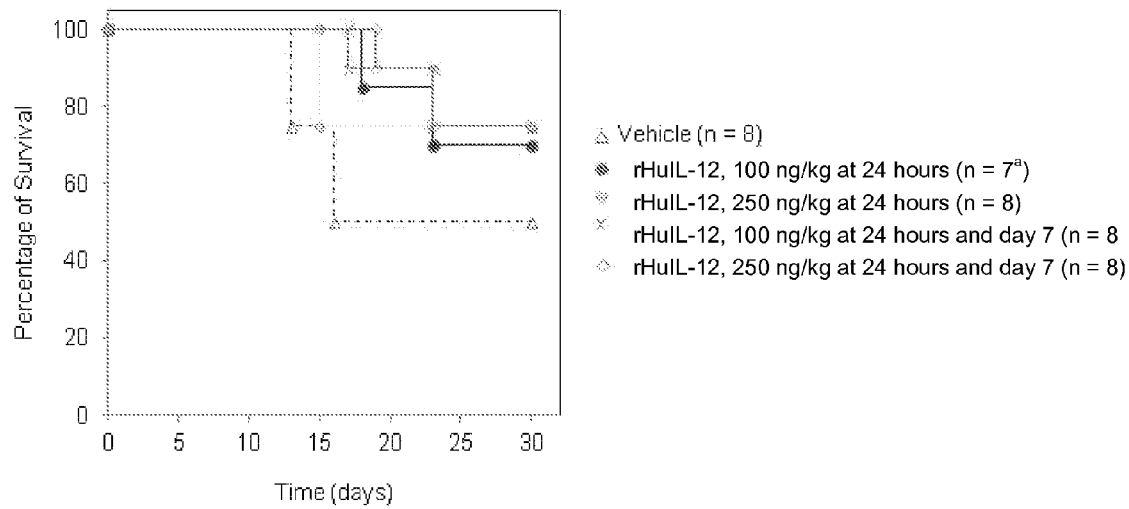
FIG. 12A is a Kaplan-Meier plot of survival data for individual dosing groups of monkeys after receiving IL-12 either 24 hours following total body irradiation, or at both 24 hours and 7 days following total body irradiation, as described in Example 10.
Figure 12B:
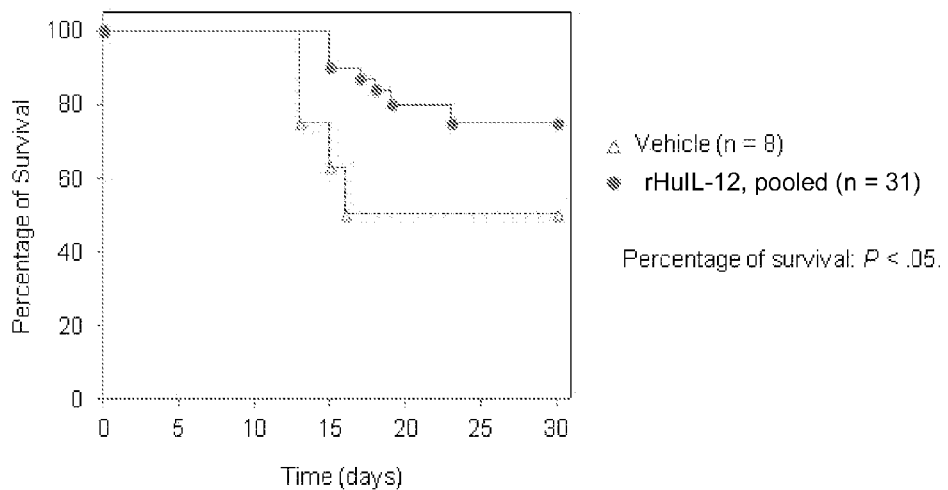
FIG. 12B is a Kaplan-Meier plot of survival data for pooled data from FIG. 12A.

As is depicted in FIG. 12A, rHuIL-12 at both doses, following either single or two administrations, mitigated death due to irradiation to the same extent. In each of the rHuIL-12-treated groups, survival increased by 21% for mice receiving 100 ng/kg rHuIL-12 at 24 hours, and 25% over control for all other treatment groups. Overall percentages of survival were 71% in the 100 ng/Kg single dose group (n=7) and 75% in all other groups receiving rHuIL-12 (n=8) compared to 50% in the vehicle group. Between-group differences in percentage of survival were not statistically significant, most likely because of the small number of animals in each group (n=8), but also because both rHuIL-12 doses were likely within the efficacious dose range. However, analysis of the percentage of survival regardless of the rHuIL-12 dosing regimen indicated that when pooled together, monkeys treated with rHuIL-12 had significantly higher percentage of survival than those receiving vehicle (75% vs. 50%, respectively; P=0.05) (FIG. 12B).

Example 11

Effect of IL-12 Administration on Blood Cell Counts of Non-Human Primates Following Irradiation Rhesus monkeys were treated as described in Example 10. Blood samples were withdrawn from the monkeys at various times, and leukocytes and platelets (thrombocytes), were counted by an automated hematology analyzer. Three analyses were conducted to assess differences in blood cell counts between the treated and control groups during the study period.

In one analysis, blood cell counts were analyzed from day 1 up to day 30 following irradiation. Monkeys treated with rHuIL-12 had significantly higher numbers of leukocytes and platelets at days 12 and 14, around the day of maximum decrease in blood cell counts ("nadir"), for the 100 ng/Kg and 250 ng/Kg doses, as compared to animals treated with vehicle (FIGS. 13A and 13B).

In a second analysis, blood cell counts were analyzed from day 1 up to day 14, the day before any animals died. Monkeys treated with rHuIL-12 had higher platelets counts compared to animals treated with vehicle (P=0.079 for the 250 ng/Kg group and P=0.02 for the 100 ng/Kg twice dosing group) during nadir (days 12 to 14). Additionally, in comparison to the vehicle group, animals treated with rHuIL-12 had significantly higher counts of leukocytes (P<0.01 for the 250 ng/Kg group and P<0.04 for the 100 ng/Kg twice dosing group) and reticulocytes (P<0.04 for the 250 ng/Kg group and P<0.001 for the 100 ng/Kg group) during nadir (days 12 to 14). The same trend was apparent for neutrophil, basophil, and lymphocyte counts, but those counts did not reach acceptable levels of statistical significance.

In a third analysis, the number of animals that reached dangerously low platelet counts during the study was assessed. This analysis revealed a difference between the vehicle and rHuIL-12-treated groups in the number of platelet counts dropping below a threshold level of 20,000 platelets/μL, a level generally necessitating platelet transfusion. In the rHuIL-12 250 ng/Kg group, only 4 out of 16 (25%) platelet counts at the nadir (day 12 to day 14) dropped below the transfusion threshold of less than 20,000 platelets/4, whereas 12 out of 15 (80%) platelet counts for the vehicle animals were below the threshold level during the same period of time (P=0.007).

Figure 13A:
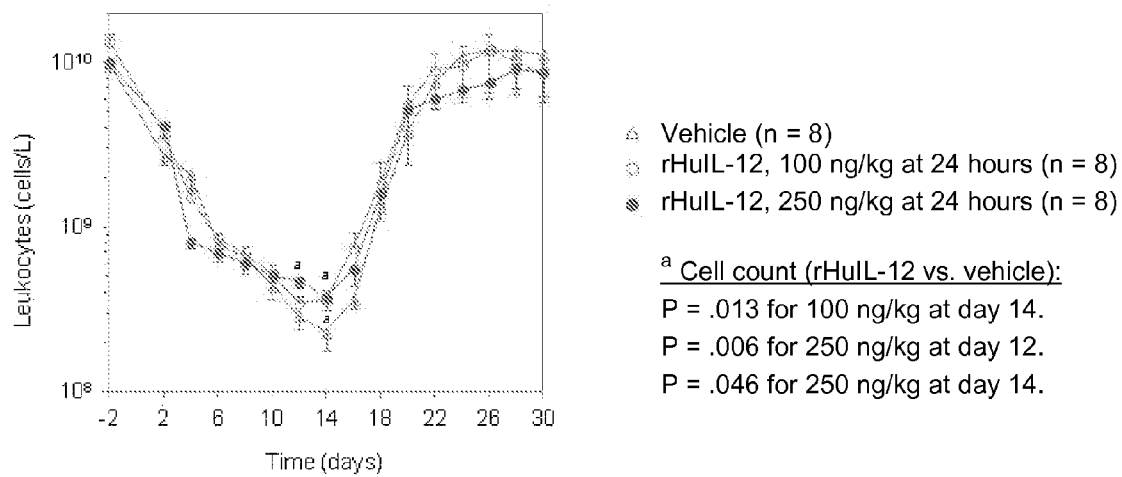
FIG. 13A is a graph of leukocyte counts from monkeys following irradiation and treatment with IL-12, as described in Example 11.
Figure 13B:
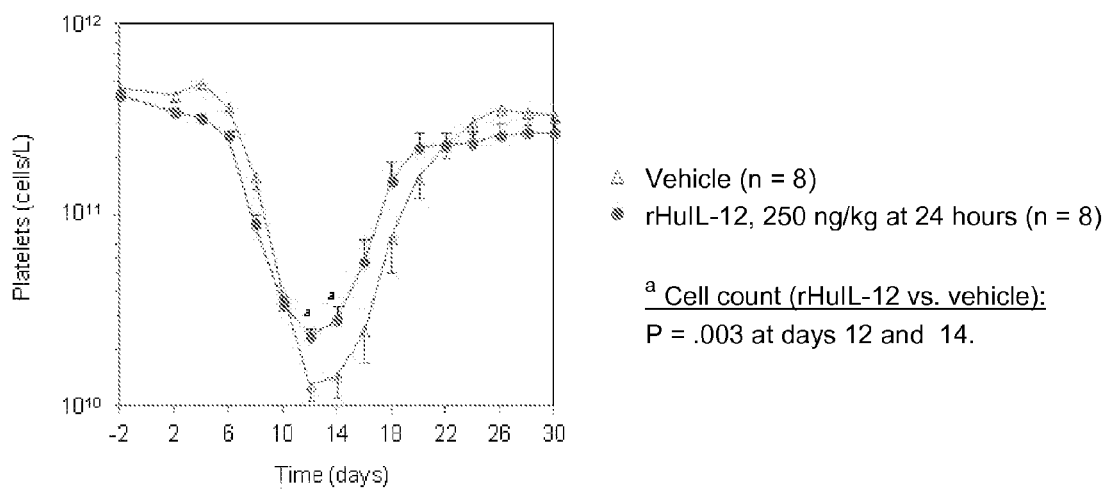
FIG. 13B is a graph of platelet counts from monkeys following irradiation and treatment with IL-12 as described in Example 11.

Taken altogether, these analyses show that rHuIL-12 increases leukocytes, platelet, and reticulocyte counts just prior to the days on which animals begin to die from radiation toxicity (day 13, FIG. 13A). Interestingly, vehicle-treated animals that survived up to day 30 also had quick recovery of blood cell counts, which were statistically indistinguishable from those in the rHuIL-12 groups. These findings demonstrate that mortality occurs in animals which do not show a strong blood cell recovery around the nadir days. The finding was confirmed by comparing blood cell counts of animals stratified by the mortality status, i.e. those surviving up to day 30 versus animals dying after day 12. In this analysis, the blood cell counts on the day before death was taken for animals that died after day 12. The comparison day for the surviving animals in each group was the average day on which the decedents in a particular group died (days 14 to 18). This analysis demonstrated that, regardless of the particular treatment group, animals surviving up to day 30 had significantly higher counts of platelets, neutrophils, leukocytes, reticulocytes, and lymphocytes than those that died after day 12 (P<0.001 to P<0.05). When compared by treatment group, animals treated with 100 ng/Kg rHuIL-12 had significantly higher counts of neutrophils, leukocytes, and lymphocytes than did those treated with vehicle in both survivors and decedent groups (P<0.001 for all three cell types). In addition, animals treated with 100 ng/Kg rHuIL-12 had a numerically higher platelet and reticulocyte counts. These findings demonstrate that rHuIL-12-induced increases in blood cell counts around nadir play a role in promoting survival following radiation exposure.

Example 12

Marker Expression on IL-12Rβ2+ Human Hematopoietic Stem Cells

Methods

Isolation of Lineage Marker-Depleted Cells: Human bone marrow was obtained from Lonza (Walkersville, Md.). Cells were diluted with MACS buffer (Miltenyi Biotec; Auburn, Calif.) and filtered through a 70 μm cell strainer (VWR; San Francisco, Calif.) to remove cell clumps. 35 ml of the cell suspension was layered over 15 ml of Ficoll-Paque (GE Lifesciences; Piscataway, N.J.) and centrifuged at 445 g for 35 minutes at 4° C. to separate bone marrow mononuclear cells. The mononuclear fraction was collected, diluted with MACS buffer and centrifuged at 200 g for 10 minutes to remove platelets. The cell pellet was resuspended in MACS buffer and incubated with monoclonal antibodies specific for lineage markers (Miltenyi Biotec; Auburn, Calif.). Lineage marker positive cells were removed by magnetic bead depletion. Lineage depleted cells (Lin⁻) were analyzed by flow cytometry. CD34+ cells, purified from human bone marrow were purchased from Lonza (Walkersville, Md.).

Flow Cytometric Analysis: Human bone marrow Lineage negative (Lin⁻) cells purified by immunomagnetic selection were washed in DPBS (Invitrogen; Carlsbad, Calif.). Cells were incubated with labeled antibodies against human IL-12Rβ2-APC (allophycocyanin label; R&D systems; Minneapolis, Minn.) and against CD34-PE (phycoerythrin label; BD Biosciences; San Jose, Calif.) for 30 minutes at room temperature. Next, cells were washed twice and suspended in DPBS and analyzed on a MoFlow flow cytometer (Beckman Coulter, Inc./Dako, Inc.). The appropriate isotype controls were included for each experiment. CD34+ cells were similarly labeled with antibodies against CD34-PE and IL-12Rβ2-APC. In select studies, cells were selected for IL-12Rβ2 and CD34 markers by cell sorting.

Immunocytochemical Analysis of CD34+ Cells: CD34+ cells obtained from Lonza were fixed on slides treated with 5 μg/ml fibronectin. Cultures were fixed in cold methanol for 10 minutes at −20° C. and blocked with Background Sniper (Biocare Medical, Concord, Calif.) for 15 minutes. Cells were labeled with a rabbit polyclonal antibody against IL-12Rβ2 (Sigma) and incubated at room temperature for 2 hours, followed by incubation with ImmPRESS reagent anti-rabbit IgG Peroxidase (Vector Laboratories, Burlingame, Calif.). Slides were incubated with ImmPACT AEC Peroxidase Substrate (Vector Laboratories, Burlingame, Calif.) for 30 minutes and counterstained in Hematoxylin. The negative control included cells fixed and treated with the same reagents without the primary rabbit polyclonal antibody. Photographs were taken using an Olympus camera in combination with analysis software.

Results

Figure 14A:
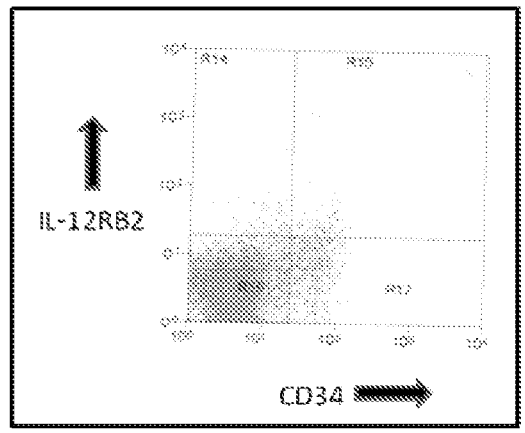
FIG. 14A is a plot of flow cytometry data for lineage marker-depleted human bone marrow cells labeled for IL-12Rβ2 and CD34, as described in Example 12. The quadrants were set based on unstained and isotype controls. R14=IL-12Rβ2$^+$CD34$^-$, R15=IL-12Rβ2$^+$CD34$^+$, R17=IL-12Rβ2$^-$CD34$^+$.
Figure 14B:
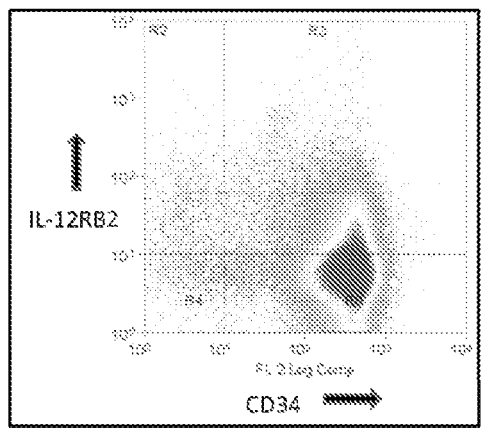
FIG. 14B is a plot of flow cytometry data for lineage marker-depleted human bone marrow cells labeled for IL-12Rβ2 and CD34. The quadrants were set based on unstained and isotype controls. R2=IL-12Rβ2$^+$CD34$^-$, R3=IL-12Rβ2$^+$CD34$^+$, R5=IL-12Rβ2$^-$CD34$^+$.

To determine if human hematopoietic stem cells (HSCs) expressed IL-12Rβ2, Lineage depleted (Lin⁻) cells were isolated from human bone marrow and stained with antibodies to IL-12Rβ2 and CD34 to quantify the expression of IL-12Rβ2 by flow cytometry. Approximately 1-2% of Lin⁻ cells from human bone marrow expressed IL-12Rβ2 (FIG. 14A). These Lin⁻ IL-12Rβ2+ comprised approximately 0.2% of the total bone marrow. Approximately 6-50% of Lin⁻CD34+ expressing cells were positive for IL-12Rβ2 (FIG. 14B). The range of IL-12Rβ2 co-expression of CD34+ cells was observed to be donor dependent.

Figure 14C:
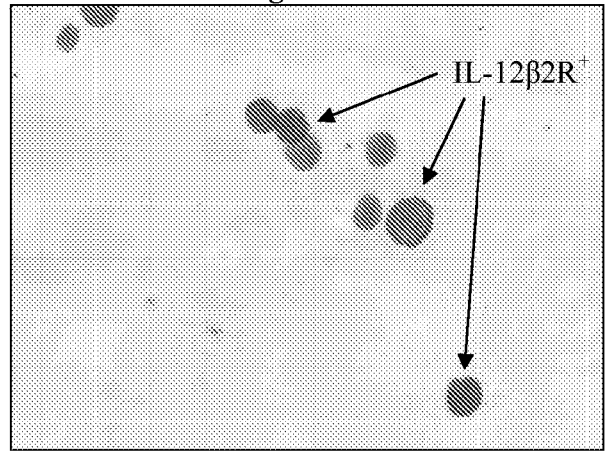
FIG. 14C is a photomicrograph of CD34$^+$ cells stained for IL-12Rβ2.

The flow cytometry results were supported by immunocytochemical staining of CD34+ cells from human bone marrow for IL-12Rβ2 using a different antibody to IL-12Rβ2 than was used for flow cytometry. As shown in FIG. 14C, IL-12Rβ2 is expressed on CD34+ hematopoietic stem/progenitor cells from human bone marrow.

Figure 15A:
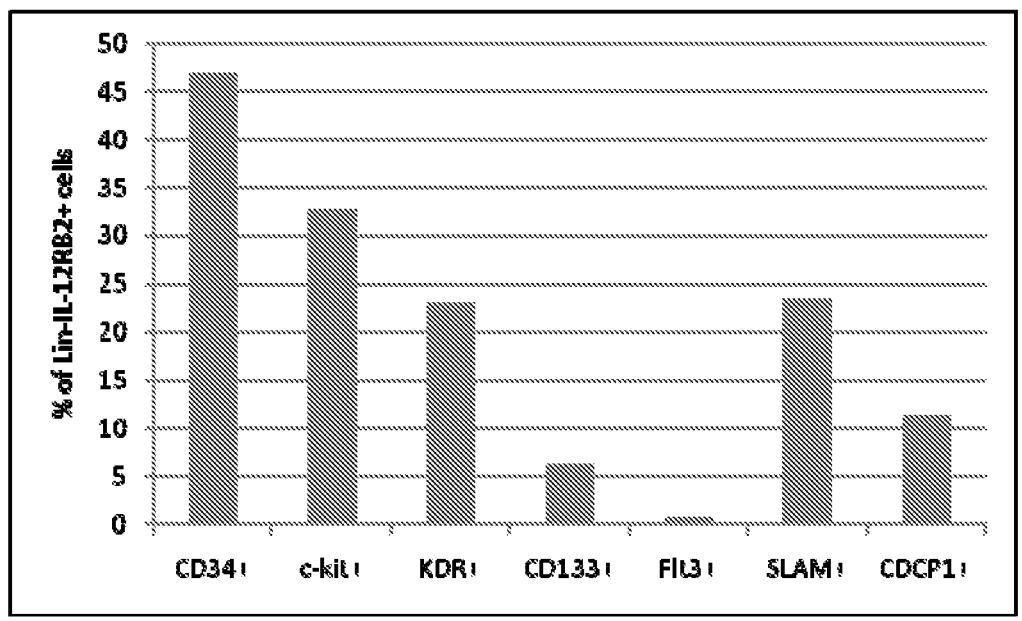
FIG. 15A is a bar graph showing percentages of human lineage marker-depleted, IL-12Rβ2-expressing cell subsets that co-express with the hematopoietic stem cell (HSC) markers CD34, ckit, KDR, CD133, Flt3, SLAM and CDCP1, as described in Example 12.
Figure 15B:
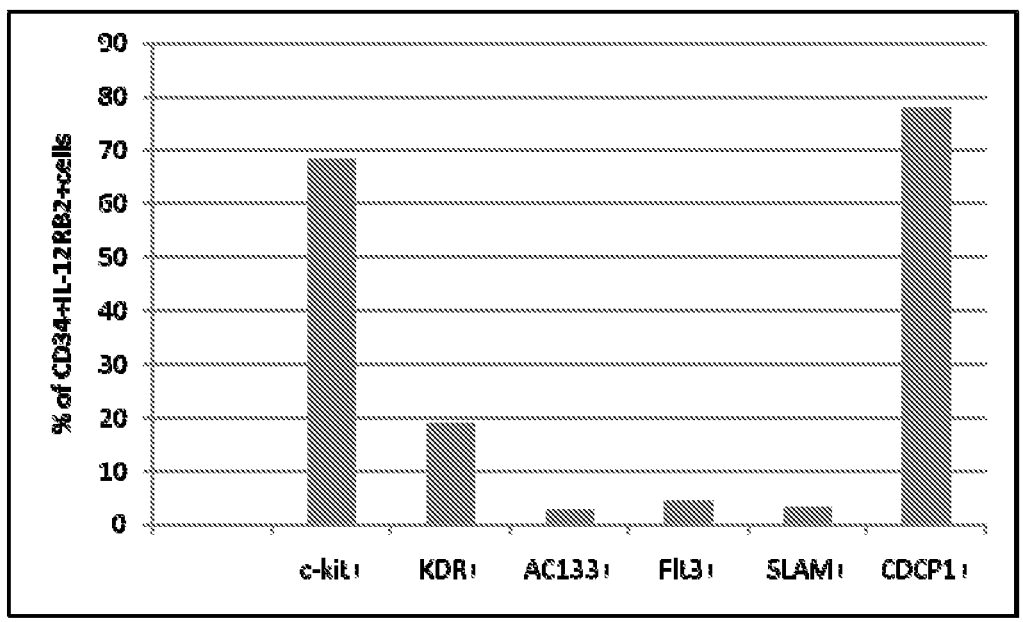
FIG. 15B is a bar graph showing percentages of human CD34$^+$, IL-12Rβ2-expressing cell subsets that co-express with HSC markers CD34, ckit, KDR, CD133, Flt3, SLAM and CDCP1.

To analyze the co-expression of IL-12Rβ2 with other hematopoietic stem cell markers, lineage depleted and CD34+ cells from human bone marrow were labeled with antibodies to IL-12Rβ2 and the hematopoietic stem cell markers CD34, ckit, KDR, CD133, Flt-3, SLAM and CDCP1 and analyzed by flow cytometry. FIG. 15A shows the percentage of lineage depleted, IL-12Rβ2 expressing cells co-expressing above mentioned HSC markers. Approximately 46% of lineage depleted, IL-12Rβ2 expressing cells co-expressed CD34. Similarly, c-kit, KDR, CD133, Flt3 and SLAM were associated with IL-12Rβ2 expressing cells. FIG. 15B shows the percentage of CD34+ IL-12Rβ2 expressing cells co-expressing HSC markers. Approximately 70% of CD34+ IL-12Rβ2 expressing cells co-expressed c-kit and up to 80% of the CD34+IL-12Rβ2+ population expressed CDCP1. A smaller percentage of this population was associated with markers such as KDR, CD133, Flt3 and SLAM. The frequency of subpopulations within IL-12Rβ2 is listed in Table 6 below.

TABLE 6

Frequency of subpopulations within Lin− IL-12Rβ2+ and CD34+ IL-12Rβ2+ cells

| Subpopulation phenotype | Lin− IL-12Rβ2+ | CD34+ IL-12Rβ2+ |
| --- | --- | --- |
| CD34 | 46-55 | 94.84 |
| ckit | 40-55 | 68.12 |
| KDR | 34-36 | 18.81 |
| CD133 | 6.2 | 2.89 |
| Flt3 | 0.7 | 4.29 |
| SLAM | 23.3 | 3.03 |
| CDCP1 | 6 | 77.85 |

Example 13

Effect of Exogenous IL-12 on CD34+ Hematopoietic Stem Cells

Methods

Culture and Stimulation of CD34+ Cells with IL-12:

CD34+ cells obtained from Lonza (Walkersville, Md.) were thawed and washed in 0.1% BSA/DPBS. They were centrifuged at 300 g for 10 minutes and pellet was resuspended in IMDM/10% FBS containing BD Golgi Plug, Brefeldin A (BD Biosciences). Cultures were stimulated with 10 pM IL-12 or media and incubated for 24 hours at 37° C. in a humidified incubator. Cells were harvested, resuspended in Fixation/Permeabilization buffer (BD Biosciences) and incubated at 4° C. for 20 minutes. The cells were then washed in BD Perm/Wash buffer and resuspended in DPBS. Cells were labeled with antibodies to CD34 and IL-12Rβ2 and incubated for 30 minutes at room temperature, then washed and analyzed by flow cytometry. The results were compared to unstained and isotype controls.

Clonogenic Progenitor Assay:

Human lineage depleted bone marrow cells, selected for IL-12Rβ2 and CD34 were plated at a concentration of 3200 cells onto 35 mm cell culture dishes in methylcellulose medium containing 1% methylcellulose, 30% fetal bovine serum, 1% BSA, 10-4 M 2-mercaptoethanol, 2 mM L-glutamine, 50 ng/ml recombinant stem cell factor (SCF), 10 ng/ml GM-CSF, 10 ng/ml and 3 µg/ml recombinant erythropoietin (Epo) (Stem Cell Technologies). Cultures were supplemented with varying concentrations of IL-12 or media alone and incubated at 37° C., in 5% $CO_2$, with at least 95% humidity. CFU-GEMM colonies were scored on Day 8 by morphological analysis using an inverted microscope.

Results

Figure 16:
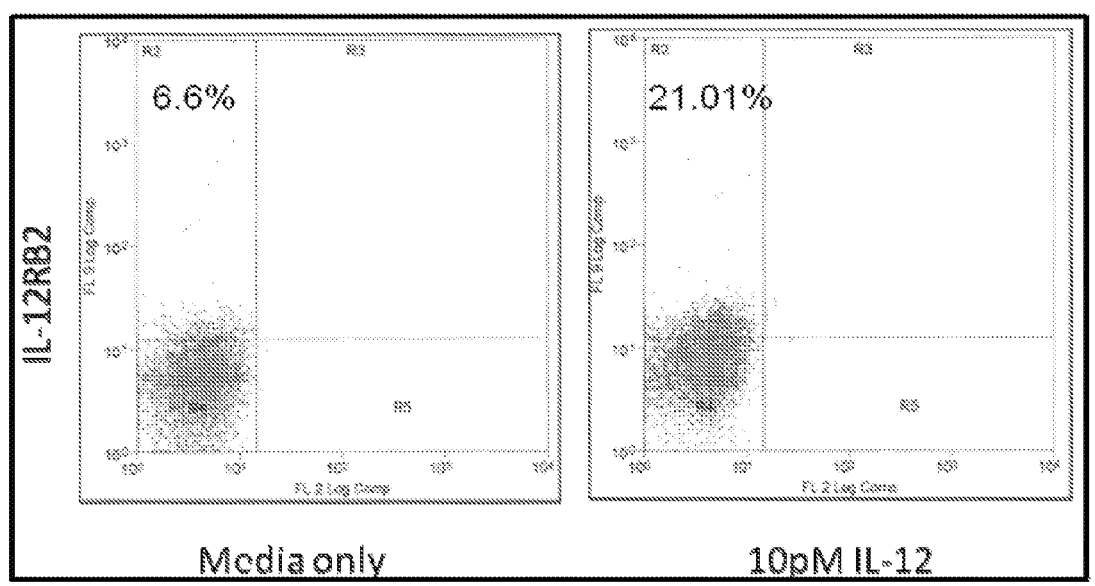
FIG. 16 shows plots of flow cytometry data for expression of intracellular IL-12Rβ2 in human bone marrow CD34$^+$ cells cultured in media alone (left panel) or in the presence of 10 pM IL-12 (right panel), as described in Example 13.

To determine if IL-12 acts directly on hematopoietic stem/progenitor cells, CD34+ cells from human bone marrow were cultured with IL-12 or media alone in the presence of Brefeldin A for 24 hours. Cells were harvested, fixed and permeabilized. Next, cells were labeled with antibodies to IL-12Rβ2 to quantify intracellular IL-12Rβ2 expression by flow cytometry analysis. Approximately 6% of CD34+ cells from human bone marrow expressed IL-12Rβ2. Following stimulation with IL-12, IL-12Rβ2 expression increased 3 fold to 21% (representative analysis shown in FIG. 16).

Figure 17A:
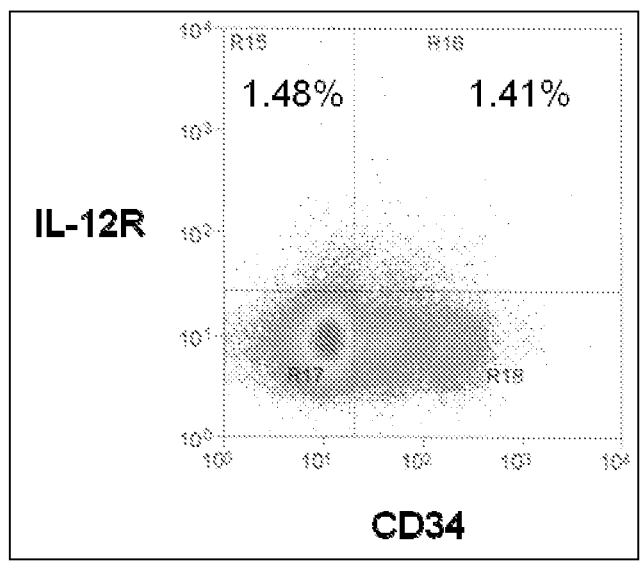
FIG. 17A shows plots of flow cytometry data for expression of cell surface IL-12Rβ2 and CD34 on human bone marrow Lin$^-$ cells, as described in Example 13. The quadrants were set based on unstained and isotype controls. R14=IL-12Rβ2$^+$CD34$^-$, R15=IL-12Rβ2$^+$CD34$^+$.
Figure 17B:
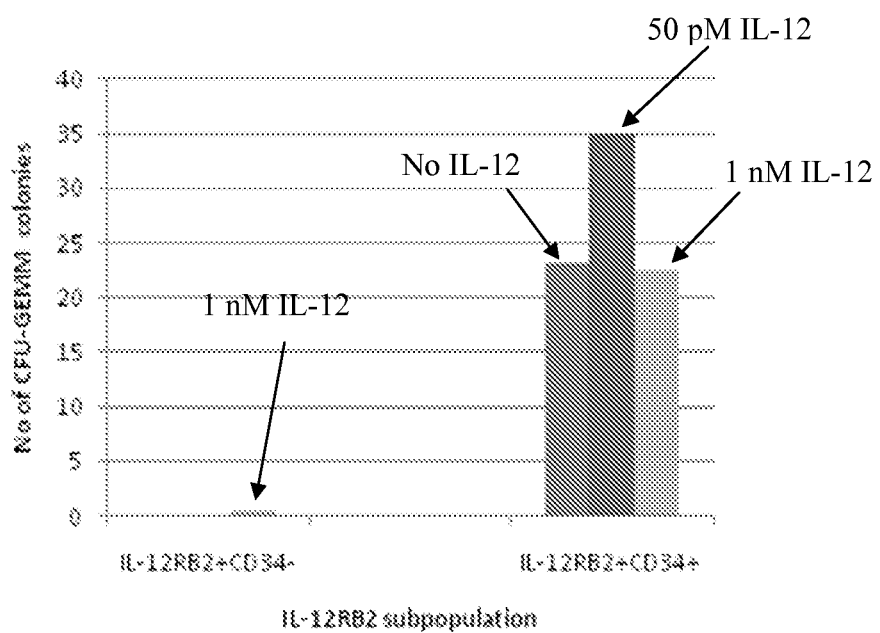
FIG. 17B shows a bar graph of data for amount of CFU-GEMM colony formation in IL-12Rβ2$^+$CD34$^-$ and IL-12Rβ2$^+$CD34$^+$ cultures with and without IL-12 stimulation on Day 8 of culture, as described in Example 13.

To test the clonogenic potential of IL-12Rβ2+CD34+ cells, lineage negative cells isolated from human bone marrow were labeled with antibodies to IL-12Rβ2 and CD34. Cells were sorted to obtain two IL-12Rβ2 expressing populations: 1) IL-12Rβ2+CD34+ and 2) IL-12Rβ2+CD34− (FIG. 17A). Each of these populations was plated in methylcellulose cultures with or without IL-12 stimulation and examined for colony forming units of myeloid cells (CFU-GEMM). CFU-GEMM colonies were counted on Day 8 of culture. The colony forming potential of cultures stimulated with IL-12 was compared to the unstimulated control. IL-12Rβ2+CD34− cells failed to form any colonies. One CFU-GEMM colony observed in IL-12Rβ2+CD34− cultures stimulated with 1 nM IL-12 could be attributable to contamination during sorting (FIG. 17B). Interestingly, an increase in CFU-GEMM colony formation was observed in cultures stimulated with 50 pM IL-12. Increasing the IL-12 concentration to 1 nM resulted in inhibition of CFU-GEMM colony formation. A clear correlation exists between IL-12 stimulation and colony growth. However, colony numbers and types were variable and highly donor-dependent.

Human bone marrow lineage-depleted cells could be further subdivided into two subsets based on their forward and side scatter as shown in FIGS. 18A and 18B. Both of these populations together give CFU-GEMM colonies along with some more committed colony types. Interestingly, lineage depleted cells from one specific donor appeared to be deficient in one subset (FIG. 18B). Lin−IL-12Rβ2+CD34+ cells from this donor gave only BFU-E colonies along with some committed progenitors, but no CFU-GEMM colonies. This shows that both subsets of the lineage-depleted population were essential for generation of CFU-GEMMs.

Example 14

Therapeutic Application of the IL-12R+ Stem Cell

The Examples above show that the IL-12R+ stem cell has survival related properties in generating hematopoiesis following a lethal radiation assault. The property of transdifferentiation has been attributed to the hematopoietic stem cells. Thus, given the survival related properties of the IL-12 stem cell, this cell can be used for repair and regeneration of tissue of various types other than blood.

For autologous stem cell repair and regeneration, the IL-12R+ stem cells are isolated as described in example 7. The IL-12 ligand is given to the patient prior to bone marrow or peripheral blood harvest of cells. Generally bone marrow is preferred as the source of blood cells for harvest. Whether or not the IL-12 ligand is given to the patient, the next step is to select cells using an appropriate antibody that are positive for the IL-12 receptor. In a preferred embodiment, a lineage positive depletion step is performed first which would yield lineage negative cells to use as the blood cell population for selection of the IL-12 receptor. Further refinement of the IL-12R+ stem cell population is made using various antibodies, such as CD34, CD133, Kit, HSMI, FIt3R, IFNGR, TpoR, CD38, Angiotensin(1-7)R, CCR, CXCR and the like. Secondary marker choice may differ depending on the type of tissue in need of repair. Following isolation of the IL-12R+ stem cell, the cells can be cryogenically frozen, but it is preferred that the cells be used without freezing as soon as possible following harvest. Then these cells can be transplanted back to the patient.

For example, in the case of a hematopoietic stem cell transplant, following harvest and isolation of the a population of IL-12R$^+$ cells, the patient undergoes myeloablation and then receives the IL-12R$^+$ stem cells with or without other carrier cells, which are blood cells in this case. An effective dose of the IL-12 ligand may also be given immediately following transplantation. An effective dose of the IL-12 ligand is generally 500 ng/kg or less. Also following the HSC transplant, the patient may be given an effective dose of the IL-12 ligand. The post-transplant administration of the IL-12 ligand could be done one or more times post-transplantation. It is preferred that the IL-12 ligand not be given for longer than 1 week post-transplant. During long-term recovery from the transplant, the patient may periodically be given a dose of the IL-12 ligand as needed.

For autologous liver repair and regeneration, the above described method is followed. Liver specific stem cell markers are used as secondary markers of the IL-12R$^+$ stem cell. In the case of liver repair and regeneration, a population of IL-12R$^+$ stem cells are injected into the liver, with or without radiation specifically to the liver prior to transplantation. Once in the liver, the IL-12R$^+$ stem cells facilitate repair and regeneration of the liver. Under these conditions, the IL-12R$^+$ cells undergo transdifferentiation to generate hepatocytes. The IL-12 ligand may or may not be given to the patient following transplantation. It is preferred however that the IL-12 ligand is administered for some time period following transplantation. In a similar manner, cardiac, kidney, pancreas, lung tissue, or the like can repaired and regeneration via transplantation of the IL-12R$^+$ stem cells, with or without administration of the IL-12 ligand.

For allogeneic repair and regeneration of tissue, a population of IL-12R$^+$ stem cells is derived from a healthy person who is not the patient. Selection of a suitable donor is made in the manner generally use for finding closely matched donor and recipient pairs. In the case of allogeneic use of the IL-12R$^+$ stem cell, IL-12R$^+$ stem cells that lack one or more major histocompatibility markers (MHC) on the cell surface are selected. Following selection of the IL-12R$^+$ stem cell population, antibodies to various MHC are used to select for a cell population that is IL-12R$^+$ and MHC negative. This population is preferred for allogeneic transplantation for tissue repair and regeneration of bone marrow, liver, cardiac, kidney, pancreas, lung tissue or the like.

Example 15

Reconstitution of Hematopoietic System in Mice using IL-12

Studies were conducted to compare IL-12 administration to the use of HSCT (healthy bone marrow cells) in generating hematopoietic recovery in lethally irradiated mice. All mice received an acute dose of lethal radiation (8 Gy). One group of lethally irradiated mice received IL-12 administered as a split-dose at both 24 hours before and 48 hours after irradiation. Another group of lethally irradiated mice received a bone marrow transplant of 1×10$^6$ healthy bone marrow cells.

Figure 19:
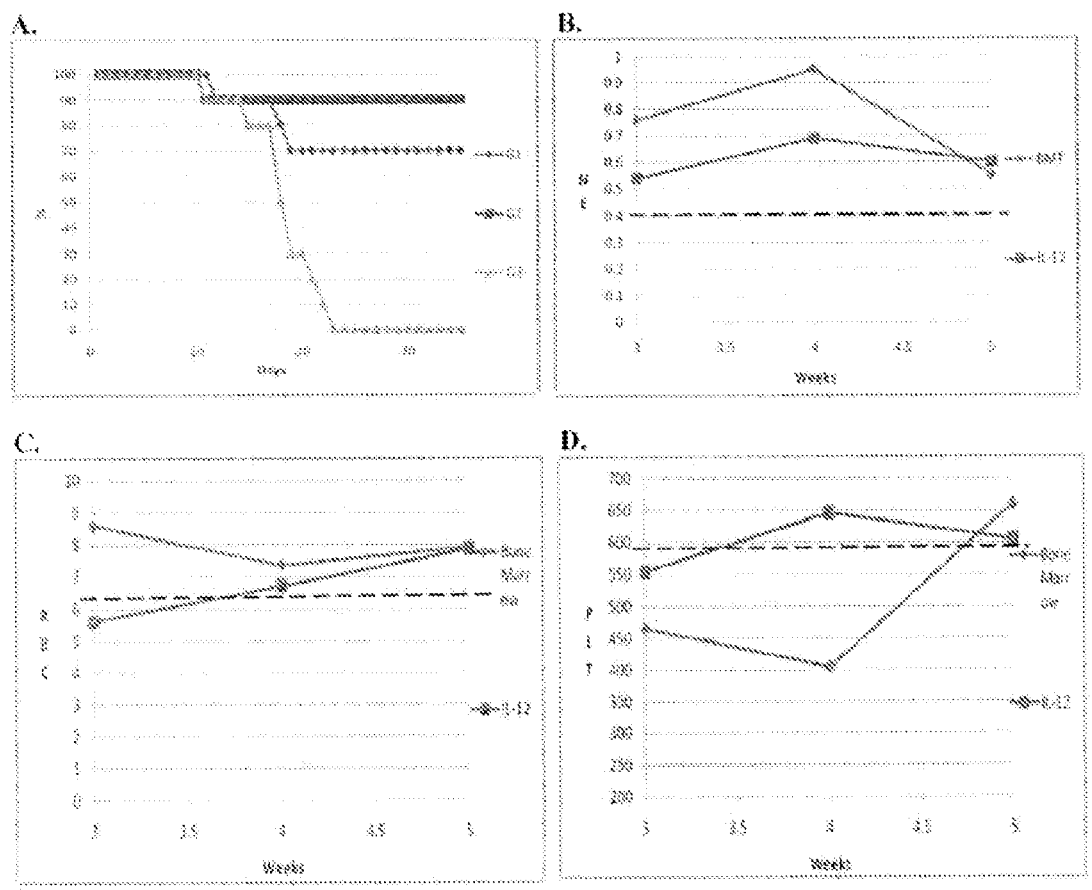
FIG. 19 shows survival data and cell count data from mice treated either with IL-12 or bone marrow transplant twenty four hours following lethal irradiation, as described in Example 15.

Data from this study show that IL-12 alone recapitulates the hematopoietic recovery equal to that of a bone marrow transplant in both its kinetic and blood cell parameters. The survival rate of IL-12 treated mice at 21 days (about 70%) is similar to that of mice receiving a bone marrow transplant (about 90%; FIG. 19A). IL-12 treated mice had above normal neutrophil counts at 21 days (FIG. 19B), red blood cell counts near the normal range at 21 days (FIG. 19C), and platelet recovery in the normal range and above that of bone marrow transplant recipients (FIG. 19D).

Figure 20A:
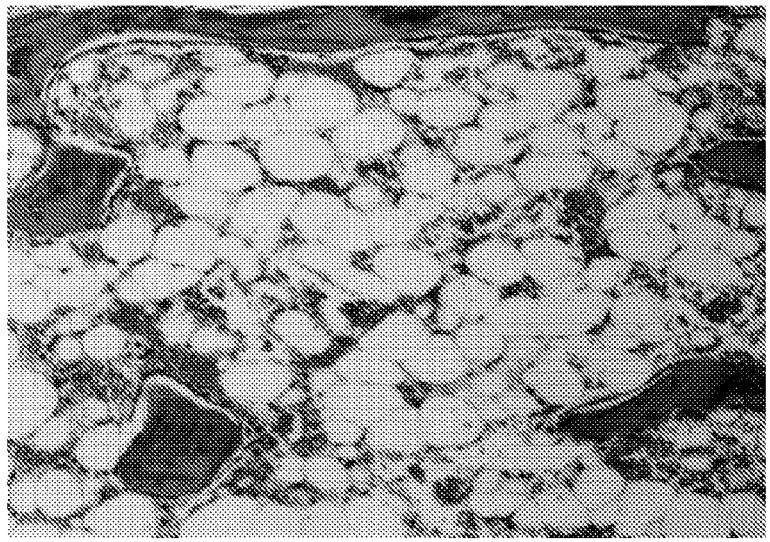
FIGS. 20A and 20B show photomicrographs of bone marrow from mice following lethal irradiation as described in Example 15 (FIG. 20A control.
Figure 20B:
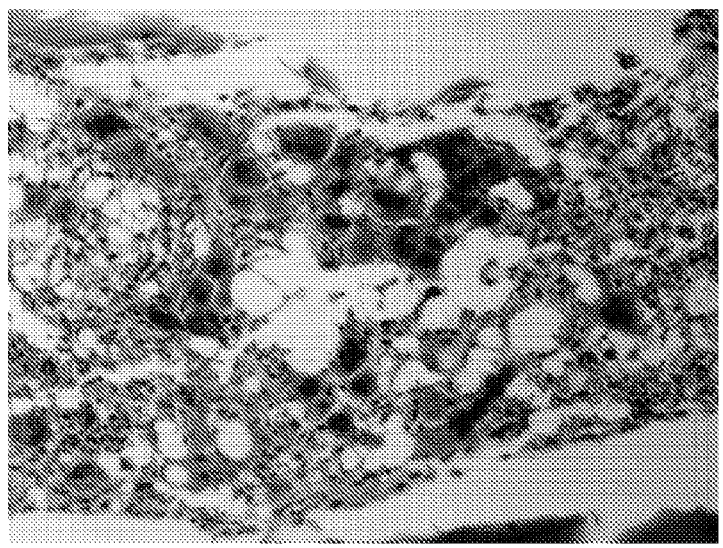

FIG. 20A shows a photomicrograph of bone marrow from an irradiated control mouse at 12 days post-irradiation. No cells are seen in the bone marrow, typical of "empty marrow" seen in acute radiation syndrome. In contrast, bone marrow from an IL-12 treated mouse at 12 days post-irradiation (FIG. 20B) contains megakaryocytes and foci of regeneration (progenitors cells).

Example 16

IL-12 Treatment in Mice at Three Different Radiation Doses

Figure 21A:
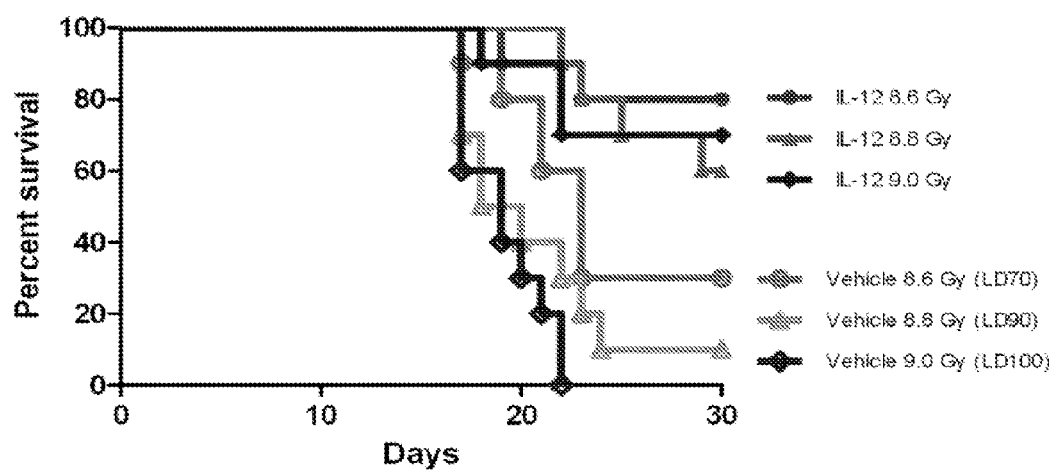
FIG. 21A shows a Kaplan-Meier survival plot of mice that received various doses of radiation, followed by a single dose of IL-12 twenty four hours following irradiation as described in Example 16.

Mice (n=10) were exposed to 8.6, 8.8 and 9.0 Gy doses of lethal irradiation which corresponded to LD70, LD90 and LD100, respectively. Twenty four hours following radiation exposure, 20 ng/mouse of rMuIL-12 was administered subcutaneously and the mice were monitored for 30 day survival. FIG. 21A shows the Kaplan-Meier survival plots for the vehicle control and rMuIL-12 treated mice for each of the three radiation doses.

rMuIL-12 administration yielded a similar statistically significant increase in percent survival at each radiation dose. For the experimental data depicted in FIG. 21A, rMuIL-12 administration yielded statistically significant increases in percent survival at each radiation dose (via Kaplan-Meier analysis, ($p<0.05$-0.001 for increasing radiation doses; via chi squared (Fisher Exact) analysis, $p<0.05$ for all radiation doses). The efficacy of rMuIL-12 does not decrease with increasing radiation exposure within the range of hematopoietic syndrome. Moreover, the radiomitigation effects of rMuIL-12 actually seem to increase with increasing levels of radiation exposure. This observation suggests that rMuIL-12 can ameliorate the gastrointestinal (GI) damage that is coincident with hematopoietic injury at higher radiation exposure.

Example 17

Figure 21B:
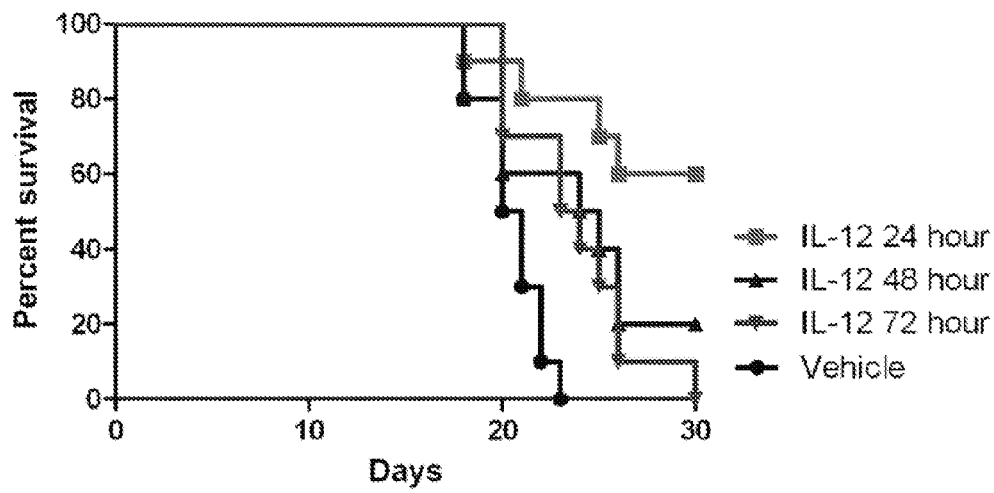
FIG. 21B shows a Kaplan-Meier survival plot of mice that received a single dose of irradiation followed by a single dose of IL-12 at various times following irradiation as described in Example 17.

IL-12 Treatment in Mice at Three Different Times Following Irradiation rMuIL-12 was administered subcutaneously (20 ng/mouse) to three groups of mice (n=10) at either 24, 48 or 72 hours after LD100 radiation exposure (9.0 Gy). The Kaplan-Meier survival plot is shown in FIG. 21B. The 24 and 48 hour administrations resulted in statistically significant increases in percent survival ($p=0.01$ for 24 hours and $p<0.03$ for 48 hours, chi square analysis (Fisher's Exact Test)) vehicle control ($p>0.05$, K-M analysis).

The present invention has been discussed in considerable detail with reference to certain preferred embodiments, although other embodiments are possible. Therefore, the scope of the appended claims should not be limited to the description of preferred embodiments contained in this disclosure. All references cited herein are incorporated by reference in their entirety.

The above examples are given to illustrate the present invention. It should be understood, however, that the spirit and scope of the invention is not to be limited to the specific conditions or details described in these examples. All publicly available documents referenced herein, including but not limited to U.S. patents, are specifically incorporated by reference.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

REFERENCES

1. Ogawa M. Differentiation and proliferation of hematopoietic stem cells. Blood. 1993; 81:2844-2853.
2. Williams D A. Ex vivo expansion of hematopoietic stem and progenitor cells-robbing Peter to pay Paul? [editorial]. Blood. 1993; 81:3169-3172.
3. Moore M A. Expansion of myeloid stem cells in culture. Semin Hematol 1995; 32:183-200.
4. Spangrude G J, Heimfeld S, Weissman I L. Purification and characterization of mouse hematopoietic stem cells [published erratum appears in Science. 1989, 244:1030]. Science. 1988; 241:58-62.
5. Jones R J, Wagner J E, Cenalo P, Zicha M S, Sharkis S J. Separation of pluripotent haematopoietic stem cells from spleen colony-forming cells [see comments]. Nature. 1990; 347:108-189.
6. Berardi A C, Wang A, Levine J D, Lopez P, Scadden D T. Functional isolation and characterization of human hematopoietic stem cells. Science. 1995; 267:104-108.
7. Kawashima I, Zanjani E D, Almaida P G, Flake A W, Zeng H, Ogawa M. $CD34^+$ human marrow cells that express low levels of Kit protein are enriched for long-term marrow-engrafting cells. Blood. 1996; 87:4136-4142.
8. Huang S, Terstappen L W. Lymphoid and myeloid differentiation of single human $CD34^+$, $HLADR^+$, $CD38^-$ hematopoietic stem cells. Blood. 1994; 83:1515-1526.
9. Kondo M, Wagers A J, Manz M G, Prohaska S S, Scherer D C, Beilhack G F, Shizuru J A, Weissman I L. Biology of hematopoietic stem cells and progenitors: implications for clinical application. Annu Rev Immunol. 2003; 21:759-806.
10. Zhao Y, Lin Y, Zhan Y, Yang G, Louie J, Harrison D E, Anderson, WF. Murine hematopoietic stem cell characterization and its regulation in BM transplantation. Blood. 2000; 96:3016-3022.
11. Alamo A L, Melnick S J. Clinical application of four and five-color flow cytometry lymphocyte subset immunophenotyping. Cytometry. 2000; 42:363-370.
12. Zhong I F, Zhao Y, Sutton S. Su A, Zhan Y, Zhu L, Yan C, Gallaher T, Johnston P B, Anderson W F, Cooke M P. Gene expression profile of murine long-term reconstituting vs. short-term reconstituting hematopoietic stem cells. Proc Natl Acad Sci USA. 2005; 102:2448-2453.
13. Park I K, He Y, Lin F, Laerum O D, Tian Q, Bumgarner R, Klug C A, Li K, Kuhr C, Doyle M J, Xie T, Schummer M, Sun Y, Goldsmith A, Clarke M F, Weissman I L, Hood L, Li L. Differential gene expression profiling of adult mouse hematopoietic stem cells. Blood. 2002; 99:488-498.
14. Terskikh A V, Easterday M C, Li L, Hood L, Komhlum H I, Geschwind D H, Weissman I L. From hematopoiesis to neuropoiesis: evidence of overlapping genetic programs. Proc Natl Acad Sci USA. 2001; 98:7934-7939
15. 1. Gluckman E, Rocha V, Bayer-Chammard A. et al. Outcome of cord blood transplantation from related and unrelated donors. Eurocord Transplant Group and the European Blood and Marrow Transplantation Group. N Engl J Med. 1997; 337:373-381.
16. Wagner J E, Rosenthal J, Sweetman R, et al. Successful transplantation of HLA-matched and HLA-mismatched umbilical cord blood from unrelated donors: analysis of engraftment and acute graft-versus-host disease. Blood. 1996; 88:795-802.
17. Rogers I, Sutherland Holt D, et al. Human UC-blood banking: impact of blood volume, cell separation and cryopreservation on leukocyte and $CD34^+$ cell recovery. Cytotherapy. 2001; 3:269-276.
18. Lobato da Silva C, Goncalves R, Crapnell K B, Cabral J M S, Zanjani E D, and Almeida-Porada G. A human stromal-based serum-free culture system supports the ex vivo expansion/maintenance of bone marrow and cord blood hematopoietic stem/progenitor cells. Exp. Hematol. 2005; 3:828-835.
19. Devine S M, Lazarus H M, Emerson S G. Clinical application of hematopoietic progenitor cell expansion: current status and future prospects. Bone Marrow Transplant. 2003; 31:241-252.
20. McNiece I, Jones R, Bearman S I, et al. Ex vivo expanded peripheral blood progenitor cells provide rapid neutrophil recovery after high dose chemotherapy in patients with breast cancer. Blood. 2000; 96:3001-3007.
21. Paquette R L, Dergham S T, Karpf E, et al. Ex vivo expanded unselected peripheral blood: progenitor cells reduce post transplantation neutropenia, thrombocytopenia, and anemia in patients with breast cancer. Blood. 2000; 96:2385-2390.
22. Reiffers J, Cailliot C, Dazey B, Attal M, Caraux J, Boiron J M. Abrogation of post-myeloablative chemotherapy neutropenia by ex vivo expanded autologous CD34-positive cells. Lancet. 1999; 354:1092-1093.
23. Lewis I D, Almeida-Porada G, Du J, et al. Umbilical cord blood cells capable of engrafting in primary, secondary, and tertiary xenogeneic hosts are preserved after ex vivo culture in a noncontact system. Blood. 2001; 97:3441-3449.
24. Barker J N. Davies S M. DeFor T. Ramsay N K, Weisdorf D J, Wagner J E. Survival after transplantation of unrelated donor umbilical cord blood is comparable to that of human leukocyte antigen-matched unrelated donor bone marrow: results of a matched-pair analysis. Blood. 2001; 97:2957-2961.
25. Wagner J E, Barker J N, DeFor T E, et al. Transplantation of unrelated donor umbilical cord blood in 102 patients with malignant and nonmalignant diseases: influence of CD34 cell dose and HLA disparity on treatment-related mortality and survival. Blood. 2002; 100:1611-1618.
26. Lazzari L, Lucchi S, Rebulla P, et al. Long-term expansion and maintenance of cord blood haematopoietic stem cells using thrombopoietin, Flt3-ligand, interleukin (IL)-6 and IL-11 in a serum free and stroma free culture system. Br J Haematol. 2001; 112:397-404.
27. Shpall E J, Quinones R, Giller R, et al. Transplantation of ex vivo expanded cord blood. Biol Blood Marrow Transplant. 2002; 8:368-370.
28. Barker J N, Weisdorf D J, DeFor T E, Blazar B R, Miller J S, Wagner J E. Rapid and complete donor chimerism in adult recipients of unrelated donor umbilical cord blood transplantation after reduced-intensity conditioning. Blood. 2003; 102:1915-1919.
29. Gluckman E, Broxmeyer H A, Auerbach A D, et al. Hematopoietic reconstitution in a patient with Fanconi's anemia by means of umbilical cord blood from an HLA-identical sibling. N Engl J Med. 1989; 321:1174-1178.
30. Madlambayan G J, Rogers I, Kirouac D C, Yamanaka N, Muzurier F, Doedens M, Robert Casper R F, Dick J E, and Zandstra P W. Dynamic changes in cellular and microenvironmental composition can be controlled to elicit in vitro human hematopoietic stem cell expansion. Exp. Hematol. 2005; 33:1229-1239.
31. Fitz K M, Ryan L. Hewick M, Clark R M., Chan S C, Loudon S C, Sherman R, Perussia F, Trinchieri B G. Identification and purification of natural killer cell stimulatory factor (NKSF), a cytokine with multiple biologic effects on human lymphocytes. J Exp Med. 1989; 170:827-845.
32. Lertmemongkolchai G, Cai G, Hunter C A, Bancroft G J. Bystander activation of CD8+ T cells contributes to the rapid production of IFN-gamma in response to bacterial pathogens. Journal of Immunology. 2001; 166:1097-1105.
33. Cui J, Shin T, Kawano T, Sato H, Kondo E, Toura I, Kaneko Y, Koseki H, Kanno M, Taniguchi M. Requirement for Valpha14 NKT cells in IL-12-mediated rejection of tumors. Science. 1997; 278:1623-1626.
34. Ohteki T, Fukao T, Suzue K, Maki C, Ito M, Nakamura M, Koyasu S. Interleukin 12-dependent interferon gamma production by CD8alpha+ lymphoid dendritic cells. J Exp. Med. 1999; 189:1981-1986.
35. Airoldi I, Gri G, Marshall J D, Corcione A, Facchetti P, Guglielmino R, Trinchieri G, Pistoia V. Expression and function of IL-12 and IL-18 receptors on human tonsillar B cells. Journal of Immunol. 2000; 165:6880-6888.
36. Hsieh C S, Macatonia S E, Tripp C S, Wolf S F, O'Garra A, Murphy K M. Development of TH1 CD4+ T cells through IL-12 produced by *Listeria*-induced macrophages. Science. 1993; 260:547-549.
37. Manetti R, Parronchi P, Giudizi M G, Piccinni M P, Maggi E, Trinchieri G, Romagnani S. Natural killer cell stimulatory factor (interleukin 12 [IL-12]) induces T helper type 1 (Th1)-specific immune responses and inhibits the development of IL-4-producing Th cells. J. Exp. Med. 1993; 177: 1199-1204.
38. Brunda M J, Luistro L, Warner R R, Wright R B, Hubbard B R, Murphy M, Wolf S F, Gately M K. Antitumor and antimetastatic activity of interleukin 12 against murine tumors. J. Exp. Med. 1993; 178:1223-1230.
39. Noguchi Y, Jungbluth A, Richards E C, Old L J. Effect of interleukin 12 on tumor induction by 3-methylcholanthrene. Proc Natl Acad Sci USA. 1996; 93:11798-11801.
40. Giordano P N, De Giovanni N C, Landuzzi L, Di Carlo E, Cavallo F, Pupa S M., Rossi I, Colombo N I P, Ricci C, Astolfi A, Musiani P, Fomi G, Lollini P-L. Combined Allogeneic Tumor Cell Vaccination and Systemic Interleukin 12 Prevents Mammary Carcinogenesis in HER-2/neu Transgenic Mice. J. Exp. Med. 2001; 194:1195-1206.
41. Colombo M P, Trinchieri G. Interleukin-12 in anti-tumor immunity and immunotherapy. Cytokine Growth Factor Rev. 2002; 13:155-168.
42. Yao L, Pike S E, Setsuda J, Parekh J, Gupta G, Raffeld M, Jaffe E S, Tosato G. Effective targeting of tumor vasculature by the angiogenesis inhibitors vasostatin and interleukin-12. Blood. 2000; 96:1900-1905.
43. Ma X, Chow J M, Gri G, Cana G, Gerosa F, Wolf S F, Dzialo R, Trinchieri G. The interleukin 12 p40 gene promoter is primed by interferon gamma in monocytic cells. J. Exp Med. 1996; 183:147-157.
44. Gazzinelli R T, Wysocka M, Hieny S, Scharton-Kersten T, Cheever A, Kuhn R, Muller W, Trinchieri G, Sher A. In the absence of endogenous IL-10, mice acutely infected with *Toxoplasma gondii* succumb to a lethal immune response dependent on CD4+ T cells and accompanied by overproduction of IL-12, IFN-gamma and TNF-alpha. J. Immunol. 1996; 157:798-805.
45. Marcel E, Harry B. Radiation-induced apoptosis. Cell Tissue Res. 2000; 301: 133-142.
46. Dewey W C, Ling C C, Meyn R E. Radiation-induced apoptosis: relevance to radiotherapy. Int. J Radiat Oncol Biolo Phys. 1995; 33:781-796.
47. Dubray B, Breton C, Delic J, Klijanienko J, Maciorowski Z, Vielh P, Fourquet A, Dumont J, Magdclenat H, Cosset J-M. In vitro radiation-induced apoptosis and early response to low-dose radiotherapy in non-Hodgkin's lymphomas. Radiother Oncol. 1998; 46:185-191.
48. Portielje J E A, Lamers C H J, Kruit W H J, Sparreboom A, Bolhuis R L H, Stoter G, Huber C, Gratama J W. Repeated Administrations of Interleukin (IL)-12 Are Associated with Persistently Elevated Plasma Levels of IL-10 and Declining IFN-$\gamma$ Tumor Necrosis Factor-$\alpha$, IL-6, and IL-8 Responses. Clin. Cancer Res. 2003; 9: 76-83.
49. Eng V M, Car B D, Schnyder B, Lorenz M, Lugli S, Aguet M, Anderson T D, Ryffel B, Quesniaux V F. The stimulatory effects of interleukin (IL)-12 on hematopoiesis are antagonized by IL-12-induced interferon gamma in vivo. J Exp. Med. 1995; 181:1893-1898.
50. Car B D, Eng V M, Schnyder B, LeHir M, Shakhov A N, Woerly G, Huang S, Aguet M, Anderson T D, Ryffel B. Role of interferon-gamma in interleukin 12-induced pathology in mice. Amer. J. Path. 1995; 147:1693-1707.
51. Neta R, Stiefel S M, Finkelman F, Herrmann S, Ali N. IL-12 protects bone marrow from and sensitizes intestinal tract to ionizing radiation. J Immunol. 1994; 153:4230-4237.
52. Zsebo K M, Smith K A, Hartley C A, Greenblatt M, Cooke K, Rich W, McNeice I K. Radioprotection of mice by recombinant rat stem cell factor. Proc Natl Acad Sci USA 1992; 89:9464-9468.
53. Drouet M, Mourcin F, Grenier N, Leroux V, Denis J, Mayol J F, Thullier P, Lataillade J J, Herodin F. Single administration of stem cell factor, FLT-3 ligand, megakaryocyte growth and development factor, and interleukin-3 in combination soon after irradiation prevents nonhuman primates from myelosuppression: long-term follow-up of hematopoiesis. Blood. 2004; 103:878.
54. Herodin F, Bourin P. Mayol J F, Lataillade J J, Drouet M. Short-term injection of antiapoptotic cytokine combinations soon after lethal $\gamma$-irradiation promotes survival. Blood. 2003; 101:2609-2616.
55. Streeter P R, Dudley L Z. Fleming W H. Activation of the G-CSF and Flt-3 receptors protects hematopoietic stem cells from lethal irradiation. Exp. Hematol. 2003; 31:1119-1125.
56. Kucia M. Ratajczak J, Ratajczak M Z. Are bone marrow stem cells plastic or heterogenous—That is the question. Exp. Hematol. 2005; 33:613-623.
57. Meijne E I, van der Winden-van Groenewegen R J, Ploemacher R E, Vos O, David J A, Huiskamp R. The effects of x-irradiation on the hematopoietic stem cell compartment in the mouse. Exp Hematol. 1991; 19:617-623.
58. McCarthy K. Population size and radiosensitivity of marine hematopoietic endogenous long-term repopulating cells. Blood. 1997:89:834-841.
59. Down J, Boudewijn A, van Os R, Thames H, Ploemacher R. Variations in radiation sensitivity and repair among different hematopoietic stem cell subsets following fractionated irradiation. Blood. 1995; 86:122-127.
60. Inoue T, Hirabayashi Y, Mitsui H, Sasaki H, Cronkite E P, Bullis J E Jr, Bond V P, Yoshida K. Survival of spleen colony forming units (CFU-S) of irradiated hone marrow cells in mice: evidence for the existence of a radioresistant subtraction. Exp Hematol. 1995; 23:1296-1300.

61. van Bekkum D. Radiation sensitivity of the hematopoietic stem cell. Rad Res. 1991; 128:S4 8.
62. Wagemaker G. Heterogeneity of radiation sensitivity of hematopoietic stem cell subsets. Stem Cells. 1.995:13 (suppl):257-260.
63. Zuniga-Pflucker J C, Kruisbeek A. M. Intrathymic radioresistant stem cell follow an IL-2/IL-2R Pathway during thymic regeneration after sublethal irradiation. J. Immunol. 1990; 144:3736-3740.
64. Ayukawa K, Tomooka S, Asano T, Taniguchi K, Yoshikai Y, Nomoto K. Radioresistant CD4-CD8-intrathymic T cell precursors differentiate into mature CD4 CD8- and CD4-CD8+ T cells. Development of 'radioresistant' CD4-CD8-intrathymic T cell precursors. Thymus. 1990:15:65-78.
65. Jones R J, Wagner J E, Celano P, Zicha M S, Sharkis S J. Separation of pluripotent haematopoietic stem cells from spleen colony-forming cells. Nature. 1990; 347:188-189.
66. Seung Woo Lee, Yunji Park, Jae Kwang Yoo, So Young Choi, and Young Chul Sung. Inhibition of TCR-Induced CD8 T Cell Death by IL-12: Regulation of Fas Ligand and Cellular FLIP Expression and Caspase Activation by IL-12. J Immunol. 2003; 170:2456-2460.
67. Medical College Of Georgia. "Breast Cancer Uses Growth Factors To Lure Stem Cells." ScienceDaily, 9 Jun. 2005. Web. Retrieved 29 Jun. 2011.
68. Kryczek I, Grybos M, Karabon L, Klimczak A, Lange A. IL-6 production in ovarian carcinoma is associated with histiotype and biological characteristics of the tumour and influences local immunity. Br J Cancer. 2000; 82:621-628.
69. Freedman R S, Deavers M, Liu J, Wang E. Peritoneal inflammation—A microenvironment for Epithelial Ovarian Cancer (EOC). J Transl Med. 2004; 25:23.
70. Jackson J D, Yan Y, Brunda M J, Kelsey L S, Talmadge J E. Interleukin-12 enhances peripheral hematopoiesis in vivo. Blood. 1995; 85:2371-2376.
71. Zhao Y, Zhan Y, Burke K A, Anderson W F. Soluble factor(s) from bone marrow cells can rescue lethally irradiated mice by protecting endogenous hematopoietic stem cells. Exp. Hematol. 2005; 33:428-434.
72. Epstein F H. Cutaneous wound healing. N Engl J Med. 1999; 34:738-746.
73. Engelhardt E, Toksoy A, Goebeler M, Debus S, Bröcker EB, Gillitzer R. Chemokines Il-8, GROa, MCP-1, IP-10, and MIG are sequentially and differentially expressed during phase specific infiltration of leukocyte subsets in human wound healing. Amer. J Pathol. 1998; 153:1849-1860.
74. Gillitzer R, Goebeler M. Chemokines in cutaneous wound healing. J Leuk. Biol. 2001; 69:513-521.
75. Wu C, Warrier R R, Wang X, Presky D H, Gately M K. Regulation of interleukin-12 receptor beta1 chain expression and interleukin-12 binding by human peripheral blood mononuclear cells. Eur J Immunol 1997; 27:147-54.
76. Szabo S J, Dighe A S, Gubler U, Murphy K M. Regulation of the interleukin(IL)-12R β2 subunit expression in developing T helper (Th1) and Th2 cells. J Exp Med 1997; 185: 817-24.
77. Rogge L, Barberis-Maino L, Biffi M, Passini N, Presky D H, Gubler U, Sinigaglia F. Selective expression of an interleukin-12 receptor component by human T helper 1 cells. J Exp Med 1997; 185:825-31.
78. Venezia T A, Merchant A A, Ramos C A, Whitehouse N L, Young A S, Shaw C A, Goodell M A. Molecular signatures of proliferation and quiescence in hematopoietic stem cells. PLoS Biol. 2004 October; 2(10):e301. Epub 2004 Sep. 28.
79. Ivanova N B, Dimos J T, Schaniel C, Hackney J A, Moore K A, Leminchka I R. A stem cell molecular signature. Science. 2002; 298:601-604.
80. The Lineage Cell Depletion Kit is a magnetic labeling system for the depletion of mature hematopoietic cells, such as T cells, B cells, monocytes/macrophages, granulocytes and erythrocytes and their committed precursors. All the secondary antibodies for this system are goat anti-rat IgG conjugated with MicroBeads (Miltenyi Biotec GmbH, Auburn, Calif.)
81. Liddle R A, Misukonis M A, Pacy L, Balber A E. Cholecystokinin cells purified by fluorescence-activated cell sorting respond to monitor peptide with an increase in intracellular calcium. Proc Natl Acad Sci USA. 1992; 89:5147-51.
82. Jordan C T, Astle C M, Zawadzki J, Mackarehtschian K, Lemischka I R, Harrison D E. Long term repopulating abilities of enriched fetal liver stem cells measured by competitive repopulation. Exp Hematol. 1995; 23:1011-1015.
83. de Wynter E, Ploemacher R E. Assays for the assessment of human hematopoietic stem cells. J Biol Regul Homeost Agents 2001; 15:23-27.
84. Zhang C C, Lodish H F. Murine hematopoietic stem cells change their surface phenotype during ex vivo expansion. Blood. 2005; 105.4314-4320.
85. Torok-Storb B, Iwata M, Graf L, Gianotti J, Horton H, Byrne M C. Dissecting the marrow microenvironment. Ann N Y Acad Sci. 1999; 0; 872:164-70.
86. Shih C C, Hu M C T, Hu J, Weng Y, Yazaki P J, Medeiros J, Forman S J. A secreted and LIF-mediated stromal cell-derived activity that promotes ex vivo expansion of human hematopoietic stem cells. Blood. 2000; 95:1957-1966.
87. Afkarian M, Sedy J R, Yang J. Jacobson N G, Cereb N, Yang S Y, Murphy T L, Murphy K M. T-bet is a Stat-1-induced regulator of IL-12R expression in naïve CD4+ T cells. Nature Immunol. 2003; 3:549-557.
88. DeMeyer E S, Baar J. Dendritic Cells: The Sentry Cells of the Immune System. 2001. Monograph. Oncology Education Services.
89. Ozato K, Tsujimura H, Tamura T. Toll-like receptor signaling and regulation of cytokine gene expression in the immune system. Biotechniques 2002; 70, 72 passim supp 66-68.
90. Attar E C, Scadden D T. Regulation of hematopoietic stem cell growth. Leukemia 2004; 18:1760-68.
91. Wang Q, Zhang W, Ding G, Sun L, Chen G, Ciao X. Dendritic cells support hematopoiesis of bone marrow cells. Transplantation 2001; 72:891-899.
92. Jacobsen S E W, Veiby O P, Smeland E B. Cytotoxic lymphocyte maturation factor (interleukin 12) is a synergistic factor for hematopoietic stem cells. J. Exp. Med 1993; 178:413-418.
93. Bystrykh L, Weersing E, Dontje B, Sutton S, Pletcher M T, Wiltshire T, Su A I, Vellenga E, Wang J, Manly K F, Lu L, Chesler E J, Alberts R, Jansen R C, Williams R W, Cooke M P, de Haan G. Uncovering regulatory pathways that affect hematopoietic stem cell function using 'genetical genomics'. Nature Genetics 2005; 37:225-232
94. Zou W. Immunosuppressive networks in the tumour environment and their therapeutic relevance. Nature Review (Cancer) 2005; Sep. 14-25.
95. Hideo E, Nakauchi H. Non-side population hematopoietic stem cells in mouse bone marrow. Blood, first ed.; prepublished online Jun. 27, 2006.
96. Paterson H M, Murphy T J, Purcell E J, Shelley O, Kriynovich S J. Lien E, Mannick J A, Lederer J A. Injury primes the innate immune system for enhanced toll-like receptor activity. Immunol 2003; 171:1473-1483.

97. U.S. Pat. No. 7,939,058 entitled "Uses of IL-12 in Hematopoiesis."

---

What is claimed is:

1. An isolated, substantially homogenous population of cells that: (a) expresses the IL-12 receptor and the cell marker CD34, and (b) has been exposed to exogenous IL-12 ligand.

2. The cell population of claim 1, wherein the cell population is of human origin.

3. The cell population of claim 1, wherein the cells have been isolated before being exposed to exogenous IL-12 ligand.

4. The cell population of claim 1, wherein the cells have been exposed to exogenouse IL-12 ligand while in a subject, and then isolated.

5. The cell population of claim 1, wherein the cell population further expresses a marker selected from the group consisting of Sca-1, CDCP1, c-kit, KDR, Flt3, SLAM, CD133, IFNGR, and any combination thereof.

6. The cell population of claim 1, wherein the stem cell does not express at least one or more major histocompatibility (MHC) class I and class II molecule.

7. The cell population of claim 1, wherein the cell population undergoes expansion in the presence of IL-12 heterodimer ligand.

8. The cell population of claim 1, wherein the cell comprises long-term repopulating (LTR) hematopoietic stem cells.

9. The cell population of claim 1, wherein the cell population is radioresistant.

10. The cell population of claim 1, wherein the source of the cell population is bone marrow, peripheral blood, the spleen, blood from an umbilical cord, or any combination thereof.

11. The stem cell of claim 1, wherein the IL-12 receptor comprises the beta 2 subunit of the IL-12 receptor.

12. A method for generating a cellular transplant for repair of cells and tissue, comprising:
(a) isolating a cell population that expresses the IL-12 receptor and CD34; and
(b) exposing the cell population to exogenous IL-12.

13. The method of claim 12, wherein the population of cells expressing the IL-12 receptor is isolated using an antibody that binds the beta 2 subunit of the IL-12 receptor.

* * * * *